US012201735B2

(12) United States Patent
Deshays et al.

(10) Patent No.: US 12,201,735 B2
(45) Date of Patent: Jan. 21, 2025

(54) MODELING TO ASSIST HIGH-LEVEL UV-C DISINFECTION

(71) Applicant: GERMITEC, Ivry-sur-Seine (FR)

(72) Inventors: René Deshays, Ruoms (FR); Clément Deshays, Paris (FR); Cédric Neveu, Montrouge (FR); Adrian Edward Smith, Emerald Hills, CA (US); Frédéric Lepine, Saint-Gratien (FR)

(73) Assignee: GERMITEC, lvry-sur-Seine (FR)

( * ) Notice: Subject to any disclaimer, the term of this patent is extended or adjusted under 35 U.S.C. 154(b) by 840 days.

(21) Appl. No.: 17/298,888

(22) PCT Filed: Dec. 5, 2019

(86) PCT No.: PCT/EP2019/083862
§ 371 (c)(1),
(2) Date: Jun. 1, 2021

(87) PCT Pub. No.: WO2020/115230
PCT Pub. Date: Jun. 11, 2020

(65) Prior Publication Data
US 2022/0031894 A1 Feb. 3, 2022

Related U.S. Application Data

(60) Provisional application No. 62/776,974, filed on Dec. 7, 2018.

(51) Int. Cl.
*A61L 2/08* (2006.01)
*A61L 2/10* (2006.01)
(Continued)

(52) U.S. Cl.
CPC .......... *A61L 2/085* (2013.01); *A61L 2/10* (2013.01); *A61L 2/24* (2013.01); *G16H 40/40* (2018.01);
(Continued)

(58) Field of Classification Search
None
See application file for complete search history.

(56) References Cited

U.S. PATENT DOCUMENTS

| 9,364,573 B2 | 6/2016 | Deshays et al. |
| 10,111,976 B2 | 10/2018 | Deshays et al. |

(Continued)

FOREIGN PATENT DOCUMENTS

| JP | 2001-025501 | 1/2001 |
| JP | 2009-532092 | 9/2009 |

(Continued)

OTHER PUBLICATIONS

Allen, et al, "A Fully Integrated 10 MeV Electron Beam Sterilization System", 1995, pp. 457-460, vol. 46, No. 4-6, Radiat. Phys. Chem.

(Continued)

*Primary Examiner* — Holly Kipouros
(74) *Attorney, Agent, or Firm* — B. Aaron Schulman, Esq.; Stites & Harbison, PLLC

(57) ABSTRACT

The invention concerns a disinfection device includes a disinfection chamber having an interior volume and a radiation source coupled to the interior volume. The radiation source is arranged to emit disinfecting radiation into the interior volume when in operation. A disinfection program in the disinfection chamber is arranged to control the radiation source to emit the disinfecting radiation according to parameters determined based on at least one of a three dimensional model of the disinfection chamber and a three dimensional model of a target article to be disinfected. The three dimensional model of the disinfection chamber is formed using data collected by operating at least one radiation source in a data collection disinfection chamber, or by providing a disinfection chamber model having a virtual interior volume. The three dimensional model of the target (Continued)

article to be disinfected is formed by providing a target article model having a virtual surface.

14 Claims, 28 Drawing Sheets

(51) Int. Cl.
  *A61L 2/24* (2006.01)
  *G16H 40/40* (2018.01)
(52) U.S. Cl.
  CPC ...... *A61L 2202/11* (2013.01); *A61L 2202/122* (2013.01); *A61L 2202/14* (2013.01); *A61L 2202/24* (2013.01)

(56) References Cited

U.S. PATENT DOCUMENTS

| 2007/0231190 | A1 | 10/2007 | Hyde et al. |
| 2010/0111775 | A1 | 5/2010 | Hyde et al. |
| 2011/0240882 | A1 | 10/2011 | Simmons et al. |
| 2014/0170019 | A1 | 6/2014 | Gil et al. |
| 2014/0341777 | A1 | 11/2014 | Deshays et al. |
| 2015/0056095 | A1 | 2/2015 | Gorzen et al. |
| 2015/0059288 | A1* | 3/2015 | Wu ............ B65B 55/027 53/167 |
| 2015/0246148 | A1 | 9/2015 | Blechschmidt et al. |
| 2016/0279275 | A1 | 9/2016 | Deshays et al. |
| 2016/0354503 | A1 | 12/2016 | Hutchens et al. |
| 2018/0117194 | A1 | 5/2018 | Dobrinsky et al. |

FOREIGN PATENT DOCUMENTS

| JP | 2016-518226 | 6/2016 |
| JP | 2018-166811 | 11/2018 |
| WO | WO2018180464 | 10/2018 |

OTHER PUBLICATIONS

International Search Report for PCT/EP2019/083862 dated Jan. 31, 2020.

* cited by examiner

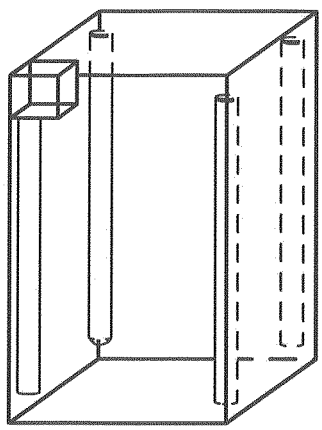
(a)
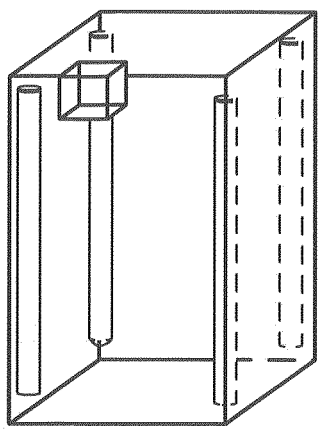
(b)
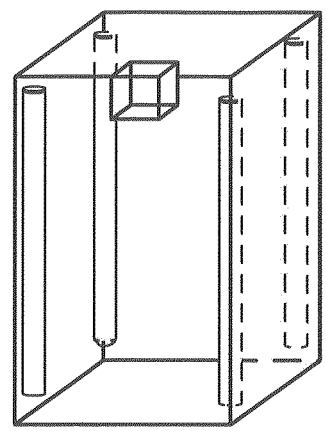
(c)
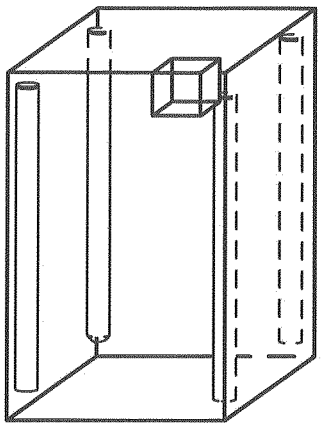
(d)
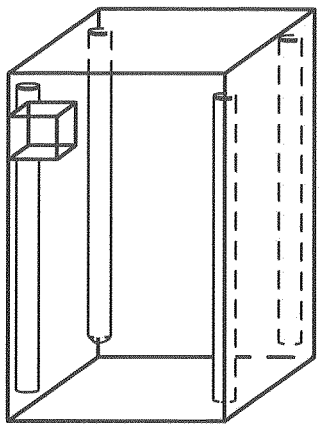
(e)
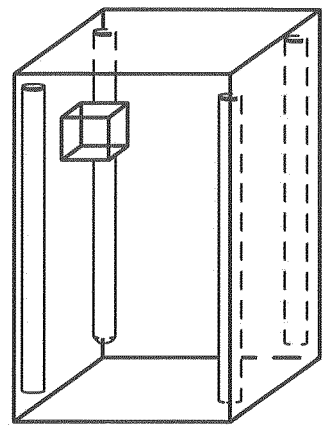
(f)
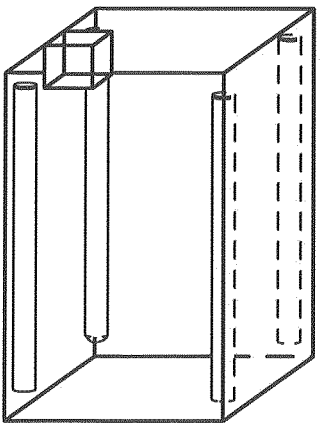
(g)
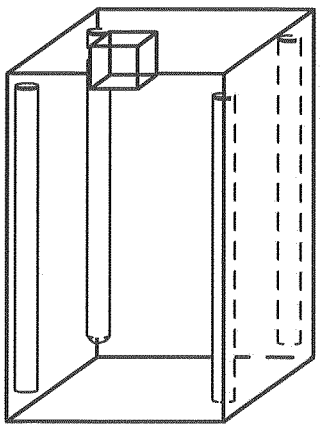
(h)
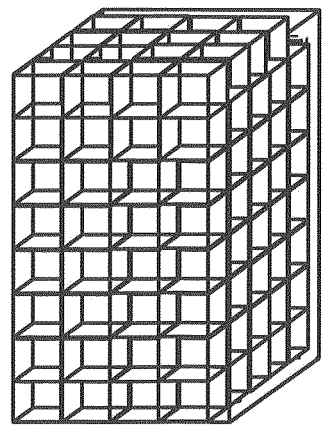
(i)
*Fig. 6B*

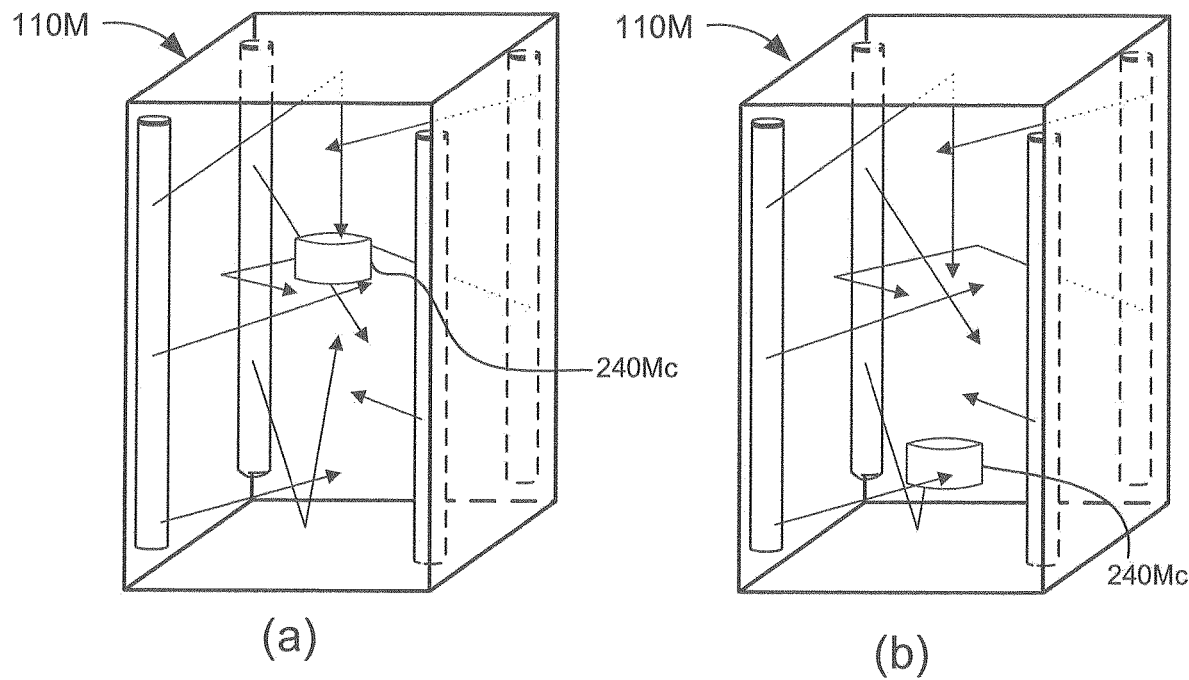
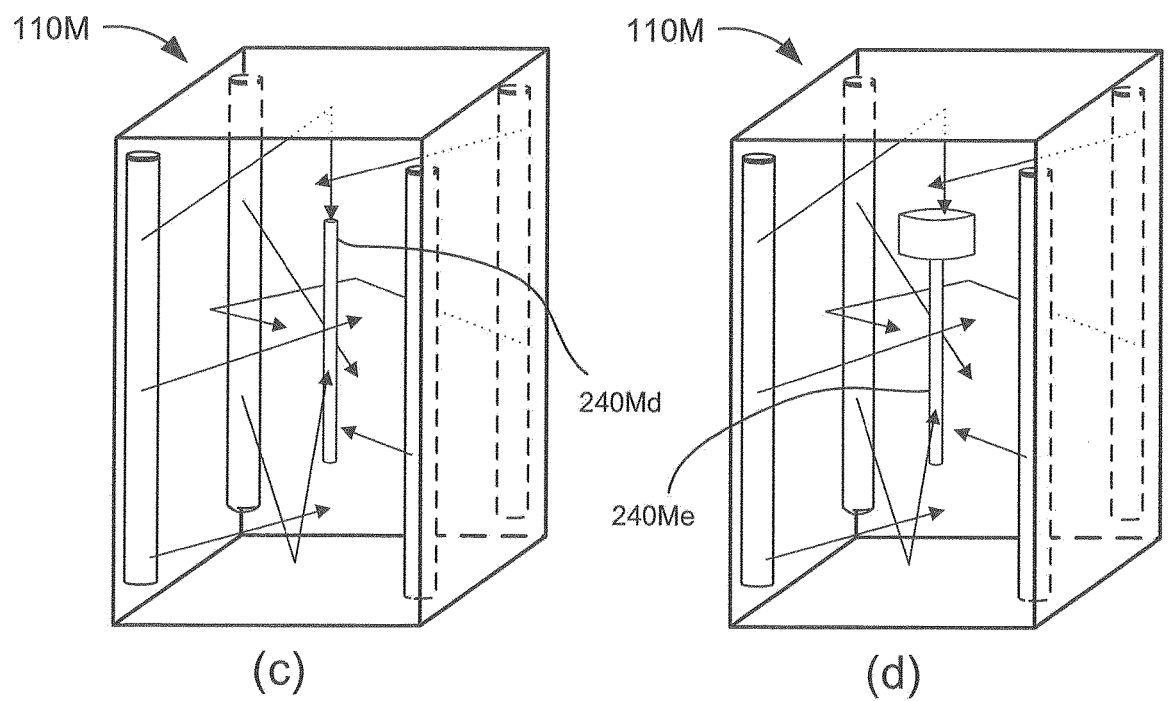
Fig. 7G

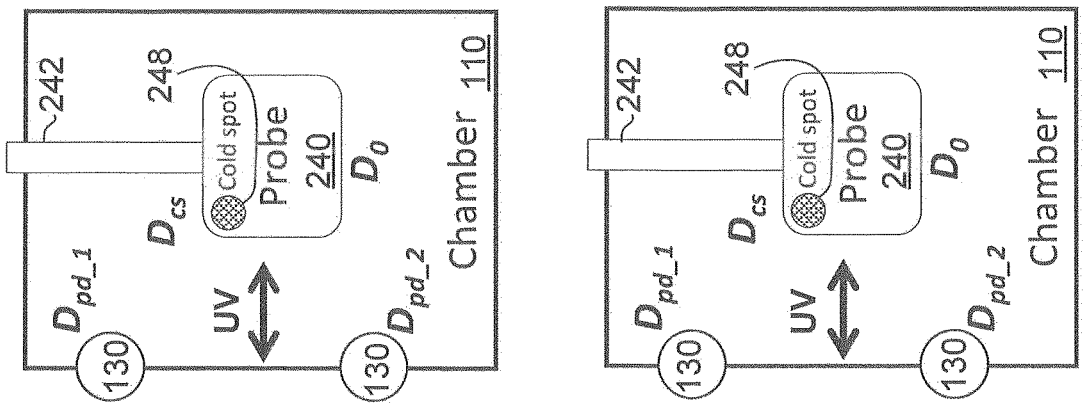
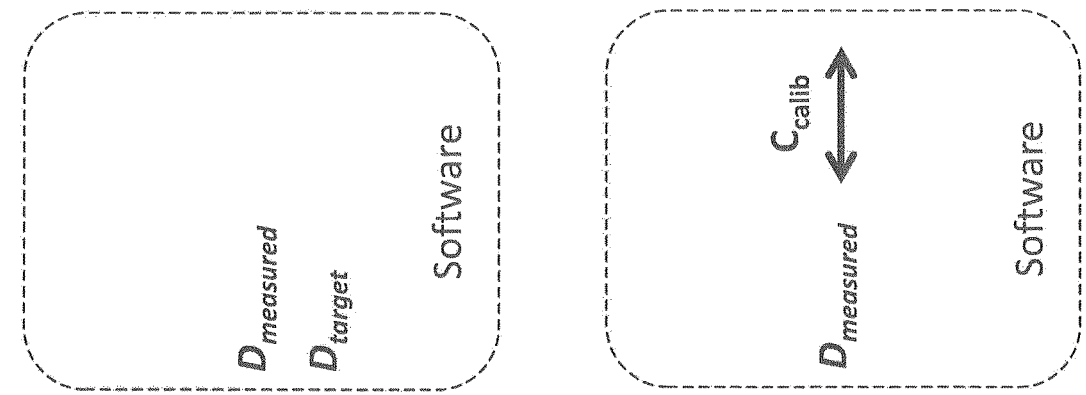
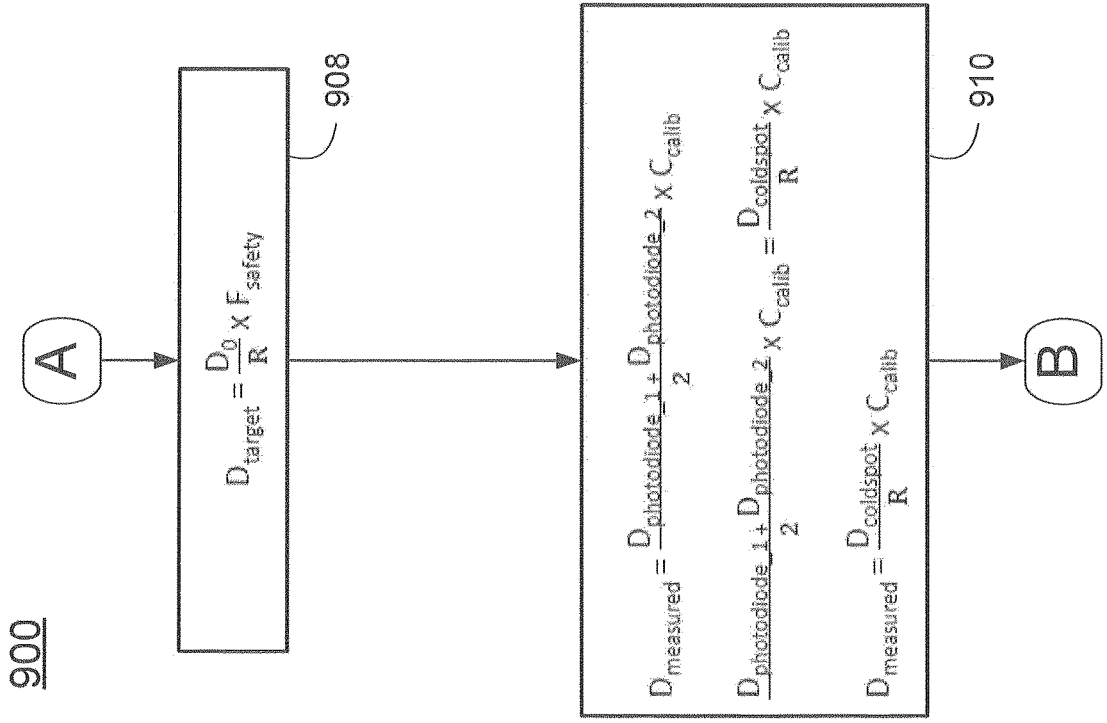
Fig. 9B

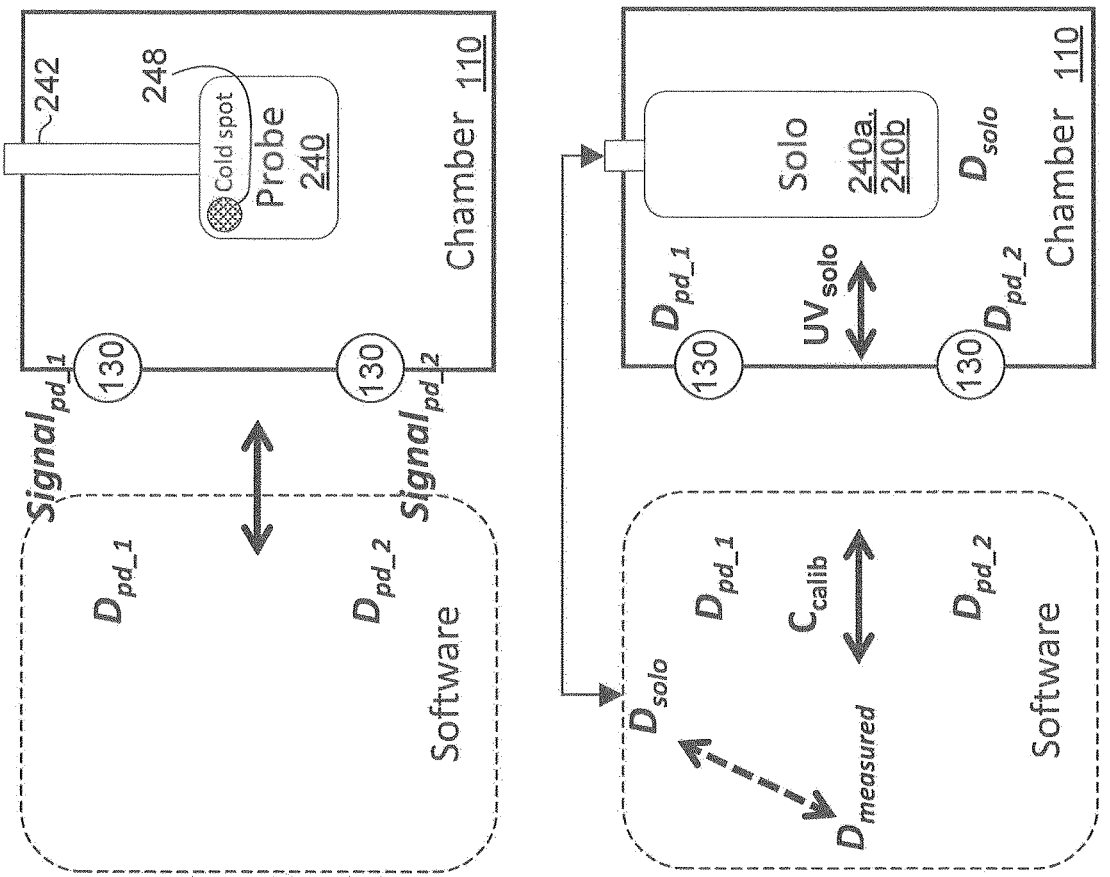
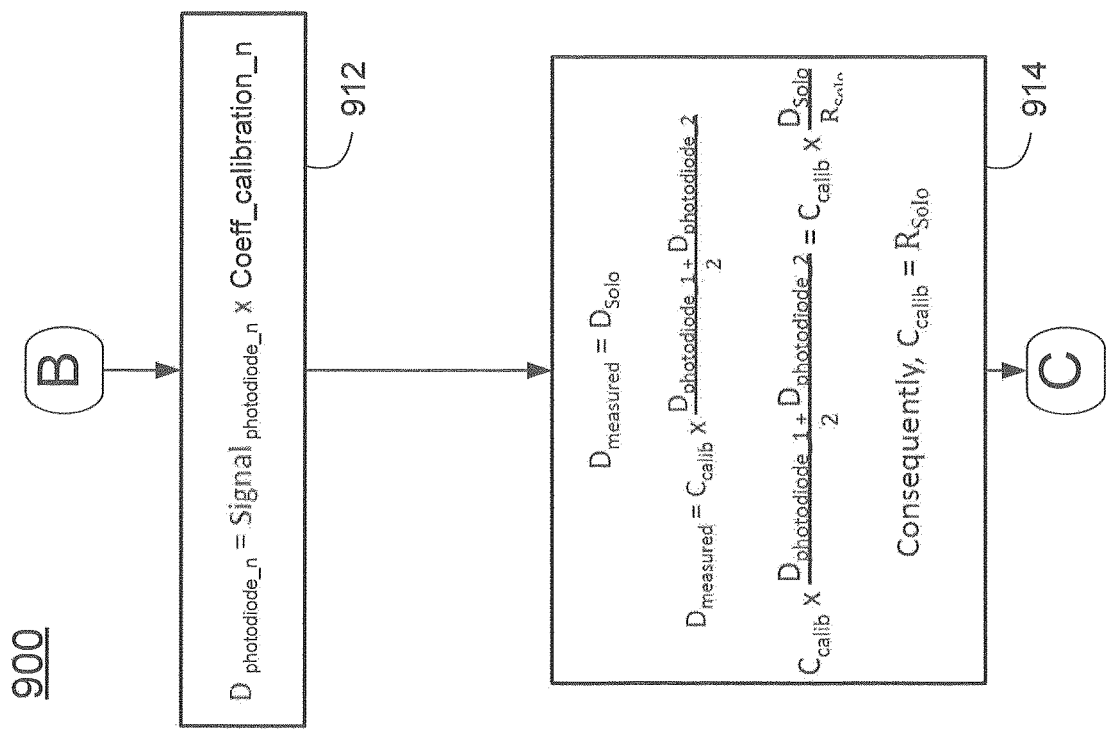
Fig. 9C

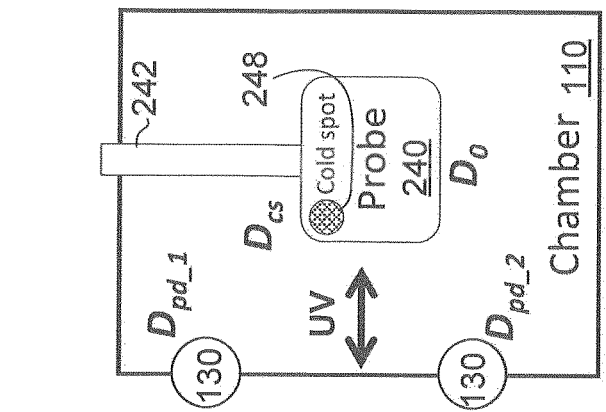
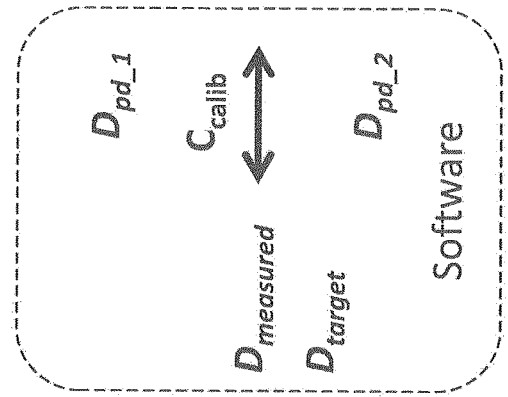
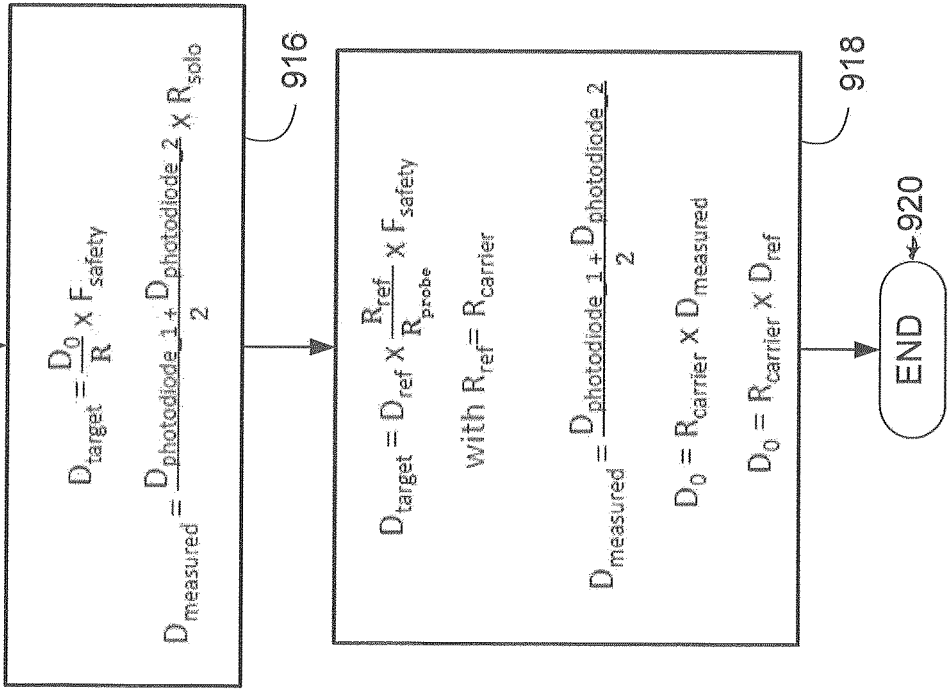
Fig. 9D

MODELING TO ASSIST HIGH-LEVEL UV-C DISINFECTION

BACKGROUND

Technical Field

The disclosure is generally directed to devices and systems for disinfecting target articles. More specifically, but not exclusively, the disclosure relates to methods, devices, and systems that model various portions of disinfection chambers and target articles to assist high-level UV-C disinfection for the modeled target articles.

Description of the Related Art

Proper disinfection or sterilization of reusable medical instruments is important in preventing the person-to-person transmission of pathogenic microbes. The level of sterilization and disinfection applied to medical instruments depends on how the device is classified. The Centers for Disease Control (CDC) classifies a medical instrument as a critical item, semi critical item, or noncritical item, depending on the intended use of the device (CDC Guideline for Disinfection and Sterilization in Healthcare Facilities, 2008). In the CDC Guideline, it is stated that critical items confer a high risk for infection if they are contaminated with any microorganism.

Examples of critical items are devices that contact sterile tissue and include surgical instruments, implants, and ultrasound probes used in sterile body cavities. These devices must be sterilized prior to use.

Semi critical items typically contact mucous membranes or non-intact skin. Exemplary semi critical items include such devices as probes used in vaginal, rectal, and urological exams, equipment for respiratory therapy and anesthesia, and certain endoscopes. These medical devices should be free from all microorganisms; however, some small numbers of bacterial spores are considered permissible. Semi critical items require at least high-level disinfection (HLD).

Noncritical items are those that come in contact with non-mucous membranes of intact skin (e.g., blood pressure cuffs and stethoscopes). In contrast to critical and some semi critical items, most noncritical reusable items may be decontaminated where they are used to achieve intermediate or low levels of disinfection and these items typically do not need to be transported to a central processing area for service.

Because critical items confer a high risk for infection when they are contaminated with any microorganism, they are typically subjected to sterilization processes that kill and remove all microorganisms. Similarly, semi-critical items require high-level disinfection (HLD) where population levels of pathogens are reduced to very low levels prior to or between uses. Some common methods for achieving sterilization or high-level disinfection include treatments using steam and/or chemical disinfectants. Chemical treatments are often used where the article to be treated is heat sensitive, and chemical disinfectants suitable for use in sterilizing or disinfecting medical devices include, for example, glutaraldehyde, hydrogen peroxide, ortho-phthalaldehyde, and peracetic acid with hydrogen peroxide. Currently, some common methods for achieving high-level disinfection of semi-critical medical devices include soaking the devices in a chemical bath. The chemical bath method for semi-critical items may include soaking for shorter periods of time than would be required to assure complete sterilization.

Although effective, there are disadvantages to sterilization and disinfection processes that utilize steam or chemical treatments. For example, the high temperature associated with steam sterilization can damage the instrument being sterilized. Additionally, the chemicals used for chemical sterilization or disinfection are often costly to store and dispose of properly, and their toxicity can present risks to personnel handling them. Furthermore, chemical methods and high heat (i.e., severe heating to high temperatures in steam) systems can cause degradation of the materials used to make the medical device being treated. Steam- or chemical-based processes can also be time consuming with some procedures taking between 15-40 minutes to complete, and these procedures typically require the instrument or device to be removed to a central location for treatment and then returned to the clinical setting. Such prolonged process times remove medical devices from service, which may be a serious problem if the device is used in an Emergency Department setting. Factors such as these can lead to noncompliance with the sterilization or disinfection procedures recommended by the Food and Drug Administration.

Some companies provide devices and systems that can achieve high-level disinfection of target articles that are reusable, in a short time, at a low temperature, and done locally within the clinical setting of use. For example, U.S. Pat. No. 9,364,573 provides a disinfection method and system using a disinfection chamber with a radiation source, wherein high-level disinfection is achieved within 10 minutes (i.e., 600 seconds or less). The temperature within the disinfection chamber is maintained at a low level. One or both of the ambient temperature within the disinfection chamber and the surface temperature of the target article to be disinfected are monitored so that a threshold temperature, e.g., somewhere between 35° C. to 55° C., will be met and will not be exceeded.

BRIEF SUMMARY

Embodiments of devices, systems, and methods are provided to effectively control the disinfection exposure of ultraviolet radiation provided within a disinfection chamber such that a minimum exposure (i.e., minimum dosage) to the radiation is achieved at a target article on each surface portion that is intended for disinfection. The solution determines a model of the disinfection chamber and a model of the radiation intensity generated within the disinfection chamber. The solution also determines a model of the target object being disinfected and a model of the radiation intensity generated within the disinfection chamber when the target object is present. In some cases, a radiation intensity model (i.e., a radiation intensity map of a disinfection chamber) is formed by, or otherwise supplemented with, actual radiation intensity measurement data collected by sensors in an actual and operating disinfection chamber. The solution then calculates the parameters necessary to deliver a minimum dose of radiation to surfaces and locations of interest on the modeled target article within the modeled disinfection chamber. The calculated parameters are used to generate a disinfection program for a disinfection chamber of the modeled type. Then, when a target object of the modeled type is placed in the disinfection chamber of the modeled type, the generated disinfection program is executed.

In at least some cases, variables associated with the modeling and variables associated with the calculated radiation dose are accounted for based on collected or determined data. The data may include any one or more of empirical data, real-time data, hypothesized data, and the like. These variables (e.g., parameters) may be used to adjust (e.g., increase or decrease) a time of radiation delivery, adjust (e.g., increase or decrease) an intensity of radiation, adjust a pattern of radiation delivery, or adjust other parameters in other ways.

In some cases, certain modeled locations of the disinfection chamber, the target article, or both the disinfection chamber and the target article are particularly identified. These certain modeled locations include locations that are expected to receive radiation doses of interest that are higher (e.g., hot spots) or lower (e.g., cold spots) in a particular region of interest than the overall average radiation dose. One or more calculations are made to adjust parameters for delivering radiation into the disinfection chamber such that all locations intended for disinfection receive at least the minimum dose of radiation determined to disinfect to a given level.

In some embodiments, an acceptably accurate confirmation of the delivered radiation dose is achieved. One method to confirm that the desired disinfecting radiation is present in the disinfecting chamber includes collecting data (e.g., radiation intensity, radiation duration, temperature) from sensors within, or otherwise associated with, the chamber. In some cases, the sensors, or the collected sensor data, may be calibrated, modified, or otherwise adjusted based on the modeled radiation intensity (i.e., the radiation intensity map). In at least one exemplary embodiment, an acceptable radiation dose delivery is based on a determination that at least some sensor data has crossed a particular threshold.

By application of one or more of the techniques and apparatus described herein, it is also provided that the disinfection operation is not unnecessarily prolonged such that the utility rate of the disinfected medical instruments is improved and unnecessary risk of damage to the medical instruments caused by needless overexposure to the disinfecting radiation is avoided. Further, the techniques and apparatus provide a way to define the minimum dose of radiation for any target object. That is, when the disinfection chamber and the target medical instrument can be optically simulated (i.e., modeled), alone or in combination, the minimum dose of disinfecting radiation can be determined, and an effective disinfection chamber program can be generated without need for tedious and difficult-to-achieve power mapping measurements of disinfecting radiation incident at a given surface or location.

A method may be summarized as including: providing a disinfection chamber having an interior volume and a radiation source coupled to the interior volume, the radiation source arranged to emit disinfecting radiation into the interior volume when in operation; providing a disinfection program to the disinfection chamber, the disinfection program arranged to control the radiation source to emit the disinfecting radiation according to parameters determined based on a three dimensional model of the disinfection chamber and a three dimensional model of a target article to be disinfected.

The method may further include: forming the three dimensional model of the disinfection chamber by: operating at least one radiation source in a data collection disinfection chamber; collecting radiation data with at least one radiation sensor; and generating, from the collected radiation data, a radiation intensity map representing a plurality of radiation intensity values in a plurality of regions of the data collection disinfection chamber.

The method may further include: forming the three dimensional model of the disinfection chamber by: providing an initial disinfection chamber model having a virtual interior volume; arranging a plurality of virtual polygons to create a mathematical mapping of the virtual interior volume; generating, with a ray tracing program, simulated radiation ray information based on the mathematical mapping of the virtual interior volume; and generating, from the simulated radiation ray information, a radiation intensity map representing a plurality of radiation intensity values in a plurality of regions of the data collection disinfection chamber.

The method may further include: forming the three dimensional model of the target article to be disinfected by: providing an initial target article model having a virtual surface; arranging a plurality of virtual polygons to create a mathematical mapping of the virtual surface; and identifying at least one spot on the virtual surface of non-uniform irradiation.

The method may further include: forming the disinfection program by: calculating a minimum dose of radiation to apply to the target article to be disinfected, wherein calculating the minimum dose includes information associated with at least one identified cold spot; based on the minimum dose, applying data from a radiation intensity map to the three dimensional model of the target article to be disinfected; and creating parameters to control the radiation source to deliver the minimum dose of radiation.

The disinfection program may further be based on a radiation intensity map, the radiation intensity map based on at least one radiation emitting characteristic of the radiation source.

The method may further include: positioning a calibration object in the interior volume; operating the radiation source with the calibration object in the interior volume; measuring a radiation intensity value on a portion of the calibration object with the radiation source operating; and updating a radiation intensity map based on the measured radiation intensity value.

The disinfection program may further be based on a radiation intensity map, the radiation intensity map having multiple radiation intensity values for a same spot in the interior volume, each of the multiple radiation intensity values associated with a time factor of the operating the radiation source.

The time factor may include an age of the radiation source. The time factor may include a time lapse of the operating the radiation source.

A disinfection system may be summarized as including: a disinfection chamber having an interior volume; a radiation source coupled to the interior volume, the radiation source emitting disinfecting radiation into the interior volume when in operation; and a control system configured to: control the radiation source to emit the disinfecting radiation according to parameters determined based on a three dimensional model of the disinfection chamber and a three dimensional model of a target article to be disinfected.

The three dimensional model of the disinfection chamber may be associated with a radiation intensity map created using radiation data collected with at least one radiation sensor or simulated radiation ray information based on a mathematical mapping of the interior volume.

The disinfection system may further include at least one radiation sensor, arranged to measure radiation emitted into the interior volume, wherein the control system may be further configured to control the radiation source based on the measured radiation and based on a calculated minimum dose of radiation to apply to a target article to be disinfected.

The calculated minimum dose may be based on a ratio of radiation delivered to the at least one radiation sensor and radiation delivered to a cold spot of the target article to be disinfected. The calculated minimum dose may further be based on a safety factor.

The disinfection system may further include a storage unit that stores an interior volume patterning unit arranged to generate the three dimensional model of the disinfection chamber.

The disinfection system may further include a storage unit that stores a target article patterning unit arranged to generate the three dimensional model of the target article to be disinfected.

A non-transitory computer readable storage medium may be summarized as containing executable instructions which, when executed by a processor, configure the processor to operate a disinfection system according to a method, the method comprising acts to: provide a disinfection chamber having an interior volume and a radiation source coupled to the interior volume, the radiation source arranged to emit disinfecting radiation into the interior volume when in operation; provide a disinfection program to the disinfection chamber, the disinfection program arranged to control the radiation source to emit the disinfecting radiation according to parameters determined based on a three dimensional model of the disinfection chamber and a three dimensional model of a target article to be disinfected.

Executable instructions which, when executed by a processor, may further configure the processor to operate the disinfection system according to the method, the method may further include acts to: form the three dimensional model of the disinfection chamber by: operating at least one radiation source in a data collection disinfection chamber; collecting radiation data with at least one radiation sensor; and generating, from the collected radiation data, a radiation intensity map representing a plurality of radiation intensity values in a plurality of regions of the data collection disinfection chamber. Executable instructions which, when executed by a processor, may further configure the processor to operate the disinfection system according to the method, the method may further include acts to: form the three dimensional model of the disinfection chamber by: providing an initial disinfection chamber model having a virtual interior volume; arranging a plurality of virtual polygons to create a mathematical mapping of the virtual interior volume; generating, with a ray tracing program, simulated radiation ray information based on the mathematical mapping of the virtual interior volume; and generating, from the simulated radiation ray information, a radiation intensity map representing a plurality of radiation intensity values in a plurality of regions of the data collection disinfection chamber. Executable instructions which, when executed by a processor, may further configure the processor to operate the disinfection system according to the method, the method may further include acts to: form the three dimensional model of the target article to be disinfected by: providing an initial target article model having a virtual surface; arranging a plurality of virtual polygons to create a mathematical mapping of the virtual surface; and identifying at least one spot on the virtual surface of non-uniform irradiation. Executable instructions which, when executed by a processor, further configure the processor to operate the disinfection system according to the method, the method further comprising acts to: form the disinfection program by: calculating a minimum dose of radiation to apply to the target article to be disinfected, wherein calculating the minimum dose includes information associated with at least one identified cold spot; based on the minimum dose, applying data from a radiation intensity map to the three dimensional model of the target article to be disinfected; and creating parameters to control the radiation source to deliver the minimum dose of radiation.

This Brief Summary has been provided to introduce certain concepts in a simplified form that are further described in detail in the Detailed Description. Except where otherwise expressly stated, the Brief Summary does not identify key or essential features of the claimed subject matter, nor is it intended to limit the scope of the claimed subject matter

BRIEF DESCRIPTION OF THE SEVERAL VIEWS OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which:

FIG. 6B illustrates one method of forming a disinfection chamber model;

FIG. 7G shows various exemplary models of radiation vectors formed in a disinfection chamber model when a certain target article model is present (FIGS. 7A to 7G may be collectively referred to herein as FIG. 7);

FIGS. 9A to 9D are a data flow diagram representing a minimum dose determination procedure (FIGS. 9A to 9D may be referred to collectively as FIG. 9);

DETAILED DESCRIPTION

I Overview

Figure 1:
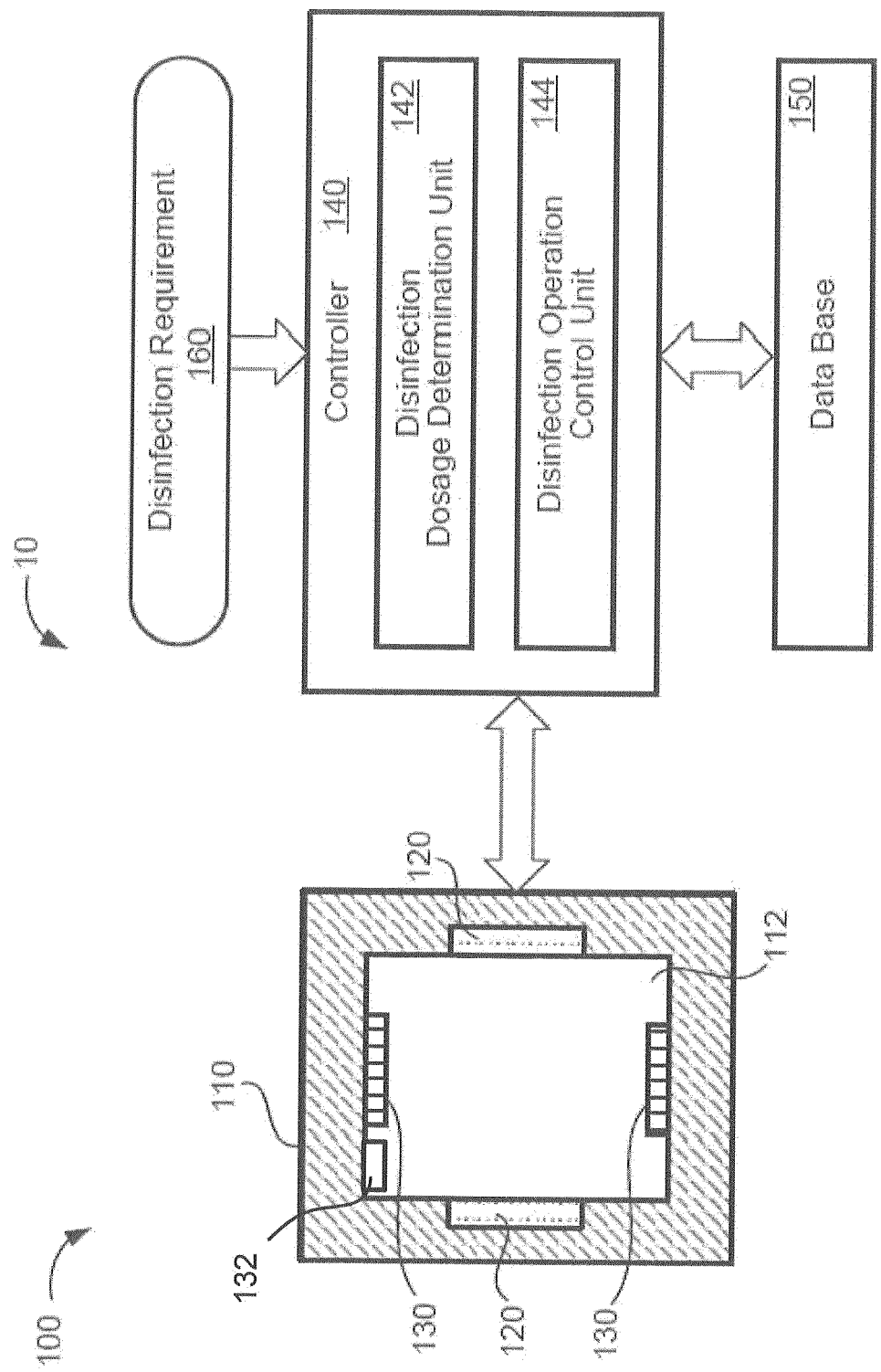
FIG. 1 depicts an exemplary disinfection device embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with computing systems including client and server computing systems, as well as networks have not been shown or described in detail to avoid unnecessarily obscuring descriptions of the embodiments.

The present invention may be understood more readily by reference to this detailed description of the invention. The terminology used herein is for the purpose of describing specific embodiments only and is not limiting to the claims unless a court or accepted body of competent jurisdiction determines that such terminology is limiting. Unless specifically defined herein, the terminology used herein is to be given its traditional meaning as known in the relevant art.

Prior to setting forth the embodiments, however, it may be helpful to an understanding thereof to first set forth definitions of certain terms that are used hereinafter.

The terms "minimum dose," "minimum radiation dose," "minimum dose of radiation," and the like, are used, in all their grammatical forms, throughout the present specification and claims, to refer to the amount of radiation (e.g., a radiation field intensity, a disinfection exposure, or the like) delivered into a chamber sufficient to reduce a population of undesirable biological pathogen (organisms, cells, spores, bacterium, or the like) by a determined acceptable amount. The minimum dose may be determined and delivered using any appropriate mechanism or method. The minimum dose of radiation to which a specified surface or location is exposed (i.e., the disinfection exposure) results in at least the desired level of disinfectant action, which may be by way of sterilization, killing, or other disablement of the targeted pathogens present on a specified surface or location. In the present application, the minimum dose of radiation is inclusive of, but not limited to, factors such as angle of incidence of incoming radiation with respect to the impacted surface, absorbance, reflectance, and properties of the pathogen itself that may affect the volume of radiating photons that perform a disinfecting action on the subject pathogen, regardless of whether or not such factors are expressly accounted for. Accordingly, the minimum dose may be understood as an aggregated dose of radiation delivered into a chamber or otherwise imposed on a subject surface. In particular and without limiting the foregoing, a minimum dose refers to a number or volume of kill units. The number or volume of kill units represents an amount of radiative energy (e.g., fluence) passing through a given elemental area or volume in all directions. The amount of energy may be measured, for example, in Joules (J), Joules per square centimeter (J/cm$^2$), Joules per second (Watts), or any other suitable unit of measure.

The term "low temperature," is used to mean less than about 55° C. For example, in some cases of the systems, devices, and methods described herein, it is desired to maintain the disinfection chamber, and/or target objects therein, from exceeding one or more threshold temperatures, such as a preferable low temperature below about 35° C. and an acceptable low temperature below about 55° C.

Devices and systems are described that effectively control the disinfection exposure of radiation provided (e.g., generated, supplied, delivered, or the like) in a disinfection chamber. In this way, a selected or otherwise desired minimum exposure (i.e., minimum dosage) of radiation is delivered to a target article at each surface portion where disinfection is desired.

One or more computer simulated models of a target object and a disinfection chamber are generated (i.e., a three dimensional model of a target object, a three dimensional model of a disinfection chamber). These models may optionally include information that accounts for hanger systems, calibration fixtures, sensors, foreign objects, and the like. One or more models of radiation intensity (i.e., the amount of radiative energy received at a given elemental area or volume at a determined location per unit time) within the disinfection chamber are also generated based on the structural configuration of the disinfection chamber, which may include optional structures (e.g., hanger systems, fixtures, sensors, etc.) and the radiation light emitting characteristics of the specific radiation sources arranged to emit energy into the disinfection chamber. In this way, the optical properties (e.g., radiation light reflection, diffusion, absorption, and other such properties) of the target article to be disinfected and the chamber itself are considered in the generation of the radiation model. For example, in some embodiments, the surface structural configuration of the target article and the surface material of the target article are determined and modeled in the determination of the radiation intensity model within the interior volume of the disinfection chamber.

The radiation intensity models (e.g., radiation intensity maps) may predict or otherwise simulate radiation intensity in any number of locations within the interior volume of the disinfection chamber. These maps may be discrete, computer derived simulations on contiguous/continuous naturally occurring distributions. The discrete nature, when chosen to be finely enough resolved, is sufficient to accurately approximate a real, continuous distribution of intensity. Some radiation intensity maps simulate/predict radiation intensity in an empty chamber, and some radiation intensity maps simulate/predict radiation intensity in an occupied chamber. The radiation intensity maps associated with an occupied chamber may represent radiation intensity when the disinfection chamber is occupied by a medical device (e.g., one or more medical probes of any type). Other radiation intensity maps associated with an occupied chamber may reflect radiation intensity when the disinfection chamber is occupied by a foreign object such as a medical glove or writing instrument accidentally left in the chamber, specific apparatus to position or orient the target object, or the like. In some cases, the radiation intensity in a given disinfection chamber is confirmed by actual radiation intensity measurements that provide a map of radiation intensity within an interior volume of the disinfection chamber.

In some cases, one or more initially determined radiation intensity maps may be adjusted based on a calibration object positioned within the disinfection chamber. For example, the actual radiation field intensity present at various portions of the calibration object may be detected and measured by one or more sensors attached to one or more surfaces of the calibration object and in addition, or in the alternative, one or more sensors attached to the interior volume of the disinfection chamber. The detected radiation intensity measurement data is compared with simulated data resulting from one or more selected radiation intensity models to calibrate or otherwise adjust the particular radiation intensity map. The adjustments may include updating an initial radiation map/model by at least one of a local adjustment of the radiation intensity values on some disinfection regions map or a global update of the algorithm that generates the computed radiation intensity values in the radiation map/model. The updated radiation map may then be used to determine one or more radiation dosages that will be applied to disinfect surfaces of a target article in the disinfection chamber.

In some cases, it may be desired that at least a minimum dose of disinfecting radiation is delivered to each and every potentially contaminated and exposed surface, intended for disinfection, of the target article so as to ensure with acceptable confidence that the desired level of disinfection is achieved. A disinfection operation is conducted to achieve the determined target disinfection exposure. The disinfection operation is directed by a processor associated with the disinfection chamber executing a program generated at least in part from a model of the disinfection chamber, a model of the target medical device, and one or more radiation intensity maps. The disinfection operation is monitored by sensors on board the disinfection chamber, and the monitored data (e.g., temperature data, radiation intensity data, time data) is further used to control the disinfection operation. With techniques along these lines, the disinfection operation achieves the desired level of disinfection of all surfaces intended for disinfection, and the operation is not unnecessarily prolonged. In this way, by directing the disinfection process to be as short as reasonably possible, the utility rate of the disinfection system is improved, and further, unnecessary risk of excess radiation exposure-derived damage to disinfected medical instruments is avoided.

In embodiments described herein, with the determined minimum dosage, the temperature within the disinfection chamber is maintained at an appropriately low level. One benefit of maintaining the temperature inside the disinfection chamber at a low level is that damage to the medical instrument will be reduced by avoidance of prolonged exposure to disinfecting radiation. It is known that in the presence of intense radiation exposure, elevated temperatures may accelerate deleterious effects such as aging, crazing, cracking, hardening, softening, oxidizing, or otherwise chemically or physically altering, including discoloration, of the materials that comprise the target article. Hence, another benefit of maintaining the interior volume of the disinfection chamber at low temperature is to avoid or reduce such discoloration and aging. In some cases, for example, the generated program for the disinfection chamber may provide a minimum dose of radiation and may provide monitoring the temperature in the disinfection chamber to not exceed 35° C. to 55° C.

Though not limited in application to critical and semi-critical medical devices, the disclosed methods, devices, and systems are particularly suited to high-level disinfection of reused medical devices and instruments, including, for example, ultrasound, endotracheal, and other endocavity probes. In particular embodiments, the devices and systems described herein utilize ultra-violet ("UV") radiation to rapidly accomplish high-level disinfection without generating unacceptably high temperatures on the surface of and within the articles being processed. Many medical instruments are comprised of polymeric materials, and it is known that heating of polymers can accelerate potential damage or degradation that may result from exposure to radiation during the disinfection process. Applied use of the systems and methods disclosed herein reduce the likelihood of such damage or degradation.

In at least some cases, the disinfection chamber is further arranged to reduce damage to disinfected objects by pretreating the chamber prior to radiative disinfection. It is known, for example, that oxygen may negatively affect polymer-based materials. Pretreatment may include, for example, purging oxygen from the disinfection chamber by flushing the chamber with nitrogen, filling the chamber with a neutral (e.g., inert) gas such as argon, or taking one or more other pretreatment actions.

A disinfection chamber of the disclosure may include a housing having a plurality of sidewalls, a top, and a door providing access to the disinfection chamber. The disinfection chamber itself may also include at least one wall defining an interior volume, and in some embodiments, the disinfection chamber will include a plurality of sidewalls, a base, and a top having an open central portion. Where the method and device utilize UV radiation, the disinfection chamber may include one or more reflective interior surfaces, one or more sources of UV radiation ("radiation source"), such as, for example, one or more sources of UV-A, UV-B, or UV-C radiation, and one or more radiation sensors. Reflective materials suitable for use in a disinfection chamber as described herein include, for example, aluminum Grand Brilliant by ALMECO GROUP, polytetrafluoroethylene (PTFE), polyvinyl alcohol (PVA), barium sulfate-containing paints, or combinations thereof. Other materials, for example, the reflective materials disclosed in U.S. Pat. No. 3,956,201 at Col. 2, Lines 56-61 and in the examples of Col. 7, Line 50-Col. 12, Line 2 and in other places and in U.S. Pat. No. 3,764,364 at Col. 2, Line 70-Col. 3, Line 20 and in other places, the contents of which are incorporated herein by reference, may also be employed. In order to facilitate placement and disinfection of articles to be processed within the disinfection chamber, the chamber may also include a suspension assembly for hanging, containing, or otherwise maintaining the article to be disinfected in a desired position within the disinfection chamber.

The disinfection chamber is sized and configured to help achieve disinfection of the articles placed therein within a desirable, and in some cases selectable, period of time such that surfaces of the articles are exposed to a desired level of radiation, referred herein as "dosage." As appreciated, a level of radiation exposure (i.e., a "dose") relates to both the radiation intensity and the time duration of exposure. For example, the target article to be disinfected, UV radiation source(s), and/or UV radiation sensor(s) may be positioned (e.g., introduced, interposed, suspended, or located) within the disinfection chamber at stationary or non-stationary locations that improve exposure of the article to radiation via controlled transmission of radiation from the sources. That is, any one or more of the target article, hangers or other target article positioning devices, sensors, radiation source (s), including one or more of direct sources of UV radiation, and indirect sources of UV radiation (e.g., dedicated reflectors of radiation rays), may be non-stationary during a disinfection cycle. In such embodiments, the disinfection chamber is configured and operated such that one or more of the article, a direct source(s) of UV light, and/or an indirect source(s) of UV light is moved (e.g., rotated in one or more planes, raised and lowered, and the like) within the disinfection chamber during a disinfection cycle to better expose each of the surface portions of the article to selected disinfecting levels of UV radiation, namely the minimum dosage.

In at least some cases, a determination that a minimum dose of radiation has been delivered is facilitated via radiation sampled in the chamber during the disinfection process. The radiation may be directly collected/sampled, or indirectly sampled after transport, by various means to a detector or array of detectors. The one or more detectors may reside within or outside the disinfection chamber. Mirrors or other reflective surfaces, lenses, light pipes, optical fiber cables, or any other optics may be used to facilitate delivery of a representative radiation "signal" from within the chamber to the one or more sensors. Radiation collection may be narrow, moderate or wide field of view depending on the incoming angles of incidence of the radiation that is preferably collected. Since the detector may be emulating an exposed surface of a target object, it may be advantageous to use a detector with a very wide angle of acceptance to collect (e.g., sample) incident radiation. In other cases, it may be preferred to use an integrating sphere or other optical collector with a similar function to attempt to sample radiation from all directions of incidence. In other cases it may be preferred to limit the angle of incidence to inbound radiation traveling toward the detector within a narrow range of incident angles.

Other factors may optionally be considered when determining a minimum dose for a specific target article. Some of these optional factors, which may be described in more detail, include the number of UV radiation sources and their associated radiation emitting characteristics (e.g., input power, output intensity of UV radiation instantaneously and over time, age of radiation source, and the like). Still other optional factors that may be considered are the inclusion or selection of material used to create one or more reflective surfaces, the size and shape of the disinfection chamber, the size and shape of the target article, the orientation and positioning of the target article, whether or not the target article or any structures within the disinfection chamber can be moved during a disinfection protocol, and any other such factors.

In the description herein, the term "radiation source" is generally used to refer to any source of radiation, including direct radiation source and/or indirect radiation source arranged in association with a disinfection chamber. The determination of a disinfection exposure may consider the exposure of a target article to all radiation sources. For example, the age of the radiation source, the fluctuation of the radiation output intensity, the characteristic frequency/wavelength range of radiation light emission, and the time dependent variation of radiation output may all be characterized for a radiation source and factored in the determination of the disinfection exposure.

The structural configurations and radio-optical characteristics of an interior volume of a disinfection chamber are also identified and factored in the determination of the radiation dosage. In an example, the structural configuration of the interior volume is identified in relation to a target article to be positioned within the interior volume and the radiation source(s) coupled to emit radiation rays within the interior volume. For example, the structural configuration of the interior volume and the positioning of the target article will affect an angle of radiation rays directly and/or indirectly reaching a portion of the target article, which in turn affects the radiation intensity on the portion of the target article.

In order to facilitate positioning of target articles to be processed within the disinfection chamber, the disinfection chamber may also include an attachment mechanism, such as a suspension assembly, for hanging, containing, or otherwise maintaining the target article to be disinfected in a stationary or non-stationary selected position, alignment, and/or orientation within the interior volume of the disinfection chamber. Any suitable configuration for such assembly can be utilized. For example, the assembly may be configured to suspend the article under the influence of gravity from a central portion of the top of the disinfection chamber. In other variations, an attachment mechanism may be provided that couples, in a removable manner, the article to an assembly or wall within the disinfection chamber and/or positions and orients the article within the disinfection chamber. Said attachment system may be applied to, or interact with, a region on the target article that is not targeted for disinfection. For example, on the cable of a probe that is attached to an imaging system, or on a region of an independent (e.g., unattached) device that is considered non-critical and thus does not require disinfection treatment. Even further, an attachment mechanism suitable for use in the disinfection chamber may comprise a pair of, pairs of, or sets of complementary mating elements. Assemblies for restraining, maintaining, or positioning an article within the disinfection chamber may optionally include components made of UV transparent material so as to restrain the article but not interfere with passage of the disinfecting UV radiation. Configurations might include tubes, holding forks, positioning surfaces, or any other suitable structures. These assemblies may be arranged fixedly to receive the article, or they may translate and rotate, or otherwise move into position, be moveable, for example, in a clamshell manner, or in combination with movement of the target article, so as to come together to capture, fixate, or trap the article to be disinfected.

Systems according to the present disclosure include a disinfection device having a disinfection chamber and one or more radiation sources as described herein operated to achieve disinfection of one or more target articles. In specific embodiments, the disinfection device is operated according to a generated disinfection program (e.g., an algorithm, a protocol, a software program, or the like) that will deliver the determined minimum dose of radiation as described herein. In such embodiments, one or more target articles are positioned within the disinfection chamber of the disinfection device, and exposure of the one or more articles to an environmental condition capable of disinfecting the articles (e.g., exposure to UV radiation) is initiated based on the determined disinfection exposure, which includes radiation intensity and exposure duration. Once the disinfection condition is initiated/imposed, one or more inputs can be collected and processed according to the generated disinfection program.

In specific embodiments, systems according to the present description are operated according to one or more algorithms of the generated disinfection program for determining, calibrating, or adjusting one or more of the system conditions that cooperate to deliver the determined minimum dose to the target article. The one or more algorithms may include provisions to determine whether the minimum dose has been reached on all portions of a target article intended for disinfection. The one or more algorithms may be arranged to determine where, when, and how the disinfection conditions may be terminated (i.e., the "termination point" or "point for termination"). The one or more algorithms may be arranged to extend the process for irradiating the target article, or for signaling a point at which the disinfection conditions are terminated in order to avoid unwanted damage to the one or more target articles being processed. The information processed according to the one or more algorithms and utilized by the systems described herein may include, for example, determinations of exposure to a disinfecting condition, the temperature at various locations within the disinfection chamber or at the surface of the target articles being disinfected, and time over which articles are exposed to a disinfecting condition. Information collected may be processed in ways to improve the accuracy of data measurements. For example, measured UV exposure may be integrated, averaged, or otherwise consolidated across multiple sensors appropriately reporting/representing the disinfecting power level present within the disinfection chamber. Additional examples of information that can be collected via monitors, sensors, or another input mechanism (e.g., timer, user input parameters, or the like) and then processed by one or more algorithms utilized in operating a system as described herein including the operational status and/or output of UV radiation sources, their level of cleanliness, the presence or absence of internal reflective or absorptive surfaces, the status or responsiveness of UV radiation sensor(s), and other factors that may induce variability in the disinfection conditions over time. Dirtiness of the surface of a target article, or some other assessment of the target article's condition, and thus suitability for disinfection, may also be assessed by one or more detectors to ensure the article has, for example, been pre-cleaned properly before disinfection.

The disinfection system can be operated manually such that one or more operators are directed by a generated disinfection program to load one or more test articles within the disinfection device, initiate a disinfection cycle, monitor the system parameters necessary for execution of an algorithm utilized to determine the termination point for the cycle, and terminate the disinfection cycle according to the algorithm. The disinfection system can be operated semi-automated such that one or more of the tasks required for operation, such as, for example, monitoring of the system parameters, applying an algorithm to determine the termination point for a given disinfection cycle, or terminating a disinfection cycle, is automated or otherwise directed by a generated disinfection program. Additionally, or in the alternative, the disinfection system can be operated fully automated. For purposes of the present disclosure, a fully automated system is one in which, once a generated disinfection program is initiated by an operator, each of the subsequent steps through termination of the disinfection cycle are automated.

In particular embodiments, the systems disclosed herein include one or more processors capable of executing a generated disinfection program that directs one or more algorithms that carry out the disinfection and perform other peripheral tasks. For example, in some cases, the one or more algorithms are operable to calibrate system components, monitor disinfection conditions, and terminate a disinfection cycle. In these or other cases, the one or more algorithms may optionally be arranged to analyze sensor data (e.g., digital imagery from a camera, digital data from an infrared sensor, electronic signals from mating components) to determine how the target article is placed or otherwise oriented in the disinfection chamber. In this way, the algorithm can assess any number of hot spots on the target article, cold spots on the target article, or other regions of interest on the target article along with the current condition/state of the disinfection chamber to deliver radiation. Based on the assessment, the algorithm can calculate an appropriate minimum dose of radiation in real time and adjust the generated disinfection program accordingly. This beneficial analysis can account for the fact that a target article might not be positioned in the disinfection chamber exactly in the same way or location each time. And if by the assessment the algorithm determines that a target article is too far out of position (e.g., too high, too low, rotated unfavorably, or the like) to effect a suitable minimum dose of radiation, the system can alert a user of the errant condition, thereby permitting the user to correct the problem (e.g., reposition the target article, re-start the algorithm, adjust other parameters, or the like). In some cases, the system is provided with an ability to reposition the target automatically, manually, or automatically and manually. In these or other cases, the system is provided with an ability to adjust the radiation sources to supply more or less radiation to the chamber in a spatially preferred manner and thus to compensate for the errant position.

In some embodiments, one or more algorithms of the generated disinfection program assess and/or determine the point of termination for a disinfection cycle based on one or more system conditions. For example, measurements may be taken from one or more sensors throughout the disinfection cycle of at least: 1) an average of or point exposures to a disinfecting condition, measured from one or more sensors, 2) total exposure to a disinfecting condition as measured from one or more sensors, 3) a combination of average exposure to a disinfecting condition measured by one or more sensors considered together with total exposure to the disinfection condition measured at one or more sensors, 4) duration or elapsed time of actual exposure to a disinfecting condition, 5) temperature, such as one or more of a temperature measured within the disinfection chamber and/or at one or more surface temperatures at positions of interest on the target article subjected to the disinfection cycle, and 6) the operating conditions of system components, such as, for example, one of more radiation sources or sensors.

In some cases, one or more sensors may also interrogate the surface of the target article to determine its level of cleanliness. Methods for rapid, high-level disinfection of target articles are also provided herein. Methods disclosed can be carried out under conditions that are less prone to damage or degrade the one or more articles being disinfected. For example, using UV radiation, methods according to the present disclosure can accomplish a "rapid" high-level disinfection of a medical device in a matter of minutes (e.g., less than 10 minutes), while maintaining conditions such that the surface temperatures of target devices being disinfected do not exceed a selected upper threshold, for example, no more than 55° C. In even more specific embodiments, the methods described herein may use UV-C radiation to accomplish the selected high-level of disinfection within a time period considered acceptably short (i.e., "rapid") to make the disinfected device available for reuse in the clinical or treatment setting. Times of a rapid high-level disinfection of a target medical device include from 5 minutes or less, 3 minutes or less, 1.5 minutes or less, and 1 minute or less. The rapid disinfection cycle times provided by methods described herein can lead to improved productivity and compliance with the disinfection protocols, and also avoid undesired thermally accelerated radiation (e.g., UV) degradation of the target articles being disinfected.

The chosen minimum dosage of radiation exposure according to the present disclosure serves to provide acceptable disinfection and serves to mitigate or otherwise reduce degradation of component materials and or joints or connections between components of the test articles being disinfected. The methods, devices, and systems provided are suited to eliminating a non-limiting, non-exhaustive range of microorganisms ("contaminants"), including, for example, *mycobacterium* species, *Escherichia coli, Staphylococcus aureus, Tricophyton mentagrophytes, Pseudomonas aeruginosa, Enterococcus hirae, Bacillus subtilis, Bacillus cereus, Clostridium sporogenes, Candida albicans*, orthopoxvirus, enterovirus, adenovirus type 5, and human papilloma virus. As appreciated, the minimum dosage may be calculated based on any one or more of the radiation intensity map, the type of contaminants, the disinfection requirement and characteristics of the target article, the characteristics of the disinfection chamber, measured and/or calculated real-time data (e.g., sensor data), and other such factors as discussed in the present disclosure.

Methods for determining acceptable disinfection conditions for a given target article, microorganism, or type of contamination are also provided. In order to better identify the conditions required for disinfection and to reduce the potential for undesired over-exposure or under-exposure of articles to disinfection conditions, methods described herein provide for setting and confirming operational parameters of the disinfection devices and systems described herein using test data collected for targeted microorganisms. For example, in specified embodiments, testing of one or more pathogens of interest is conducted, wherein a known amount of selected pathogen(s) (e.g., live bacteria, dormant spores, fungi, molds, viruses, and the like) is exposed to a controlled disinfection condition (e.g., a known dose of UV radiation, in energy delivered per unit area). The known amount of the selected pathogen(s) can be deposited on a substrate, such as a glass/polymeric/ceramic/metal substrate, and exposed to UV radiation delivered from a UV source positioned to provide a known and controlled dose of UV radiation. At least one example of systems and devices to perform such pathogen testing is disclosed in PCT/US2017/043264, entitled Bioassay Carrier And Preparation Thereof, filed Jul. 21, 2017, and assigned to the same assignee as the present application, which application is incorporated by reference into the present disclosure.

A radiation source may be operated such that it delivers radiation energy of the desired disinfecting wavelengths at a constant or otherwise controlled rate measured in Joules/second (i.e., Watts), or some other unit of measure, and delivers radiation energy for a selected or selectable amount of time (e.g., seconds) to achieve the selected radiation dose. In the study of photonics and radiation, it is known to define a reference area in meters squared ($m^2$) or centimeters squared ($cm^2$) upon which the radiation impinges, or through which it passes. In these courses of study, the power level per unit area, or irradiance, which is sometimes also called "fluence," is defined in Watts/$cm^2$. In such embodiments, for example, the target article can be irradiated directly from one direction, such as above, with incident radiant energy measured at the plane of the target article substrate. The conditions required to achieve a certain logarithmic reduction in the population of viable pathogen(s) being evaluated provide starting conditions for setting the system parameters and disinfection cycle times for the disinfection systems described herein. Using such information, the disinfection cycle conditions are then confirmed in the actual disinfection system via one or more test runs with test articles which are inoculated, disinfected, and then assayed to determine disinfection efficacy. Depending on the results achieved with the starting conditions to obtain the desired disinfection, target dose and other conditions can be adjusted to achieve the desired level of disinfection (i.e., the minimum required dose to all surfaces intended for disinfection), without needlessly risking overexposure of the target article to the disinfecting conditions.

The devices and systems described herein may be configured to allow calibration of the one or more sources of disinfecting radiation and/or the one or more detectors of disinfecting radiation. For example, in some cases, the disinfection chamber may be configured to allow for placement of one or more calibrating sensors and additionally or alternatively one or more calibration articles that emulates an actual target device. In these cases, an assessment of the real time irradiance level and/or total dose of disinfecting radiation energy (i.e., the integral of the radiant power over time) delivered to one or more regions within the chamber or one or more surface portions of a target calibration article can be made.

As discussed in the present disclosure, the interior volume of a disinfection chamber may be modeled, and the surface of a target article to be disinfected (e.g., a medical probe or other medical device, a calibration device, or any other such object) may also be modeled. In addition, a first radiation map of the interior volume of the disinfection chamber may be generated by operating the disinfection device (i.e., irradiating the interior volume of a disinfection chamber) while collecting sensor data during defined test operations. A second radiation map of the interior volume of a disinfection chamber may also be generated when the test article is placed in the interior volume of a disinfection chamber when sensor data is collected. The first and second radiation maps may be considered as "measured radiation maps" because they represent radiation collected from the interior volume of the disinfection chamber by actual electronic sensors.

Subsequently, data from the modeled disinfection chamber and the modeled target article can be combined to determine a modeled radiation map. The modeled radiation map may be adjusted one or more times based on one or both of the first and second measured radiation maps. Alternatively, or in addition, parameters of the disinfection cycle can be adjusted to achieve an acceptable confidence that the one or more modeled radiation maps represents an actual radiation dose delivered in an interior volume of an actual disinfection chamber when an actual test article is present.

The combinations, calculations, and analysis described herein, may be iterative and carried out over time, and may be repeated to improve accuracy. The combinations, calculations, and analysis can be used to generate any number of disinfection programs for any number of test articles. That is, the interior volume of any type of disinfection chamber may be modeled, and the surface of any type of target article for disinfection may be modeled. Information from the models may be used to generate a disinfection program that can be loaded into and executed by an actual disinfection device of the given (i.e., modeled) type to disinfect a target article of the given (i.e., modeled) type. In some cases, the generation of models and disinfection program may even occur in real time. By applying the processes and techniques of the present disclosure, the modeled data can be relied on, and the need for laborious measurements may be reduced or avoided.

Note that readings provided by the one or more calibrating or other sensors can be used to adjust system target dose, which in turn may impact cycle times, to provide delivery of a desired minimum dose of disinfecting radiation energy. These earlier collected readings may also be used to adjust parameters in a generated program algorithm such that readings obtained in real time from a given sensor during an actual disinfection cycle are weighted differently. That is, when earlier measured or modeled data does not match data collected in real time, the earlier data may be used to adjust one or more parameters used in the algorithm that accounts for degradation (e.g., predicted degradation) of the radiation source, change in output over time/use of radiation sensors, or other characteristics of the disinfection chamber that may evolve with time or use.

In some cases, to assist with calibration or actual disinfection, the disinfection chamber may employ one or more means of reliably and consistently locating a test article within the interior volume of the disinfection chamber. Reliable and consistent locating of the test article may include placing the test article in the disinfection chamber a same way each time within an acceptable tolerance. Placing the test article in the disinfection chamber in the same way each time may include any one or more of a same height, same depth, same dimensional orientation, same pre-cleaning, and any other such discernible features.

The means to reliably and consistently locate a test article within the interior volume of the disinfection chamber may include physical registration indicia (e.g., protuberances, apertures, mating surfaces, visual alignment marks or cues, or the like). Such means may additionally or alternatively include other registration indicia structures such as electronic circuits that provide visual, audio, tactile, or other feedback upon proper or improper placement. And such means may also include magnetic structures that are biased to attract proper placement and/or biased to repel improper placement. These means (i.e., the physical, virtual, electronic, magnetic, or other registration indicia) facilitate proper locating of the test article within the interior volume of the disinfection chamber.

One embodiment of a disinfection device method may be summarized as including acts of: providing a disinfection chamber having an interior volume and a radiation source, wherein the radiation source emits ultraviolet-C (UV-C) radiation into the interior volume when in operation; identifying a UV-C radiation emitting characteristic of the radiation source; identifying a structural configuration of the interior volume; estimating a UV-C radiation intensity map within the interior volume based on the UV-C radiation emitting characteristic and the structural configuration of the interior volume; determining a disinfection exposure of a target article based on the UV-C radiation intensity map; and confirming the disinfection exposure by actual measurements, which may be adjusted by one or more calibration values.

One embodiment of a non-transitory computer readable storage medium may be summarized as containing executable instructions which, when executed by a processor, configure the processor to operate a disinfection system, wherein the acts of the operation: identify a disinfection chamber having an interior volume and a radiation source coupled to the interior volume, the radiation source emitting ultraviolet-C (UV-C) radiation into the interior volume when in operation; determine a UV-C radiation emitting characteristic of the radiation source; receive a structural configuration of the interior volume; receive a surface characteristic of an target article; estimate a UV-C radiation intensity map within the interior volume based on the UV-C radiation emitting characteristic, the structural configuration of the interior volume, and at least one surface characteristic of the target article; and determine a disinfection exposure of the target article based on the UV-C radiation intensity map.

One embodiment of a disinfection system may be summarized as including a disinfection chamber having an interior volume; a radiation source coupled to the interior volume, the radiation source arranged to emit ultraviolet-C (UV-C) radiation into the interior volume when in operation; and a control system configured to carry out a plurality of expressly recited acts. The expressly recited acts include acts to: identify a structural configuration of the interior volume; receive a surface characteristic of a target article (e.g., a type of target article, location of the target article, position of the target article, reflectance of one or more surfaces of the target article, pre-cleaning or dirtiness of the target article, or some other characteristic); estimate a UV-C radiation intensity map within the interior volume based on the UV-C radiation emitting characteristic, the structural configuration of the interior volume, and a selected surface characteristic of the target article; and determine a disinfection exposure of the target article based on the UV-C radiation intensity map.

Devices, systems, and methods for controlling disinfection exposure on target articles are disclosed herein. The devices, methods, and systems provided are well-suited to the disinfection of medical devices, such as, for example, medical devices classified by the CDC as critical or semi-critical items. Articles processed using the technique described herein may or may not be connected or tethered to another device, system, or component. For example, in the context of a medical device, embodiments of the technique described herein are suited to the disinfection of ultrasound probes. Currently, many ultrasound probes are tethered to a central processing unit, a display, etc., by one or more cables that provide, for example, power or data communication capabilities to the probe. However, a wireless ultrasound probe need not be tethered to a device, system, or component. The devices, systems, and methods described herein are suited to and can be adapted to accommodate tethered (e.g., wired) devices and untethered (e.g., wireless) devices. In addition, or in the alternative, to standalone disinfection devices, the devices, systems, and methods for controlling disinfection exposure on target articles disclosed herein may also be integrated into, or otherwise associated with, another system or device such as an ultrasound system.

According to an embodiment, target articles subjected to a disinfection cycle as provided by the methods, devices, and systems described herein receive high-level disinfection. As used herein, "high-level disinfection" and "HLD" refer to a process sufficient to provide a log reduction in viability of at least $10^5$ of one or more specified microorganisms on a target article. As used in the present disclosure, HLD generally means rendering a pathogen unable to infect (i.e., replicate, grow, and thus potentially affect negatively some other host entity). Disinfection systems as described herein do not necessarily "kill" the pathogen or remove the remains of the pathogen. Instead, the disinfecting systems may operate to disrupt the pathogen at the molecular level such that the pathogen is rendered impotent or "static." The pathogen may remain "alive" and physically present, but unable to reproduce.

HLD disinfection procedures are sufficient to provide log reductions in viability of one or more specified microorganisms of between about $10^4$ to about $10^6$, and in certain embodiments, "high-level disinfection" disinfection procedures provide a log reduction in one or more specified microorganisms of greater than $10^6$ viable organisms on the article. However, in some instances, the disinfection cycles disclosed herein are sufficient to achieve at least a $10^6$ log reduction of a microorganism on the target article. The required reduction in the amount of viable microorganisms that remain on the test article post-disinfection may vary according to the level of disinfection needed or otherwise desired, and the level of disinfection provided can be adjusted by varying or adjusting the parameters of the disinfection cycle.

II. Devices & Systems

FIG. 1 shows a disinfection system 100 in an operation environment 10. As shown in FIG. 1, system 100 includes a disinfection chamber 110 having an interior volume 112. One or more radiation sources 120 are coupled to the interior volume 112 and emit radiation light rays into interior volume 112 when in operation. One or more sensors 130, 132 are physically, communicatively, electronically, or otherwise coupled within interior volume 112 and arranged to detect radiation and other such parameters (e.g., intensity, time, volume, and the like) within interior volume 112. The one or more sensors 130, 132 may be arranged in a manner specifically for a type of target article 240 (FIG. 2B) to be disinfected in disinfection chamber 110. For example, sensors 130 may be arranged in a manner suitable for detecting radiation intensity information on the surface portions of a target article.

In the present disclosure, sensors arranged to detect disinfection radiation are referred to herein as sensors 130. In contrast, sensors arranged to detect other non-disinfection-radiation phenomena, such as temperature, time, vibration, weight, humidity, liquid, continuity, and the like, are referred to herein as sensors 132. Accordingly, in addition to one or more sensors 130 (e.g., photodiodes) capable of detecting or quantifying the disinfecting intensity delivered within the interior volume 112 and to the target article 240 to be disinfected, the disinfection chamber 110 may also include one or more temperature sensors, one or more foreign object detection sensors (e.g., infrared emitters and detectors, cameras, accelerometers, load cells, or the like), one or more "door open" sensors (e.g., normally-open or normally closed switches, light detectors, continuity circuits, or the like), or any other types of non-disinfection-radiation sensors. These other, non-disinfection-radiation sensors may each, individually or collectively, be referred to as sensors 132.

One or more of disinfection chambers 110, radiation sources 120, and sensors 130, 132 are communicatively coupled to a controller 140. Controller 140 includes a disinfection exposure determination unit 142 and a disinfection operation control unit 144 arranged to execute a generated disinfection program. Besides the data exchange with disinfection chamber 110, radiation sources 120, and sensors 130, 132, controller 140 may also communicate with one or more databases 150 and/or disinfection requirement inputs 160 in achieving its functions and operations.

Figure 2:
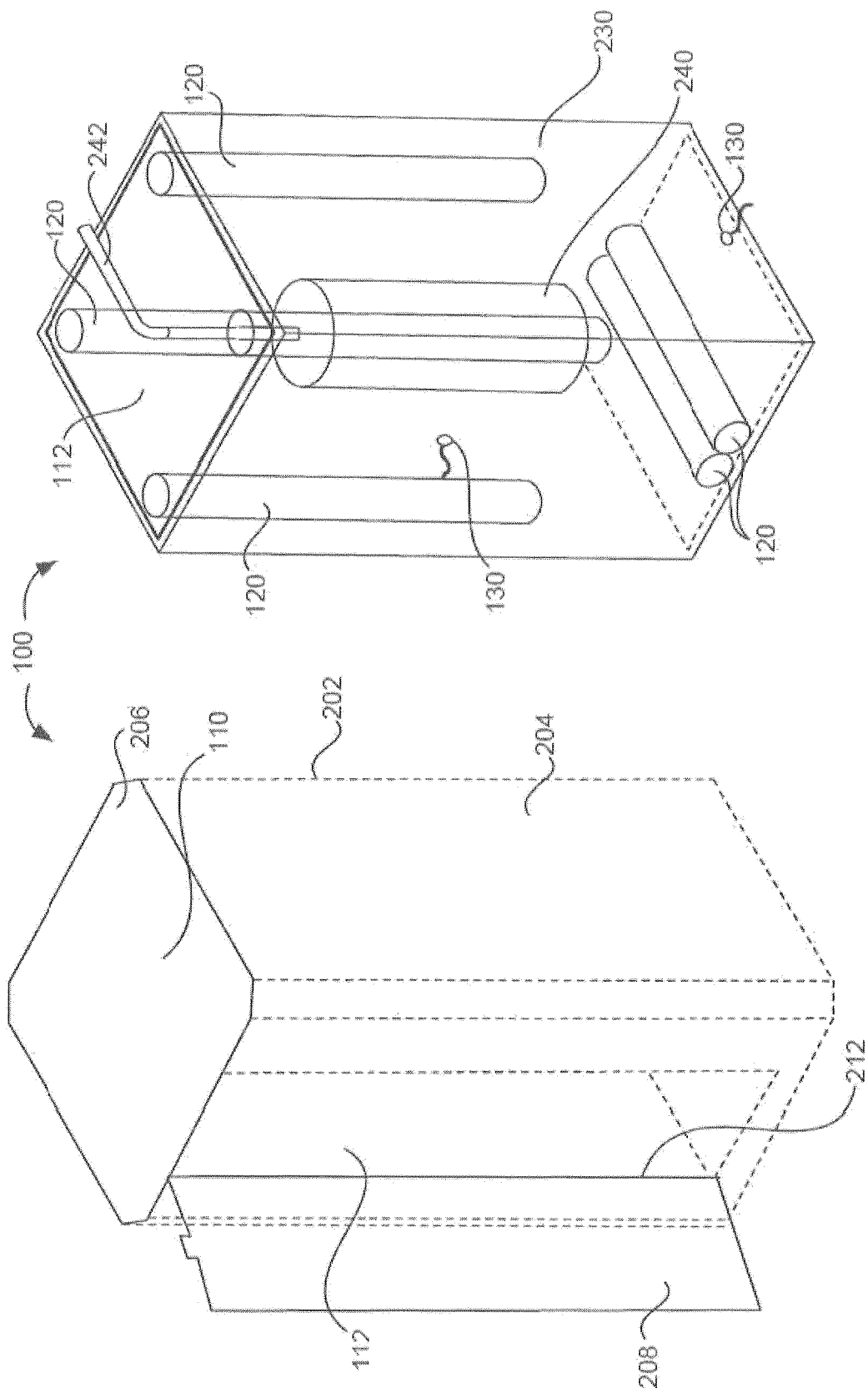
FIGS. 2A-2B show exemplary disinfection chambers, each of which may be referred to as an example system (FIGS. 2A-2B may be collectively referred to herein as FIG. 2)

FIGS. 2A and 2B show exemplary disinfection chambers, each of which may be referred to as an exemplary disinfection system 100. FIGS. 2A and 2B may be referred to collectively as FIG. 2. In FIG. 2, disinfection system 100 is a high-level disinfection device that includes a disinfection chamber 110 and one or more radiation sources 120. Disinfection chamber 110 includes a housing 202 having a plurality of sidewalls 204, a top 206, and a door 208 disposed within one of the sidewalls 204 for accessing the interior volume 112. Although the door 208 in FIG. 2A is shown as being rotatably movable about a vertical axis, other door configurations may be used, so long as they provide adequate access to the interior volume 112. It is understood that upon opening door 208, an access opening 212 is created in the disinfection chamber sidewall 204, and the access opening 212 communicates with the interior volume 112. Other arrangements of disinfection chambers are of course contemplated.

The interior volume 112 of the disinfection chamber 110 may include one or more reflective surfaces 230 arranged to facilitate reflections of radiation light rays emitted from radiation sources 120 such that a rapid and low temperature disinfection is achieved. The reflective surface is typically formed from one or more materials having at least 30% reflectivity. By "at least 30% reflectivity," it is meant that no more than 70% of the incident UV radiation, particularly in the UV-C range, will be absorbed, and the rest of the incident radiation will be reflected via one or both diffuse and specular reflection. Reflective materials that may be particularly useful in a disinfection chamber include, but are not limited to, aluminum, glass, magnesium, stainless steel, polyvinyl alcohol, polytetrafluoroethylene, substrate materials treated with barium sulfate-containing paints, and alloys, derivatives, and copolymers thereof. In some variations, the reflective surface comprises aluminum, polished to a "Grand Brilliant" condition. In other variations, the reflective surface may be formed using polytetrafluoroethylene PTFE, or PTFE and similar polymers may be coated by various means onto another substrate, to form the reflective surface. In particular embodiments, the reflective interior surfaces of the disinfection chamber are formed to be as reflective as available manufacturing techniques provide. Such an approach facilitates disinfection processes that utilize high intensity disinfection radiation carried out at low temperatures.

The interior surfaces 230 of the interior volume 112 may be positioned and shaped to reduce the absorption of UV radiation by the interior surfaces 230 and instead reflect and redirect the UV radiation within the interior volume 112 of disinfection chamber 110 and onto the one or more target articles 240 positioned within the interior volume 112. The material choice and configuration of the interior volume 112 of disinfection chamber 110 may be selected to promote preferential extinction of certain UV or other wavelengths of electromagnetic energy that can contribute to increased temperatures within the interior volume 112 (i.e., longer wavelengths of radiation). That is, the shape of the interior volume 112 may contribute to the quick and efficient directing of radiation to the target article 240. For example, it may be configured that the radiation passing through the middle of the interior volume 112 of the disinfection chamber 110, where the target article 240 is to be positioned, and the reflective material(s) employed in the interior volume 112 may contribute to the reflection (e.g., re-radiation or re-emission) of radiation with low loss (i.e., approximately the same amount of energy returns from the surface as was incident). In particular embodiments, the interior walls of the interior volume 112 are constructed and configured to provide low loss of UV-C radiation emitted from the one or more UV radiation sources 120 (not specifically shown in FIG. 2A for simplicity purposes). Such embodiments increase the likelihood that UV-C radiation useful for disinfection will be reflected one or more times inside the chamber until the radiation impinges upon the article to be disinfected where it may be absorbed and extinguished, reflected, or re-emitted. In this way, for a given amount of total energy released into the chamber, which also may include some amount of infrared or heat energy, an improved utility is made of the useful UV-C band energy in disinfecting the target article 240, e.g., medical device or instrument, while reducing the amount of thermal heating of the target article 240.

As detailed herein, the disinfecting radiation utilized can be UV-C radiation, and in embodiments that utilize UV-C radiation, the one or more radiation sources 120 may be any commercially available device suitable for emitting sufficient UV-C radiation to carry out high-level disinfection. Where one source 120 of UV-C radiation is coupled to the disinfection chamber 110, that source 120 will emit sufficient UV-C radiation to carry out high-level disinfection as detailed herein. Where two or more sources of UV-C radiation are coupled to the disinfection chamber 110, the UV-C radiation sources 120 may each be capable of emitting sufficient UV-C radiation to carry out high-level disinfection. Alternatively, in embodiments of the system 100 including two or more UV-C sources 120 coupled to interior volume 112 of disinfection chamber 110, such radiation sources 120 may each, on their own, emit insufficient UV-C radiation to achieve high-level disinfection, but when the individual outputs of UV-C radiation emitted from the two or more sources 120 are combined, the total output of UV-C radiation is sufficient to achieve high-level disinfection.

Radiation source 120 may be coupled to interior volume 112 through various approaches. For example, radiation source 120 may be locally attached to interior volume 112 to emit UV-C radiation rays into interior volume 112, as shown in FIG. 2B for illustrative purposes. In further examples, a radiation source 120 may be remotely coupled to interior volume 112. For example, radiation source 120 may be a standard laser, or solid state laser photodiode, and may be employed as a source of disinfecting energy for a stand-alone disinfection chamber 110, along with appropriate optical conductors and couplers to emit UV-C radiation rays into interior volume 112. Further, in some embodiments, a direct or conducted source of UV radiation could be steered, via a mirror or other device, or scanned along a target article 240 positioned within interior volume 112. In other embodiments, disinfection chamber 110 may include a moveable attachment assembly, which is not specifically shown to avoid unnecessarily cluttering the figure, within interior volume 112 such that a target article 240 may be positioned on the moveable base and may be moved past a stationary radiation emission region. Controller 140 may control the radiation source 120 and the moveable base to rotate or move in opposite directions to provide preferential exposure of the target article 240 to the UV radiation.

Though the devices, methods, and systems provided herein are primarily described with reference to UV-C radiation as the disinfecting radiation within the disinfection chamber, this is for illustrative purposes only. The radiation or energy used in the disinfection system 100 may also be or include UV-A radiation, UV-B radiation, or even non-UV radiation, alone or in various combinations. It is to be further understood that, within the interior volume 112, exposure of the articles to UV radiation may be carried out in a variety of ways.

Instead of UV radiation, such as UV-C radiation, some variations of the devices described herein may use a flash source of energy. A flash source of energy emits extremely high intensity disinfecting radiation. The flash source of energy can provide high-level disinfection of one or more contaminated articles in an acceptably short period of time. In certain embodiments, a flash source of energy may deliver disinfecting radiation to the one or more articles at such a high rate that high-level disinfection is achieved in period of time selected from 10 seconds or less, 5 seconds or less, 3 seconds or less, and 2 seconds or less. A flash source of energy as contemplated herein may be selected to deliver any selected disinfecting radiation. For instance, a disinfection system as described herein may include a flash source of energy that emits electron beam, gamma-ray, x-ray, gas-plasma, or UV-C radiation. The biologically active mechanism of disinfection of the flash source may be different for the different sources. For example gamma-ray may fully kill a pathogen, whereas UV-C may leave the pathogen alive but biologically sterile and unable to reproduce.

Where a flash source of energy is used, one radiation source 120 of disinfecting radiation may be all that is needed in the interior volume 112 of disinfection chamber 110. In such embodiments, to achieve generally homogenous or uniform radiation exposure on the target article 240, the radiation emitted by the flash source may first strike a surface that will spread and distribute the radiation before hitting the target. In this case, the target will receive primarily indirect rather than direct, illumination. In other words, the disinfection device could be configured so that the source or sources, of any appropriate type, are located in a different part of the device than the target. Since the energy spectrum emitted by some types of flash sources may be broad, it may be helpful to interpose a filter between the source and the target so only the spectrum of interest is allowed to pass to the disinfection chamber. The filter may serve to minimize the presence within the chamber of infrared energy, which does not disinfect but will otherwise heat the chamber and thus raise its temperature and that of objects contained therein. Said filters may also be useful when implemented with the other radiation sources mentioned herein. Combinations of disinfection energy sources may be used in the devices and systems described herein. Where two or more different disinfection energy sources are used, they may be applied sequentially, in parallel, or in various combinations and orders. The inclusion and use of two or more different sources of disinfecting energy may prove advantageous in situations where certain pathogens are more susceptible to a particular source of disinfection energy, and in order to reduce overall exposure of the target article 240, it may be useful to employ a variety of radiations sources, durations, and doses to achieve acceptable disinfection for pathogens of interest.

Where the devices and systems described herein utilize UV radiation, such as UV-C radiation, the one or more UV radiation sources 120 and/or the one or more UV radiation sensors 130 are positioned within the interior volume 112 of disinfection chamber 110 in a manner that facilitates rapid, low temperature disinfection. In general, the configuration of the disinfection chamber, the sources of disinfecting radiation, and the sensors detecting disinfecting radiation will be selected to provide and confirm a selected exposure of the one or more articles to radiation and/or optimize transmission of radiation from the one or more sources to efficiently and reproducibly target an article.

As described, a disinfection chamber 110 according to the present description may be coupled to a single radiation source 120 of disinfecting radiation, such as one UV-C radiation source. In such embodiments, the radiation source may be positioned on a top or bottom of the chamber. Alternatively, depending on the positioning of the articles to be disinfected, the single radiation source 120 may be positioned on a side of the disinfection chamber or, where the disinfection chamber includes multiple sides, at an intersection formed at an intersection of two sides. However, the devices and systems described herein are not limited to disinfection chambers having a single source of disinfecting radiation.

The disinfection chamber 110 included in the devices and systems 100 according to the present description may utilize multiple radiation sources 120, of the same or different variety, and different embodiments of a disinfection chamber 100 having multiple sources 120 of disinfecting radiation are detailed herein and illustrated in the accompanying figures. Such embodiments may be advantageous where the surface of the one or more target articles 240 to be disinfected are more complex than a single flat surface. For example, a target article 240 to be disinfected, such as an endotracheal probe or an ultrasound probe, may have two or more of a front, back, lateral, and dorsal and/or ventral surface that require disinfection. In such a scenario, it may be difficult to deliver high intensity radiation to each surface of target article 240 with a single source or type of disinfecting radiation. Accordingly, in some embodiments of the disinfection devices 100 described herein, the radiation sources 120, and other structures are arranged to disinfect one particular type of target. That is, the sources 120 and/or other structures may provide illumination to each surface of the specific target, but the device would not function effectively if a different type of target was placed in the disinfection chamber.

Radiation sources 120 that may be employed in devices and systems as described herein are available in the art, and include, for example, UV-C emitting lamps. UV-C emitting lamps, also referred to herein as "tubes," are available commercially from various sources, including Philips Lighting B.V., and can be obtained in different shapes, sizes, input energy, and UV-C output ratings. Suitable UV-C tubes for use as a UV-C energy source include low-pressure mercury vapor discharge lamps. However, the disinfection chambers are not limited to a particular UV-C source. Any source capable of emitting UV-C light within the selected UV-C wavelength at an output rating that contributes to the disinfection of a target article 240 could be used in the devices disclosed herein. For example, in addition to or as an alternative to one or more UV-C tubes, one or more lasers or photodiodes, or arrays of sources, or combinations of types of sources designed to emit UV-C light may be used to deliver disinfecting radiation within the disinfecting chamber.

In particular embodiments, the one or more sources of UV-C radiation included in the disinfection chambers 110 described herein provide a total UV-C output within the interior volume 112 of the disinfection chamber 110 that is selected to be at least 5 Watts of radiant power. Selection of such a radiation source, which can deliver a high-power dose of radiation, may be preferred to shorten a disinfection cycle. That is, by selecting a high-power radiation source, the energy is delivered rapidly, which may reduce the duration of radiation exposure and also reduce the amount of heat generated by the radiation. In other cases, the one or more radiation sources 120 may be selected to provide a total UV-C output within the chamber's interior volume 112 selected from at least 10 W, at least 15 W, at least 20 W, at least 25 W, at least 30 W, at least 40 W, at least 50 W, at least 75 W, at least 90 W, and at least 100 W of radiant power. Where UV-C sources are used as the one or more sources 120 of disinfecting radiation, the frequency band of UV-C light emitted from the one or more sources may be selected from between about 240 nm and about 270 nm and between about 255 nm and about 265 nm.

Figure 3:
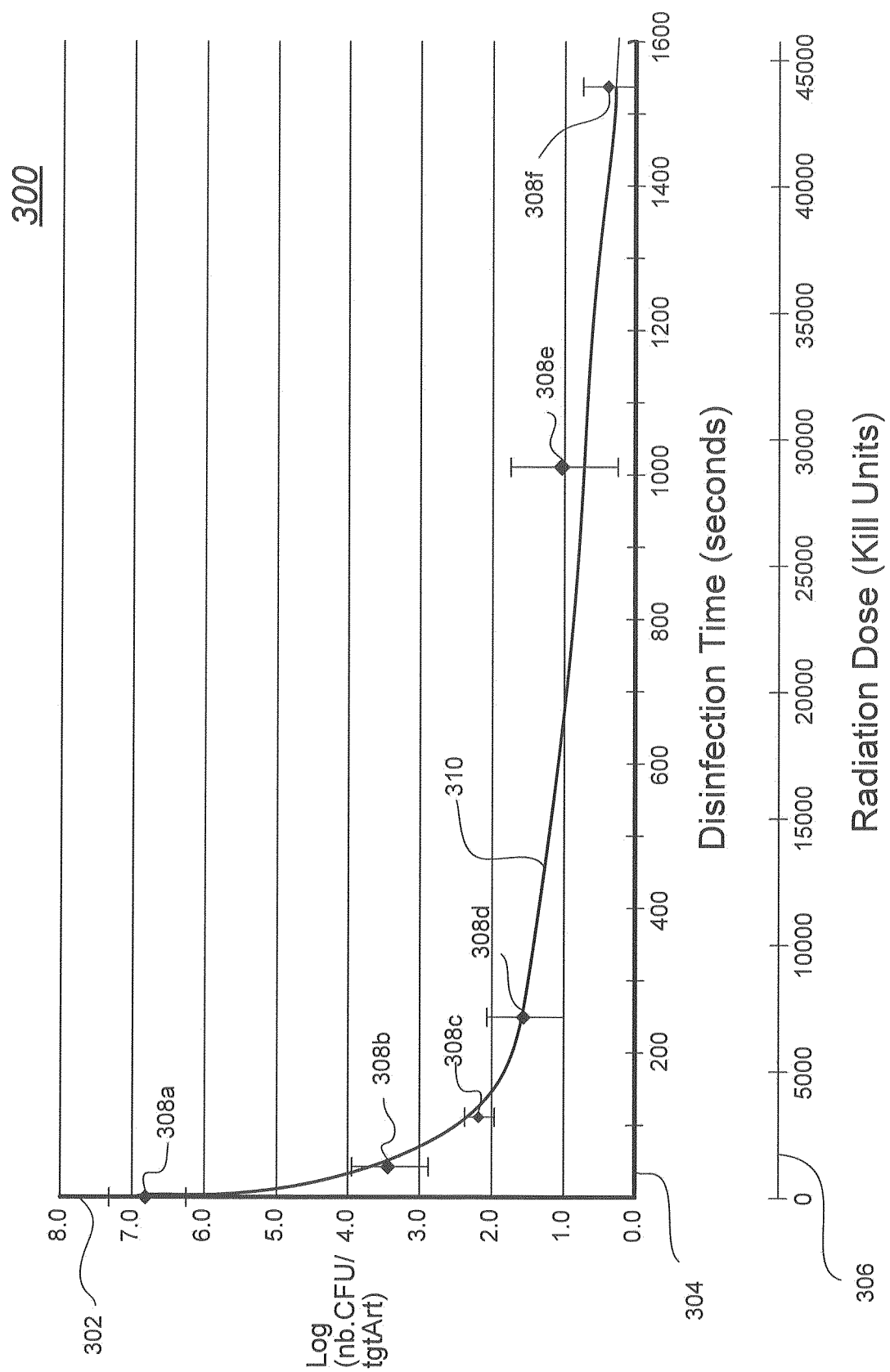
FIG. 3 is an exemplary kill curve.

FIG. 3 is an exemplary kill curve 300. To facilitate the discussion of kill curve 300 of FIG. 3 and the understanding of a target dose of radiation, certain concepts are now explained. One such concept is the principle of proportionality of energy fluence ratios. Energy Fluence Rate may be understood by those of skill in the art as the flow of energy in watts per square meter (Watts/m$^2$), which in the present disclosure is photonic energy in the UV wavelength range, coming from all directions through or across an infinitesimally small sphere of unit area (1) within the interior volume 112 of the disinfection chamber 110. Integrating this energy flow over this surface and over time calculates a "dose" in Joules (J) that has been delivered from the radiation sources 120 and delivered, presumably, at the surface of the target article 240. This energy may be absorbed and extinguished, re-emitted, reflected/scattered, or captured and transported elsewhere. At a given point or elemental surface in the disinfection chamber 110, the dose of energy delivered to the point or surface is the integral (i.e., summation) of the irradiance over the total exposure. Another related term, irradiance, in W/m2, is used, and in a situation where all inbound radiation is coming from a single direction and impinging onto a surface, irradiance and fluence are identical. Fluence takes into account that the radiation may be inbound and reach a surface from many directions, which is the case in the disinfection chamber 110 of the present disclosure due to one or more radiation sources 120 and an interior volume 112 with one or more reflective surfaces. The radiation is broadly distributed as an illuminating field of photonic power with the intention of fully exposing all surfaces of a target article contained within the disinfection chamber 110.

In the present disclosure, the terms "fluence" and "irradiance" may be used interchangeably, although it is recognized that amongst the two terms, there are differences. The present disclosure, in at least some embodiments, is concerned with radiation impinging on an elemental unit of surface from one side, entering from a hemisphere of angle. That is, radiation is not reaching the surface from the rear as it is blocked by the target object. Inbound radiation can impinge on the surface substantially normal (i.e., perpendicular) to the surface element, as well as at all other angles of incidence up to +/−90°. Depending on the field of view of the radiation collection optics at the front of a detector, a broad or narrow range of angles of inbound radiation may be suitable sampled. When the angle is narrow, fluence is essentially identical to irradiance.

When monitoring radiative power in a disinfecting system, it may be useful or expeditious and simpler to collect narrow angle incident radiation. When measuring radiative power at a location within the chamber to assess the amount of total (e.g., aggregated) energy impinging on a surface, a detector with a very wide angle of acceptance may be selected. Further, inlet optics on detectors may be fitted with filters to permit passage and thus measurement only of radiation of the desired disinfecting wavelength. This information is then incorporated into the algorithms and models when correcting the predicted fluence levels with those measured in the chamber or at the surface of a test device.

By characterizing the disinfection system 100 and a given target article 240, a "target article ratio" can be established between the radiation dose received at a specific point (e.g., a region of interest such as a determined "cold spot") on the target article 240 and the average dose measured by sensors 130 inside the interior volume 112 of the disinfection chamber 110. The proportionality of irradiance ratios in the disinfection chamber 110 are then used to adjust (e.g., increase or decrease) a base radiation dose that would acceptably disinfect a standard surface (e.g., a test carrier inoculated with a known amount of a particular pathogen, distributed over a defined surface, during disinfectant potency testing) to a determined confidence level that a sufficient dose of radiation is received at the surface of the target article 240 (e.g., an ultrasound probe) intended for disinfection.

Disinfection of target article 240 placed in the center of the disinfection chamber 110 is achieved when the surfaces of the target article 240 that are intended for disinfection actually receive sufficient fluence to achieve high-level disinfection (i.e., a desired log reduction of viable pathogen). The value of the fluence received at each point on the target article's surface at a particular point in time, which may be time varying, and which may be constant or remain within an acceptable range during a specified time interval, may be measured by optical instrumentation and a discrete step-wise mapping process. Embodiments of the disinfection system 100 have been characterized by such mapping where irradiance levels were measured at multiple locations. This mapping provides confirmation of the incoming radiation arriving at locations where the surfaces of particular target articles 240 (e.g., ultrasound probes) would be positioned. Further, computer simulation modeling of the disinfection chamber 110, radiation sources 120, and including the presence of a modeled target article permit calculation of the theoretical irradiance at a selected location. In testing by the inventors, these simulated radiation levels have been compared to actual measurements and found to be in good agreement.

In FIG. 3, the results of at least one study of effectiveness of the disinfection system 100 discussed in the present disclosure are illustrated. The inventors have performed detailed and extensive testing of such effectiveness against a number of pathogens including *Bacillus subtilis*, *Clostridium sporogenes*, and many others. Exemplary results are presented in FIG. 3, and the exact spore represented by the kill curve 300 is not relevant to the discussion. Instead, the teaching of FIG. 3 illustrates that the radiation used in the present disinfection systems kills very rapidly early in the disinfection cycle as the pathogen is directly impinged upon by the radiation. As time passes, killing off the last 2 logs of viable pathogen survivors may require extension of the disinfection cycle. One theory for this is that the pathogen entities neutralized early in the disinfection cycle physically shield surviving pathogen spores from at least some inbound radiation. Neutralizing these remaining survivors that are "buried" beneath the earliest affected spores requires longer radiation exposure.

In FIG. 3, a vertical axis 302 is a logarithmic representation of a number of viable pathogen spores present in a determined area of a target article (i.e., a negative binomial distribution of colony forming units (nb.CFU)) per target article 240 (tgtArt). A first horizontal axis 304 represents an elapse of time (e.g., a disinfection cycle duration) over which a disinfection cycle is performed. The first horizontal axis 304 is measured in seconds, but other time units could also have been selected.

A second horizontal axis 306 of the kill curve 300 in FIG. 3, which is below the first horizontal axis 304, represents an accumulation of radiation dose (e.g., energy fluence integrated over the exposure) delivered to a surface of target article 240 during a disinfection cycle. The accumulation of radiation is generally linear over time in FIG. 3, but it is recognized that other disinfection programs may alter the delivery of radiation in any way, which could change the distribution of energy fluence over time. The measure of radiation dose in FIG. 3 is disinfection or "kill units," which is purposefully a non-limiting, non-standard unit chosen for the exemplary illustration. The disinfecting action of a type of radiation may sterilize a pathogen leaving it alive but non-viable, which at least in the present disclosure means that it cannot reproduce. Hence the pathogen is disinfected, but not necessarily "dead." Within the present disclosure, the term kill unit (KU), may be understood as an accumulation of "counts" that describes the overall radiation exposure delivered in the interior volume 112 of the disinfection chamber 110 over a given cycle. On a periodic schedule (e.g., 300 milliseconds), data signals from sensors 130 (e.g., photodiodes) are read. These values may be corrected by one or more calibration factors and summed over the course of the radiation exposure using, for example, the controller 140. Accordingly, it is understood that for any given disinfection chamber 110, radiation source 120 or sources 120, sensor 130 or sensors 130, and the like, a determined amount of radiation (e.g., a total amount of radiation to a selected surface in Joules, or in some cases, an area-specific dose in e.g., Joules/cm$^2$) may be measured, calculated, or otherwise determined. In FIG. 3, however, which is not limited to any particular disinfection chamber 110, radiation sources 120, or sensors 130, the term, kill units, has been selected to convey the relevant teaching of FIG. 3.

Also in FIG. 3, various viable pathogen measurements 308a-308f are represented. The fitted curve 310 represents the amount of viable pathogen remaining during the disinfection cycle. Accordingly, kill curve 300 may sometimes also be referred to in the art as a "survivor curve."

As evident in FIG. 3, one reason to deliver a high-power dose of radiation is to shorten a disinfection cycle time. This is because radiation very rapidly kills/disinfects a substantial portion of the pathogen early in the disinfection cycle. By applying radiation at high power levels, the energy can be delivered quickly, which can shorten the disinfection cycle time. This has the added advantage of reduced opportunity for thermal heating of the target article 240. In FIG. 3, a mean 5 log 10 reduction of pathogen is achieved in the first 150 seconds via delivery of about 5000 KU, and a mean 6 log 10 reduction of viable pathogen is achieved in after only 650 seconds and delivery of about 9300 KU.

Certain notable findings were made during testing, some of which are represented in FIG. 3. First, disinfection via UV radiation displays an extremely "front loaded" kill curve with the majority of the germicidal effect occurring in the first tens of seconds of exposure. Second, no additional growth of pathogen was observed on the target article 240 after being irradiated even when the target article 240 was first heavily inoculated with the pathogen (i.e., 7×10$^6$ spores). Third, in addition to rapidly reducing the pathogen population to a low level, the disinfection system 110 is also effective at killing a large percentage of viable pathogen spores on a target article 240. And fourth, as evident after 1600 seconds, a very small number of viable pathogen spores may still survive the disinfecting radiation dose (e.g., measurement 308f). In the limit of a very long exposure, disinfection becomes "sterilization," which is where no viable entities remain.

Turning back to FIG. 2, each radiation source 120 may emit radiation light rays according to its own parameters and characteristics. For example, the age of a radiation source 120 may be directly related to the light emitting characteristic thereof. Further, the time lapse after a radiation source is turned on may also affect the UV-C radiation emitted from the radiation source 120. For example, the intensity of radiation light emitted by a radiation source 120 may, as part of its natural operation, be time dependent and may include a specific pattern of waveform/variations, e.g., continuous decreasing, continuous increasing, or fluctuating. Further, each radiation source 120 may include different operation states of emitting the radiated light. For example, each radiation source 120 may have characteristics that cause the respective source to radiate at different power levels even when the output power of two or more radiation sources 120 is otherwise expected to be the same. Each radiation source 120 may also emit radiation light rays at different angles, substantially parallel to each other, or a combination of attitudes in operation. And a plurality of radiation sources may be controlled with common signals and common parameters. Alternatively, two or more radiation sources may be independently controlled via independent control signals and parameters.

A disinfection chamber 110 as described herein may be configured to create a plurality of disinfection regions within the interior volume 112. In such embodiments, the disinfection chamber 110 and/or one or more target articles 240 to be disinfected can be further configured such that the one or more target articles 240 to be disinfected are positioned within the disinfection regions in selected positions, alignments, orientations, or the like. As used herein, the term "disinfection region" refers to a region within the disinfection chamber wherein a certain intensity of disinfecting radiation is delivered over the course of a disinfection operation. In specific embodiments, the interior volume 112 is coupled to one or more sources 120 of UV-C radiation, and the one or more sources 120 of UV-C radiation are selected and arranged to deliver, independently or in common, UV-C radiation to the disinfecting regions at a varying radiation intensity, namely irradiance (also referred to as "power" to or through a specific unit of area) of, e.g., at least about 1,500 µW/cm². In this way, via the plurality of disinfection regions and the independent or common control of radiation sources, more precise delivery of radiation may be possible within the interior volume 112 of the respective chamber.

In some embodiments, the one or more radiation sources 120 of UV-C radiation may be selected to emit UV-C light within a band selected from between about 240 nm and about 270 nm and between about 255 nm and about 265 nm. For example, one or more UV-C source(s) 120 may be selected and arranged such that one or more disinfection regions are formed within the disinfection chamber, and the radiation intensity ("irradiance") of the UV-C radiation delivered to the one or more disinfecting regions is between about 1,500 µW/cm² and about 5,000 µW/cm². In further embodiments, the one or more UV-C source(s) 120 may be selected and arranged to provide one or more disinfecting regions wherein the irradiance of the UV-C radiation delivered within the disinfection region(s) is selected from between about 1,500 µW/cm² and about 2,000 µW/cm², between about 1,500 µW/cm² and about 2,500 µW/cm², between about 1,500 µW/cm² and about 3,000 µW/cm², between about 2,000 µW/cm² and about 2,500 µW/cm², between about 2,000 µW/cm² and about 3,000 µW/cm², between about 2,000 µW/cm² and about 3,500 µW/cm², between about 2,000 µW/cm² and about 2,500 µW/cm², between about 2,000 µW/cm² and about 2,750 µW/cm², between about 2,500 µW/cm² and about 2,600 µW/cm², between about 2,500 µW/cm² and about 2,750 µW/cm², and between about 2,500 µW/cm² and about 3,000 µW/cm², or between other like values.

In some embodiments, a disinfection region created within the interior volume 112 is characterized by the delivery of disinfecting radiation at a substantially uniform irradiance within the region. As used herein in reference to a disinfecting region, the term "substantially uniform" refers to a region within which the irradiance of the disinfecting radiation does not vary by more than 10% within the entire region (i.e., the irradiance measured within the region does not vary by more than 10%). In particular embodiments, "substantially uniform surface irradiation" refers to a disinfecting region wherein the intensity at which the disinfecting radiation is delivered to the surface(s) of the article to be disinfected does not vary across any portion of those surface(s) by more than an amount selected from ±30%, ±25%, ±20%, ±15%, ±10%, and ±5% or another like value. The disinfection regions may be re-defined or custom-tuned for different types of target articles 240, different regions of target articles 240 intended for disinfection, different operational states of radiation sources 120, or for other reasons. Further, the disinfection regions may be dynamically adjusted, collectively adjusted, independently adjusted, or adjusted in some other way. For example, if it is determined that the radiation intensity variation within a disinfection region is beyond a threshold, e.g., 10%, the disinfection region may be redefined into two or more disinfection regions according to a generated disinfection program, for example, or by some other logic.

Though disinfection does not require that radiation be delivered uniformly, it may be useful to have reasonably uniform irradiance in a local volume/region within which a target article 240 is positioned. A uniform distribution may be used to confirm the actual power level that is established where one or more surfaces of a target article 240 are being disinfected. For example, when a selected volume or region is uniformly irradiated, the radiation dosage reaching one or more surfaces in the selected volume or region may be inferred from a sensor measurement of radiation in the selected volume or region. In this way, a minimum dose of radiation that is determined to achieve the level of disinfection desired may be delivered to an intended surface and the chance of overexposure can be reduced.

The one or more interior walls 230 defining the interior volume 112 of the disinfecting chamber 110 may also be configured to work in conjunction with the one or more radiation sources 120 of disinfecting radiation to deliver high intensity disinfecting radiation to the one or more disinfection regions within interior volume 112. For example, the one or more walls included in the disinfection chamber and, where included, the one or more reflective surfaces, can be configured to function in cooperation with the one or more radiation sources 120 of disinfecting radiation to provide one or more disinfection regions. In some embodiments, the interior volume of the disinfection chamber is defined by one or more sidewalls with a top and/or a bottom wall. In such embodiments, sources 120 of disinfecting radiation can be positioned on or within any sidewall, top wall, bottom wall, or at any junction between any of two or more sidewalls, a sidewall and a bottom wall, and a sidewall and a top wall. In addition, or in the alternative, a generated disinfection program may control one or more radiation sources 120 to deliver one or more desired levels of radiation to one or more different disinfection regions defined in the interior volume 112 of the disinfecting chamber 110. And the radiation intensity delivered to one disinfection region may concurrently be different from the radiation intensity delivered to another disinfection region.

The one or more walls 230 defining the interior volume 112 of the disinfection chamber 110 can provide any one of many cross-sectional shapes for the chamber. For example, in particular embodiments, the one or more walls 230 are configured to provide an interior volume 112 having a circular or multi-sided cross section, such as a rectangular, triangular, hexagonal or octagonal cross section. In some embodiments, the disinfection chamber 110 is configured such that the interior volume 112 is defined by a plurality of walls and the cross-sectional shape of the interior volume is a rectangular parallelepiped or an octagonal parallelepiped. In still other embodiments, the interior volume 112, or portions thereof, may be shaped as a circle, a parabola, a double ellipse, or some other shape. In some cases, interior walls 230 of the interior volume 112 may be added, removed, or alternatively or in addition re-positioned so that a disinfection chamber having an interior volume defined by a first cross-sectional shape is modified to have an interior volume defined by a second, different cross-sectional shape.

Embodiments of the disinfection chamber 110 may include a reflector (not specifically shown for simplicity) totally or partially behind the one or more disinfecting radiation source(s) 120, and in such embodiments, where the source 120 of disinfecting radiation emits UV radiation and is a line source, such as, for example, a tube that emits UV-C radiation, the reflector may be parabolic, with the UV-C radiation source at or near its focus. Such a configuration can result in sending light, upon its initial reflection from the parabolic reflector, being sent out in mostly parallel rays. Of course other reflector geometries, UV radiation source locations, and resulting radiation fields are possible. Where tubes emitting UV-C radiation are used as the one or more sources of disinfecting radiation, in some embodiments, the rated total power delivered by the source tubes (i.e., UV-C fluence leaving the source, integrated over a surface area that encompasses the source) may range from about 20 W to about 200 W. The input electrical power consumed by disinfecting radiation source(s) 120 (e.g., UV tubes) is related and informative of the output UV power delivered from these sources, but it is noted that the relationship is not linear, and the relationship will generally change over time. In specific embodiments, however, the input power for UV tubes used in a disinfection chamber as described herein may be selected from, for example, 20 W, 25 W, 30 W, 35 W, 40 W, 45 W, 50 W, 55 W, 60 W, 65 W, 70 W, 75 W, 80 W, 85 W, 90 W, 95 W, 100 W, 135 W, 150 W, or another like value.

One or more sources 120 of disinfecting radiation may be positioned around the one or more sidewalls 230 of the interior volume 112 in a manner that results in radiation of a selected intensity (such as, e.g., energy of an intensity as described in relation to the disinfection regions) being delivered to the one or more disinfection regions within interior volume 112. The one or more sources 120 of disinfecting radiation can be positioned around the interior volume 112 to provide a disinfection region with a certain radiation intensity. For example, in embodiments of the interior volume 112 having one or more sidewalls 230, two or more sources 120 of disinfecting radiation, such as two or more sources 120 of UV-C radiation may be positioned along one or more of the sidewalls at uniformly spaced locations. In embodiments having multiple sidewalls, one or more sources 120 of disinfecting radiation may be positioned at one or more corners of the sidewalls. Where the disinfection chamber includes at least one top or bottom wall or surface, one or more sources 120 of disinfecting radiation can be positioned at a top and/or bottom wall or surface to provide a certain level of irradiance of disinfecting radiation directed into one or more disinfection regions formed within the interior volume 112. In specific embodiments, where the interior volume 112 of the disinfection chamber 110 is configured to include two or more sidewalls 230 and a bottom wall 230, with a UV radiation source 120 at each corner formed between the sidewalls and at least one UV radiation source 120 positioned at the bottom wall, the input power of each corner tube may be at least 50 W, and where included, the power of the bottom one or more tubes may be at least 30 W.

To facilitate positioning of target articles 240 within the interior volume 112, the disinfection chamber 110 can be provided with a moveable base, e.g., a suspension assembly, which positions one or more target articles 240, e.g., an ultrasound probe or other medical instrument, within the chamber. A suspension assembly as described herein works to position one or more articles to be disinfected consistently within the disinfection chamber. In these cases, where the disinfection chamber is designed to create one or more disinfection regions, providing a suspension assembly allows consistent, repeatable positioning of the one or more articles to be disinfected within disinfection region(s), thereby ensuring the one or more articles are subjected to high intensity radiation during a disinfection cycle.

In particular embodiments, a suspension assembly 242 may be provided that positions a target article 240 in a central portion of the disinfection chamber, where a disinfection region of high-intensity radiation is created. In some variations, for instance, when the article is connected to a cable that may then extend out of the chamber, the suspension assembly comprises a slot at the top of the assembly that extends to a central portion of the top of the disinfection chamber. In some cases, the suspension assembly 242 may include one or more control mechanisms arranged to receive control signals from a processing device such as controller 140. In these or other cases, the suspension assembly 242 may operate according to a generated disinfection program to adjust the position of a target article 240 in the disinfection chamber 110 in two dimensions (e.g., up, down, left, right), three dimensions (e.g., rotation, lateral motion), four dimensions (e.g., time dependent, motion during a disinfection cycle), or some other number of dimensions. In some cases, a suspension assembly 242 includes registration features to help align a target article 240. In some cases, a suspension assembly 242 is permanently or semi-permanently fixed such that the target article 240, once placed in the interior volume of the disinfection chamber 110, does not move during a disinfection cycle.

As will be appreciated, the positions of the shape and size of interior volume 112, the position, shape, and light reflective properties of reflective interior sidewalls that define interior volume 112, the amount and positions of radiation sources 120, the movement of moveable base and other structural configurations of interior volume 112 may all affect the radiation intensity delivered to a disinfection region within interior volume 112. In the description herein, all such structural configurations of and/or within interior volume 112 are referred to as "structural configurations" of interior volume 112.

The number and positioning of the one or more sensors 130 included in the disinfection device 100 are also selected to provide rapid, high-level disinfection at a low temperature. For purposes of the present description, a sensor 132 includes any device or assembly of components that collects and measures an environmental condition. When referring to one or more sensors 130 for detecting disinfecting radiation within the disinfection chamber, the one or more sensors 130 will each be a device or assembly of components capable of collecting information regarding the disinfecting radiation present in the disinfection chamber, sensing or measuring the amount of disinfecting radiation within the disinfection chamber, and amplifying or processing the collected information regarding the disinfecting radiation. Further, in the context of the present description, a sensor 130 is considered to be positioned within the disinfection chamber where any component of the sensor 130 is capable of detecting, measuring, transmitting, processing, or communicating processed information regarding the disinfecting radiation present within the disinfection chamber, whether or not it is positioned within or directly exposed to the interior of the disinfecting chamber.

Each of the one or more sensors 130, 132 included in the interior volume 112 may be capable of detecting and communicating information such as a total radiation dose, a rate of exposure over time, and the like, to controller 140 (FIG. 1). For example, where UV-C light is used as the disinfecting radiation, the sensors 130 may sense the UV-C dose received by the target article 240 and/or the amount of UV-C radiation emitted by one or more UV-C sources 120 included in the disinfection device. In some embodiments, UV-C sensors 130 included in the disinfection devices described herein may be one or more photodiodes fixedly or movably positioned within the interior volume 112 of the disinfecting chamber 110. In other embodiments, the one or more sensors 130 may comprise one or more light conducting components such as lenses, mirrors, filters and other optical elements used to collect radiation within the chamber, and may also comprise fiber optic cables or light pipes that conduct the collected disinfecting energy to a detector, such as a photodiode. In some variations, the sensors 130 within the disinfection chamber 110 are configured to have a band-pass optical filter or other electromagnetic filter in front of them so that only radiation in the spectrum of interest is sensed. In some embodiments, one or more sensors 130 may be positioned on or incorporated into the one or more articles to be disinfected. Positioning of one or more sensors 130 on the one or more target articles 240 to be disinfected may provide more accurate reading of the disinfecting radiation reaching the article 240. The devices described herein may include one or more sensors 130 that utilize, for example, multiple optical conductors positioned to monitor direct and indirect sources of the disinfecting radiation. Photonic conductors useful in the context of the devices described herein include, but are not limited to, fiber optic "cable" (suitable for conducting light over a long distance with low loss) or a simple "light pipe" formed of a glass, polymer, or other simple, optically transparent material that traps and contains light within itself and conducts the light with low loss. Where used, a "light pipe" as referenced herein is typically more suited to conducting light over short distances to prevent undesirable losses. A lens may be used to gather radiation and direct it to a detecting device, or the gathered radiation may be transported to another location for measurement.

It may be beneficial in some embodiments to include one sensor 130 or a set of sensors 130 to detect the global (i.e., aggregate) radiation dosage delivered to the interior volume 112 and another sensor 130 or set of sensors 130 to check or monitor each disinfection region within interior volume 112.

In one embodiment, a disinfection system 100 is controlled by controller 140 (FIG. 1) to direct operation of a radiation source 120 with a specified power level and a specific period of time, namely to reach a determined cumulative threshold radiation dosage. For example, where UV-C radiation is used as the disinfecting radiation, in particular embodiments, the predetermined threshold dose may be selected from between about 50,000 $\mu J/cm^2$ and about 10,000,000 $\mu J/cm^2$. In certain such embodiments, the dose may be selected from between about 50,000 $\mu J/cm^2$ and about 1,000,000 $\mu J/cm^2$, such as, for example, a dose selected from between about 50,000 $\mu J/cm^2$ and about 750,000 $\mu J/cm^2$, between about 50,000 $\mu J/cm^2$ and about 650,000 $\mu J/cm^2$, between about 50,000 $\mu J/cm^2$ and about 500,000 $\mu J/cm^2$, between about 50,000 $\mu J/cm^2$ and about 450,000 $\mu J/cm^2$, between about 50,000 $\mu J/cm^2$ and about 350,000 $\mu J/cm^2$, between about 50,000 $\mu J/cm^2$ and about 250,000 $\mu J/cm^2$, and between about 50,000 $\mu J/cm^2$ and about 100,000 $\mu J/cm^2$, or between other like values. In further such embodiments, the dose may be selected from between about 150,000 $\mu J/cm^2$ and about 750,000 $\mu J/cm^2$, between about 150,000 $\mu J/cm^2$ and about 650,000 $\mu J/cm^2$, between about 150,000 $\mu J/cm^2$ and about 500,000 $\mu J/cm^2$, between about 150,000 $\mu J/cm^2$ and about 450,000 $\mu J/cm^2$, between about 150,000 $\mu J/cm^2$ and about 350,000 $\mu J/cm^2$, and between about 150,000 $\mu J/cm^2$ and about 250,000 $\mu J/cm^2$, or between other like values. In still further such embodiments, the dose may be selected from between about 250,000 $\mu J/cm^2$ and about 750,000 $\mu J/cm^2$, between about 250,000 $\mu J/cm^2$ and about 650,000 $\mu J/cm^2$, between about 250,000 $\mu J/cm^2$ and about 500,000 $\mu J/cm^2$, between about 250,000 $\mu J/cm^2$ and about 450,000 $\mu J/cm^2$, and between about 250,000 $\mu J/cm^2$ and about 350,000 $\mu J/cm^2$, or between other like values.

Figure 4:
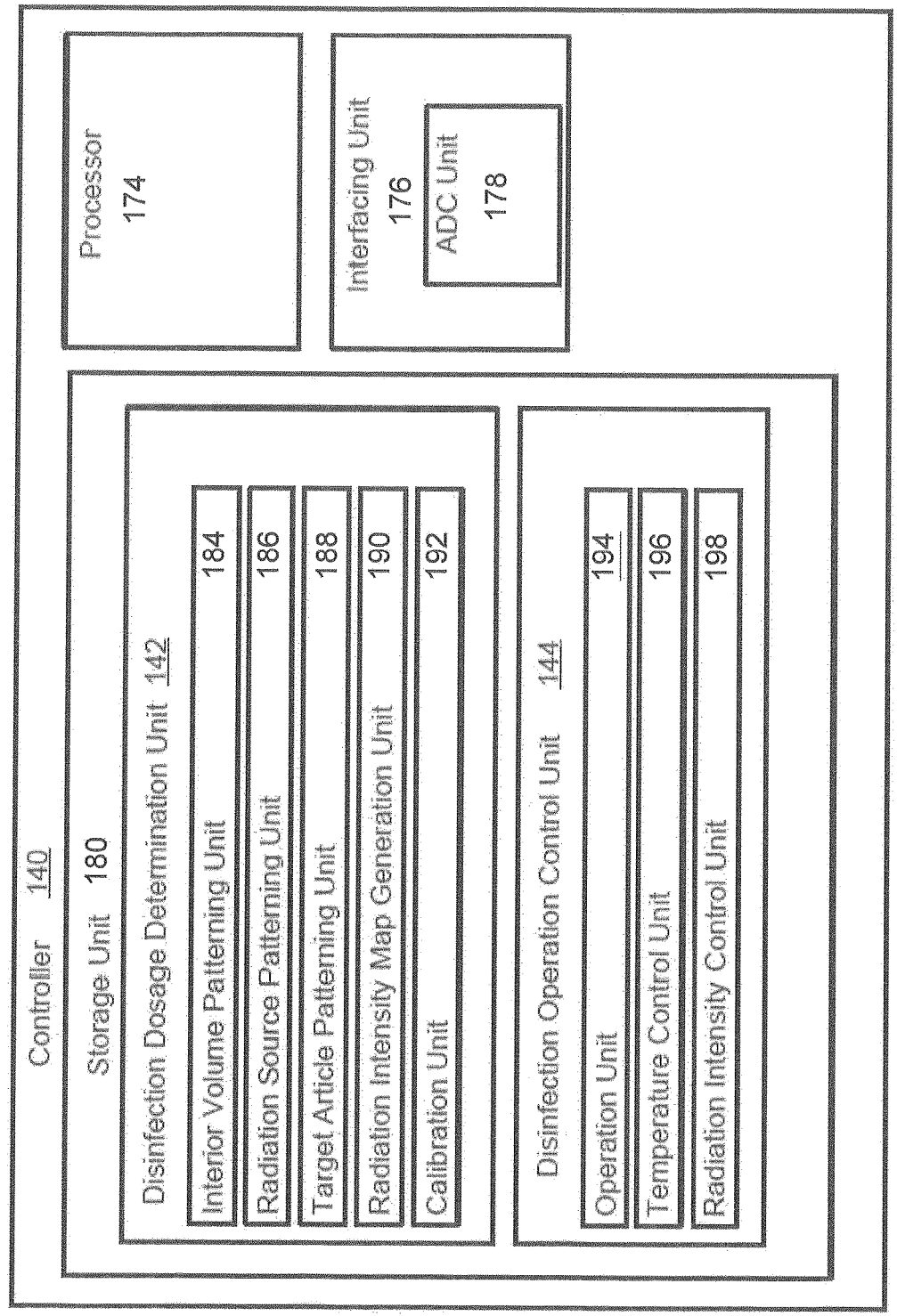
FIG. 4 illustrates details of an exemplary controller.

FIG. 4 illustrates details of an exemplary controller 140. As shown in FIG. 4, controller 140 may include a processor 174 and an interfacing unit 176 including at least one analog-digital-converter (ADC) unit 178. Interfacing unit 176 may communicate with one or more of disinfection chamber 110, radiation source 120, sensors 130, database 150, and/or disinfection requirement input 160 with respect to data/information related to the control of the disinfection operation. ADC unit 178 may convert analog data, such as the data detected by sensors 130, into digital data suitable for processing by processor 174.

Controller 140 may also include a storage unit 180 having a disinfection exposure determination unit 142 and a disinfection operation control unit 144 contained therein. Disinfection exposure determination unit 142 may include an interior volume patterning unit 184, a radiation source patterning unit 186, a target article patterning unit 188, a radiation intensity map generation unit 190, and a calibration unit 192. Disinfection operation control unit 144 may include an operation unit 194, a temperature control unit 196, and a radiation intensity control unit 198. Disinfection exposure determination unit 142 and a disinfection operation control unit 144 may be stored in one or more storage medium as software, embedded firmware, programmable logic, a combination thereof, or other suitable storage forms.

Disinfection exposure determination unit 142 is generally configured to determine a disinfection exposure for a target article 240 placed in a disinfection system 100 that includes a disinfection chamber 110 and a radiation source 120. Specifically, interior volume patterning unit 184 is configured to identify a structural configuration of the interior volume 112 of disinfection chamber 110. Radiation source patterning unit 186 is configured to identify at least one radiation emitting characteristic of radiation source 120. Target article patterning unit 188 is configured to identify at least one structural configuration and material characteristic of a target article 240. Radiation intensity map generation unit 190 is configured to generate a radiation intensity map based on the UV-C radiation emitting characteristics of radiation source 120, the structural configuration of interior volume 112, and the structural configuration and material characteristics of target article 240. The generated radiation intensity map indicates radiation intensity values of one or more disinfection regions within interior volume 112 of disinfection chamber 110. Calibration unit 192 is configured to generate calibration values based on actual radiation intensity data detected by sensors 130 (FIG. 2B). The actual radiation intensity data may be obtained with a calibration object being positioned within interior volume 112 and with radiation source 120 in operation in a manner comparable to that under which the radiation intensity map is generated. As discussed herein, the generated calibration values are in some cases weighting factors, attenuation factors, or other such factors used to adjust values generated by sensors 130 during actual operation. Details of the operations of disinfection exposure determination unit 142 are further described herein with respect to the example operations.

Disinfection operation control unit 144 is configured to control a disinfection operation of a target article 240 based on a disinfection exposure (e.g., a minimum dose) determined by disinfection exposure determination unit 142 and in accordance with a generated disinfection program. The radiation dosage may be based on the radiation intensity map and may stipulate a period of time each disinfection region receives radiation. Specifically, operation unit 194 may implement the disinfection operation based on the determined dosage. The operation may include the movement of the target article 240 within the interior volume 112, the power state of the radiation source 120, the period of time each radiation source 120 is turned on/off during the operation of the disinfection cycle, and other factors.

Temperature control unit 196 is configured to control the disinfection operation based on detected temperature information of target article 240 and/or a disinfection region within interior volume 112. Radiation intensity control unit 198 is configured to control the disinfection operation based on the detected radiation intensity in a disinfection region within interior volume 112.

For example, if based on the radiation intensity data detected by sensors 130, and if radiation intensity control unit 198 determines that the required minimum dose has not yet been achieved, radiation intensity control unit 198 may function with operation unit 194 to continue to run for an interval of time set to bring the total exposure to the disinfecting radiation up to the selected (e.g., minimum) threshold dose. In such an embodiment, the selected threshold of disinfecting radiation can be determined based on the radiation dosage determined by disinfection exposure determination unit 142. For example, the disinfection system 100 can be configured and controlled to stop a disinfection cycle once it is confirmed that one or more of the following conditions have been satisfied: 1) each of the sensors 130 have received a predetermined (minimum) dose of disinfecting radiation; 2) the average dose received by the sensors 130 has reached a threshold (e.g., minimum) dose; 3) at least one individual sensor has received a first threshold (e.g., minimum) dose and all the remaining sensors 130 have received a second threshold (e.g., minimum) average dose; 4) one or more sensors 130 positioned to directly receive disinfecting radiation have received a first threshold (e.g., minimum) dose and one or more additional sensors positioned to monitor aggregate or indirect radiation have received a second threshold (e.g., minimum) dose; and 5) a first group of two or more sensors have received an average dose that meets a first threshold (e.g., minimum) dose and a second group of two or more additional sensors have received an average dose that meets a second threshold (e.g., minimum) dose. As used herein, the terms "first threshold dose" and "second threshold dose" do not necessarily refer to different values. The first and second threshold doses of disinfecting radiation may be the same, or, in other embodiments, the first and second threshold doses may be different.

In particular embodiments, disinfection processes, according to the present description, take place at acceptably low temperatures. In one embodiment, where the surface temperature of the article being disinfected is to be maintained below a particular threshold, one or more temperature sensors 132, such as one or more infrared temperature sensors 132, may be used to monitor and communicate the surface temperature of the article 240 being disinfected. Alternatively, it may be sufficient to simply monitor the air temperature within interior volume 112 or the temperature of one or more of the interior walls 230. Where the air temperature or a wall temperature within the disinfection chamber 110 is monitored, the monitoring location may be selected to reasonably detect the surface temperature of the one or more target articles 240 being disinfected to a reasonable accuracy. In such embodiments, a location for temperature monitoring within the interior volume 112 of the disinfection chamber 110 that correlates to the surface temperature of the one or more target articles 240 being disinfected can be selected via testing that monitors the surface temperature of the target articles 240 and identifies an area or location within the chamber that exhibits a temperature that is suitably correlated to the target article 240 surface temperature. In such an instance, the disinfection chamber may include one or more ambient temperature sensors 132 that monitor and communicate the ambient temperature of the interior volume 112 of the disinfection chamber 110 while a disinfection cycle is being carried out.

Based on the temperature data detected by sensors 132, temperature control unit 196 may control operation unit 194 to adjust the operation state. For example, if the temperature is higher than a threshold temperature, temperature control unit 196 may work to reduce the thermal heat content of the interior volume 112 and thereby cool down the interior volume 112, and in achieving this cooling, may as an additional effect, lower the power output of radiation source 120. For instance, it has been found that light tubes generating UV-C radiation work with an acceptable efficiency at a temperature of between about 35° C. and about 45° C. In certain embodiments, temperature control unit 196 as described herein may be configured to: 1) pre-warm the interior volume 112 to a temperature within a selected or selectable temperature range for the one or more radiation sources 120 of disinfecting radiation prior to initiation of a disinfection cycle; and 2) actively warm or cool the interior volume 112 so as to maintain a temperature range that does not result in undesired degradation of the target articles 240 being processed, and also does not move below the selected threshold temperature range for the one or more sources 120 of disinfecting radiation. In order to maintain the interior volume 112 of the disinfection chamber 110 at an acceptable temperature, the temperature control unit 196 may include or otherwise direct one or more sources of heat. In such embodiments, the sources of heat may include the one or more radiation sources 120 (e.g., one or more UV-C tubes) or any other suitable source of heat or heating element, including known electrical heating devices, infra-red heating devices, and radiant heating devices.

The disinfection systems 100 and the components thereof described herein may or may not be portable. System 100 and the components thereof according to the present disclosure can be configured to suit the chosen parameters of the particular context and application in which the devices and systems will be put to use. In embodiments where the housing is portable, the housing may be moved in close proximity to the article, or a portion of the article, that requires high-level disinfection. In certain contexts, portability of the devices and systems according to the present description is advantageous as such portability reduces or eliminates the need to bring the target articles 240 to be disinfected to the device or system 100 itself. When the embodiment is portable, the devices and systems may be configured to utilize any power source commonly located within a home, clinic, or hospital setting. Alternatively, in embodiments of a portable device or system 100 as described herein, one or more components of the system 100 may be powered by one or more batteries or other portable power sources to reduce or eliminate the need to access a fixed power source. Various batteries, battery technologies, and power management technologies are well-known in the art and can be utilized in devices and systems according to the present description.

A strategy of the present disclosure is to determine an appropriate radiation dose (i.e., minimum dose) for disinfection of a target article 240 of any type. This strategy facilitates disinfection on all surfaces of the subject target article 240 regardless of the article's geometry. To facilitate the strategy, the interior volume 112 of the disinfection chamber 110 is modeled, radiation patterns within the empty chamber are modeled, a target article 240 is modeled, and radiation patterns within the chamber when the target article 240 is present are modeled. Based on the models, a disinfection program is generated that will provide radiation into the interior volume 112 of the disinfection chamber 110 when the target article 240 is present sufficient to perform high-level disinfection (HLD). When the disinfection program is loaded into the disinfection system 100 and executed using controller 140, for example, a minimum dose of radiation will be provided, and the target article 240 will be disinfected. The implementation of the strategy may be supplemented with additional procedures and structures. For example, a calibration device may be operated in a disinfection chamber 110 to collect data that is used to verify one or more of the models, radiation maps, and the disinfection program. One or more on-board sensors 130, 132 may be used to supplement information in one or more of the models and radiation maps, and sensor information may be further used to control certain operations of the disinfection program.

FIGS. 5A to 5E are a disinfection chamber 110 along the lines of FIG. 2B. The disinfection chamber 110 includes an interior volume 112, one or more radiation sources 120, one or more sensors 130, and a suspension assembly 242, as illustrated. Other structures and features of the disinfection chamber 110 are not shown to keep the figures uncluttered for the present discussion.

In some cases, a disinfection chamber 110 of FIG. 5 may be deployed for use in a medical facility, a manufacturing facility, or some other location. In these locations, the disinfection chamber 110 is used to disinfect any number of target articles of any number of types. This first type of disinfection chamber 110 may be referred to as a deployed disinfection chamber, a commercial disinfection chamber, a production disinfection chamber, or by some other such term. In other cases, the disinfection chamber 110 may be used to create three dimensional models of a disinfection chamber or radiation intensity maps, or this second disinfection chamber may be used for other testing or data collection purposes. This second type of disinfection chamber may be referred to as a test disinfection chamber, a data collection disinfection chamber, or some other like term. It is recognized that in some cases, the first and second types of disinfection chambers are identical, and in other cases, they are different. In some cases a single disinfection chamber may be operated at one time as a test or data collection disinfection chamber and used at another time as a deployed or commercial disinfection chamber.

Figure 5A:
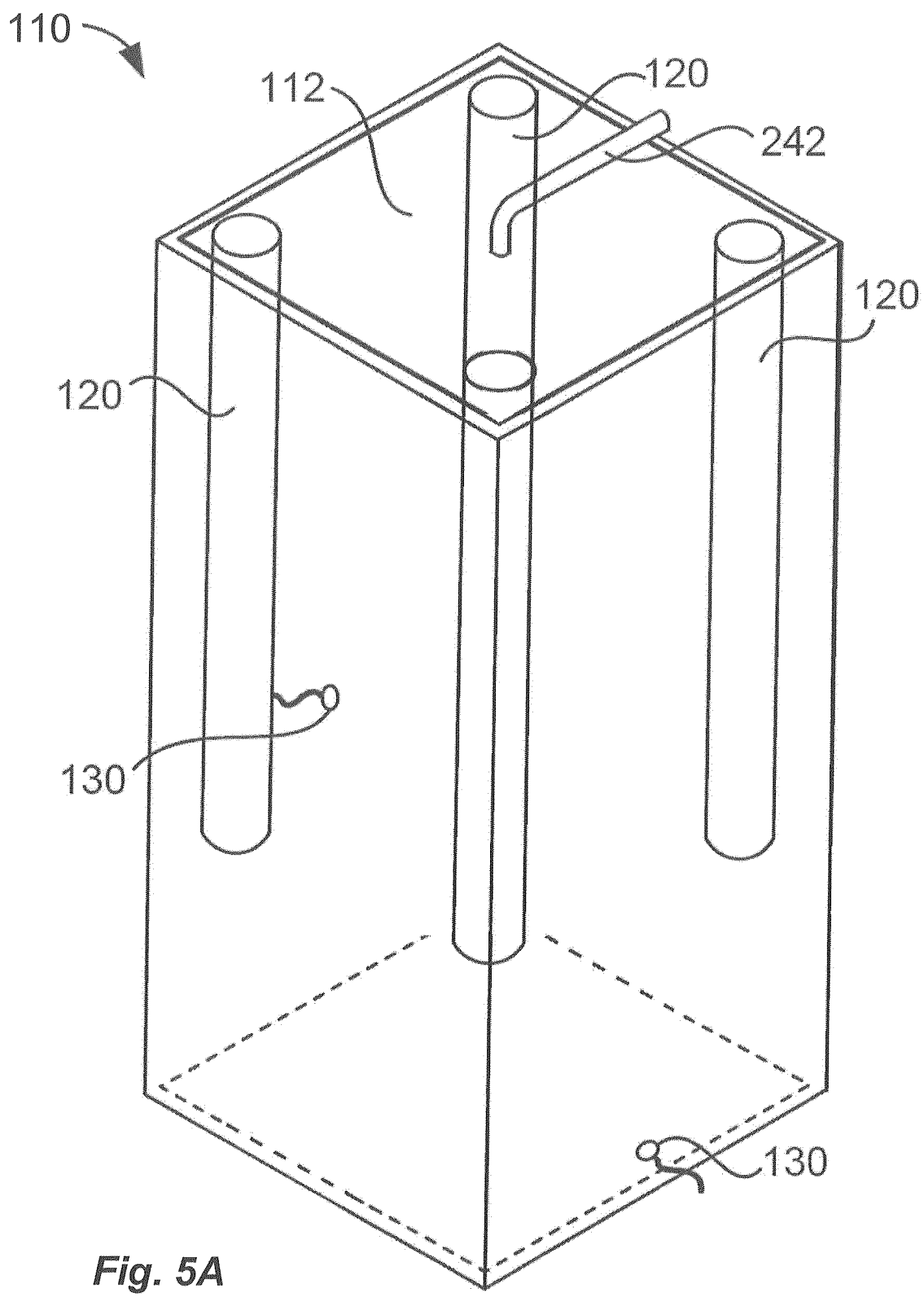
FIGS. 5A to 5E are a disinfection chamber along the lines of FIG. 2B.

The disinfection chamber 110 of FIG. 5A is empty. The disinfection chamber 110 of FIGS. 5B to 5E include a target article 240 coupled to the suspension assembly 242 in the interior volume 112. FIGS. 5A to 5E may be collectively referred to herein as FIG. 5.

The disinfection chamber 110 of FIG. 5 may be operated to produce any number of maps of radiation intensity of disinfection regions within the interior volume 112. The radiation intensity maps are developed/obtained based on the structural configuration of the disinfection chamber 110 and the radiation light emitting characteristics of the specific radiation sources 120 coupled to the disinfection chamber 110. Various radiation maps can be formed by operating the radiation sources 120 at various power settings, in various sequences, for various durations, or in any other way. Separate radiation maps may be generated based on the sole operation of each separate radiation source 120. In some cases, radiation maps are generated after disinfection system 100 (FIG. 1) is operating in the field. In this way, periodically generated radiation maps may be compared to each other so that certain functional characteristics (e.g., build-up of dirt or contaminants on the radiation sources, the age of radiation sources, changes in sensitivity of detectors, and other characteristics) of the particular system can be tracked. In at least some of these cases, the crossing of one or more thresholds during comparisons of such generated radiation maps can trigger an indication (e.g., an indicator on a user interface, a broadcast message, a reset or shutdown of the system, or the like) to service the system.

Figure 5B:
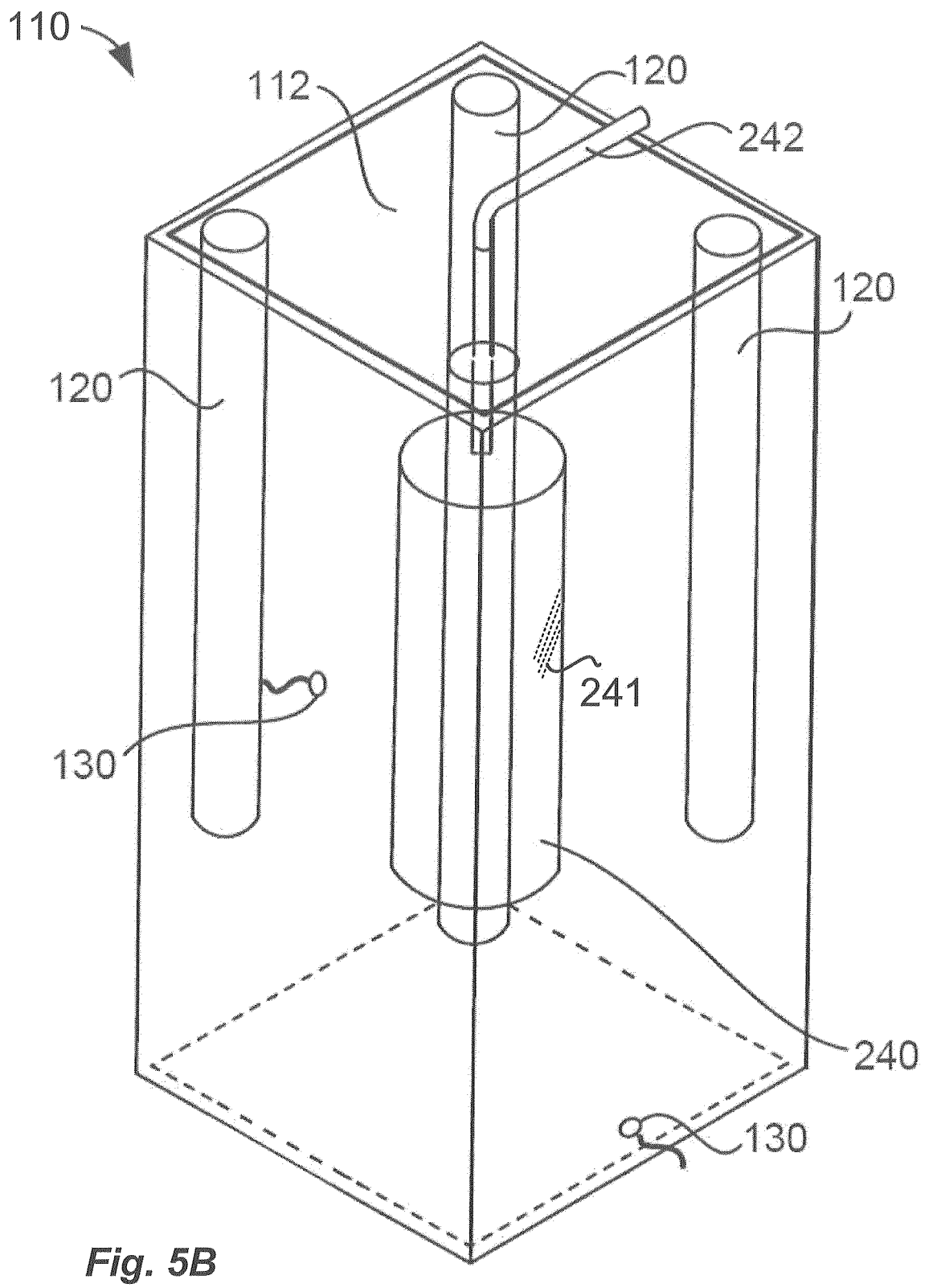

In some cases, such as in FIG. 5B, radiation maps may also be generated factoring in the target article 240 positioned in the interior volume of the disinfection chamber. That is, the radiation light reflection, blocking, and/or absorption or other optical properties of the target article to be disinfected are considered in the generation of the radiation maps. For example, the surface structural configuration of the target article 240 and the surface material of the target article 240 will affect the determination of the radiation intensity within the interior volume 112 of the disinfection chamber 110. The presence of the target article 240 will expectedly change the radiation received at sensors 130. By operating the disinfection chamber 110 without a target article, a first set of data measured and collected from sensors 130 during a first disinfection cycle can be used to generate a first radiation map. By positioning a target article 240 in the interior volume 112 of the disinfection chamber 110 and then operating the disinfection chamber 110 through a second same disinfection cycle, a second set of data measured and collected from sensors 130 can be used to generate a second radiation map. Comparing the first and second radiation maps to each other will generate a set of data that represents the impact on radiation delivered in the interior volume 112 caused by the target article 240.

Information to supplement or otherwise modify radiation maps can be gathered in other ways as well. For example, target article 240 may in some cases have a radiation-sensitive material 241 applied to some portion of its surface or all of its surface. In these cases, when such a coated target article 240 is irradiated while inside the disinfection chamber, the radiation-sensitive material 241 will be affected. In some cases, a value representing a dose of the radiation received at the surface of the test article 240 may be calculated based on changes to the radiation-sensitive material 241 after being irradiated. The amount of change to the radiation-sensitive material 241 may be proportional to the amount of radiation received at the respective surface. In this way, one or more region of interest on the surface of the target article may be determined. For example, by irradiating a target article 240 having a radiation-sensitive material 241 applied to its surface, a region of the target article 240 that is shielded from having a line-of-sight path to a radiation source may be determined to receive less radiation than other regions of the target article 240 (i.e., a cold spot). As another example, if a portion of the target article is very close to a radiation source, it may be determined that the close-by portion receives more radiation than other regions of the target article 240 (i.e., a hot spot).

The radiation-sensitive material 241 may or may not be visible on the surface of the target article 240. In some cases, the radiation-sensitive material 241 is applied as a paint. In some cases, the radiation-sensitive material 241 is on an adhesive-backed substrate, and one or more of these "patches" are adhered to regions of interest on the surface of the target article 241. In still other cases, the radiation-sensitive material 241 is formed as a dust, powder, film, dye, ink, or other substance.

In some cases, the radiation-sensitive material 241 is a silver emulsion material, such as silver bromide, silver iodide, and silver sulfide. In other cases, the radiation-sensitive material 241 may be a spirooxazines dye dissolved in an organic solvent such as toluene, xylene, methanol or ethanol, or the like. In these or still other cases, the radiation-sensitive material 241 may a photochromic dye such as 1,3,3-Trimethylindolinonaphthospirooxazine, a diarylethene, a spiropyran, a spiroperimidine, a viologen, an azobenzene, or some other photosensitive material.

Radiation maps may be generated based on the amount of radiation measured by one or more on-board sensors 130. In addition, or in the alternative, radiation maps may be generated based on a calibration device in the disinfection chamber 110. The calibration device may be a type of target article 240 having one or more integrated sensors 130. In this way, in addition to generating radiation map data, the radiation values measured by the calibration device may be used to validate or calibrate the values measured by other sensors located in the disinfection chamber 110.

Figure 5C:
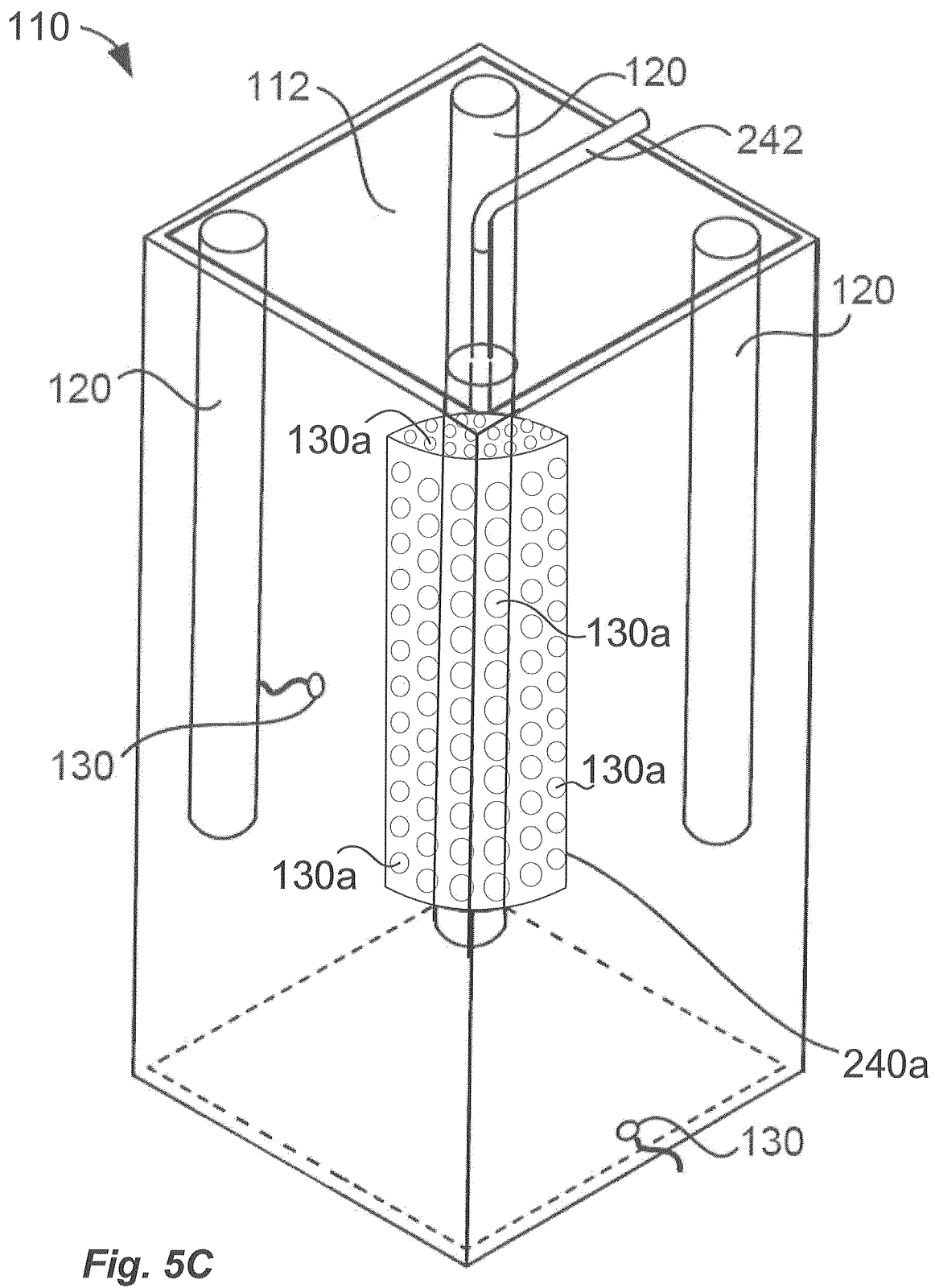

FIG. 5C is a disinfection chamber 110 configuration having a target article calibration device 240a positioned in the interior volume 112. The target article calibration device 240a is suspended from the suspension assembly 242 in FIG. 5C, but in other cases, the target article calibration device 240a may be positioned, moved, situated, configured, or located in the disinfection chamber in some other way.

The target article calibration device 240a includes any number of target article sensors 130a. In FIG. 5C, only four target article sensors 130a are expressly referenced, but it is understood that each of the target article sensors 130a actually utilized on the target article calibration device 240 is accounted for. Along these lines, radiation measurements collected with each target article sensor 130a may be computationally coupled to a location on the target article calibration device 240a where the sensor is formed, integrated, or otherwise positioned. The radiation measurements collected with each target article sensor 130a may be further computationally coupled with a point in the disinfection cycle.

Using a target article calibration device 240a that has a surface area substantially like an actual target article 240, a radiation map with dense, accurate radiation information can be formed. Additionally, by tracking radiation measurements captured with sensors 130 during a disinfection cycle, while concurrently capturing target article sensor 130a measurements when the target article calibration device is positioned inside the chamber, an effective disinfection cycle program can be generated to perform a suitable level of disinfection for a particular type of target article 240. Subsequently, the generated disinfection cycle program can be executed in a disinfection chamber 110 that contains a standard target article 240. By monitoring data measurements captured by sensors 130, the radiation sources 120, time of exposure, or both, can be controlled with appropriate resolution to deliver a minimum dose of radiation to the target article 240 while retaining substantial confidence that the desired disinfection has been achieved and the target article has not be subjected to additional, unnecessary radiation.

Figure 5D:
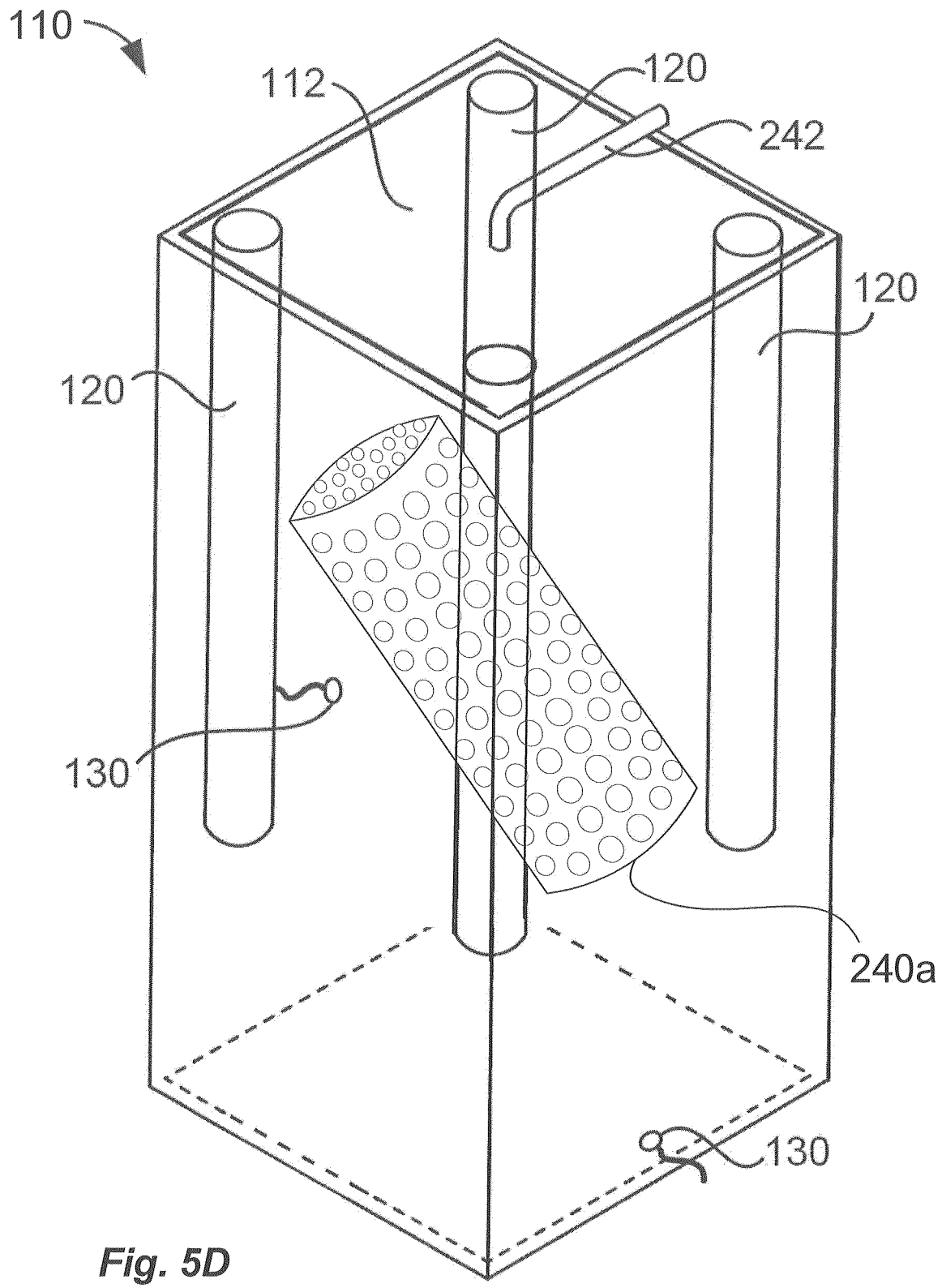

FIG. 5D is a disinfection chamber 110 configuration having a target article calibration device 240a positioned off axis in the interior volume 112. The mechanism of the suspension assembly 242 arranged to change the axis of the target article calibration device 240a is not shown for simplicity. In some cases, the target article calibration device 240a is fixedly positioned on the suspension assembly. In other cases, the target article calibration device 240a may be manually moved, automatically (e.g., controllably) moved, or semi-automatically moved within the disinfection chamber 110. A controller 140 may direct the movement of the target article calibration device 240a in any suitable way.

The target article calibration device 240a may be used to collect information from any number of sensors 130a, which are integrated into the target article calibration device 240a of FIG. 5D, but not identified so as to avoid cluttering the figure.

Figure 5E:
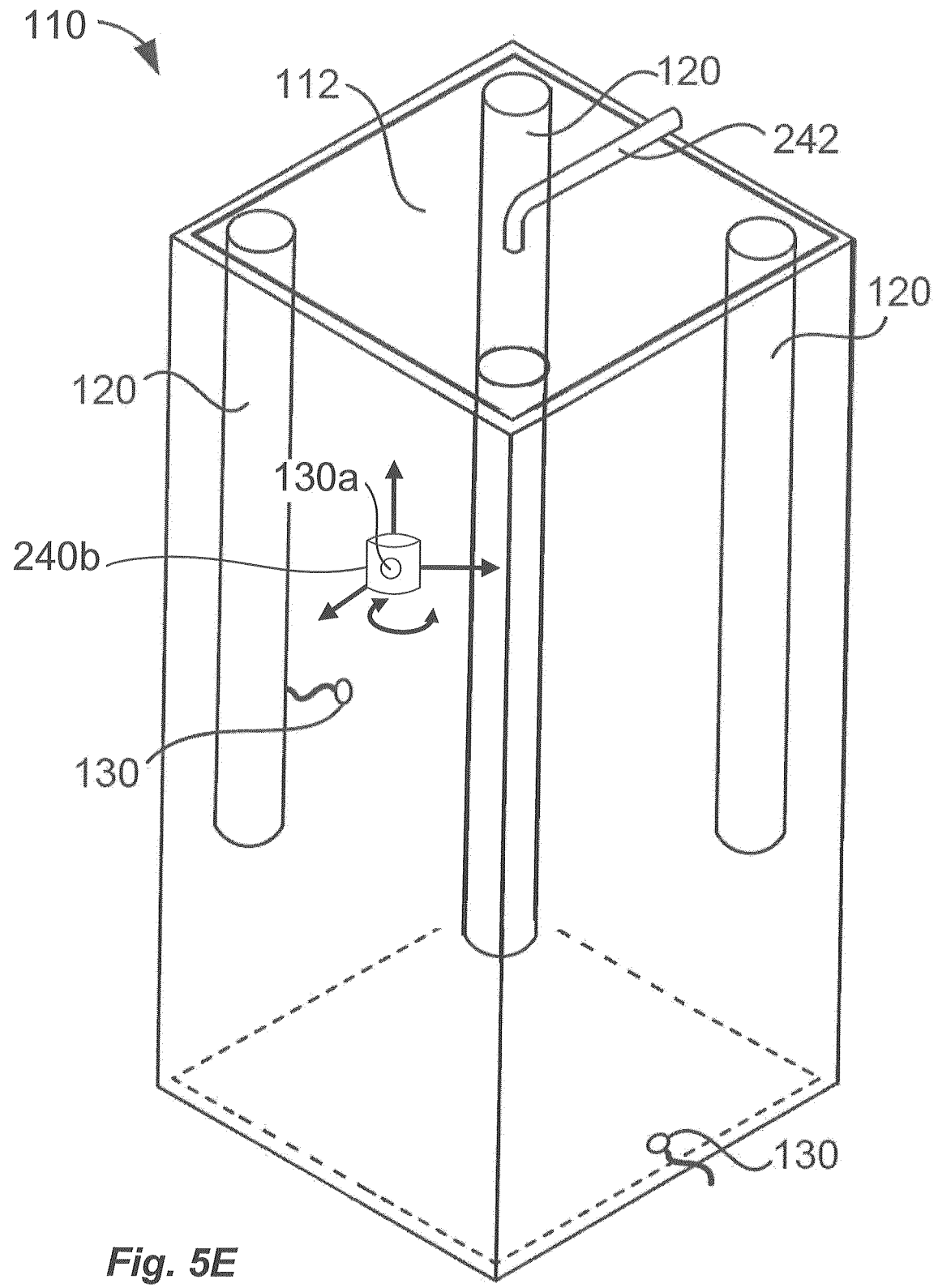

FIG. 5E is a disinfection chamber 110 configuration having another target article calibration device 240b positioned in the interior volume 112. The target article calibration device 240b may be arranged having any desired shape, configuration, materials, dimensions, and any other characteristics. The target article calibration device 240b of FIG. 5D includes any number of target article sensors 130b. The target article sensors 130b may be of any suitable type, such as the types described with respect to target article sensors 130a and sensors 130. In some cases, the target article calibration device may include a housing of a known medical probe modified to include any number of sensors 130a.

The target article calibration device 240b of FIG. 5E may be controlled in any number of dimensions. For example, in some embodiments, the target article calibration device 240b may be controlled in one dimension (e.g., up and down). In these or other embodiments, the target article calibration device 240b may be controlled in a second dimension (e.g., right and left). In these or other embodiments, the target article calibration device 240b may be controlled in a third dimension (e.g., front and back). In these or still other embodiments, the target article calibration device 240b may be controlled rotationally, over time, or in any other way. Using a target article calibration device 240b of the type represented in FIG. 5E, which may be operated according to a program, manually, or in some other way, for example, as directed by a controller.

The target article sensors 130a may be of any suitable type. In embodiments of the present disclosure, the target article sensors 130a may be along the same lines as the sensors 130.

Figure 6A:
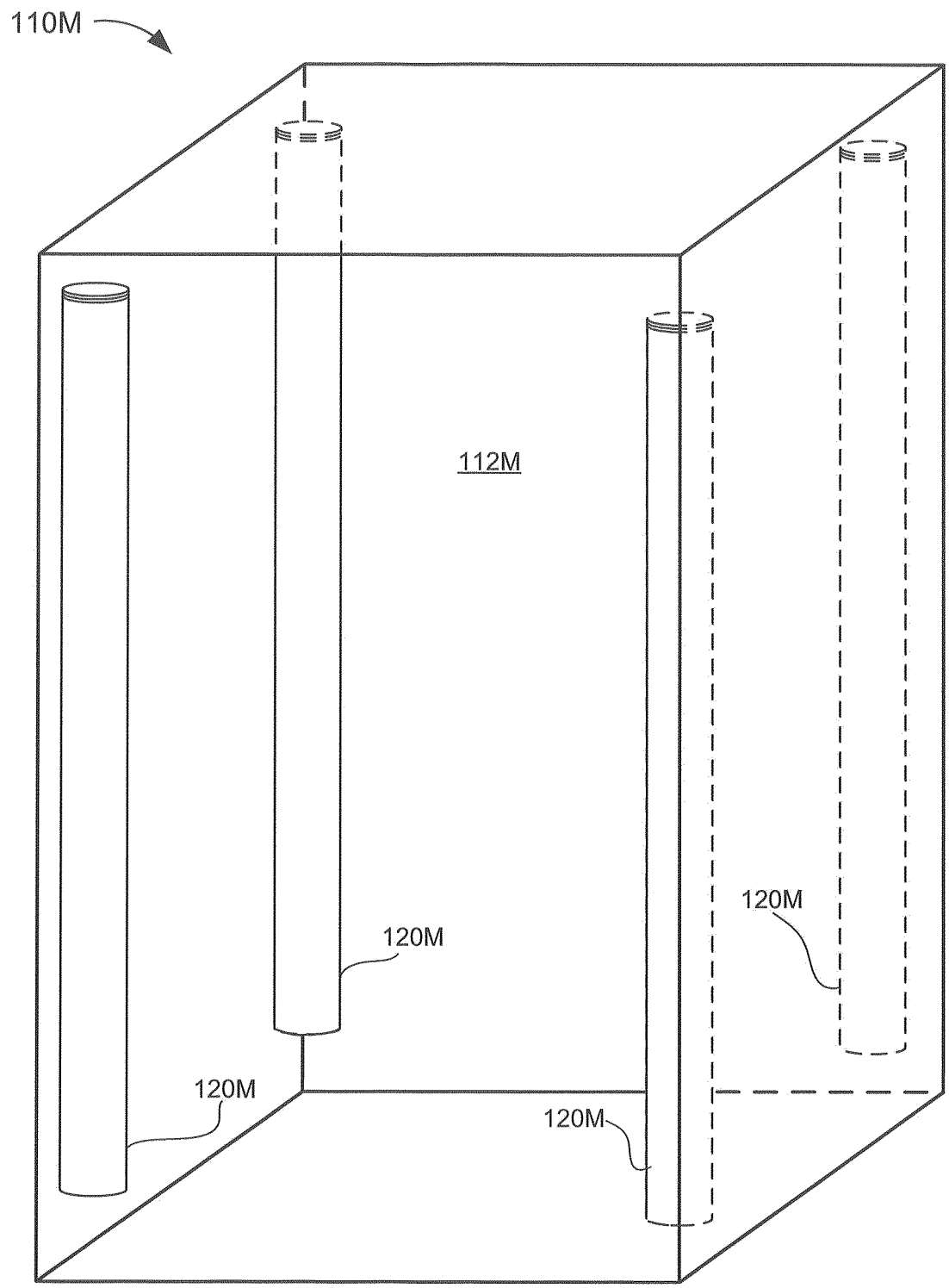
FIG. 6A is an initial model of a disinfection system.
Figure 6C:
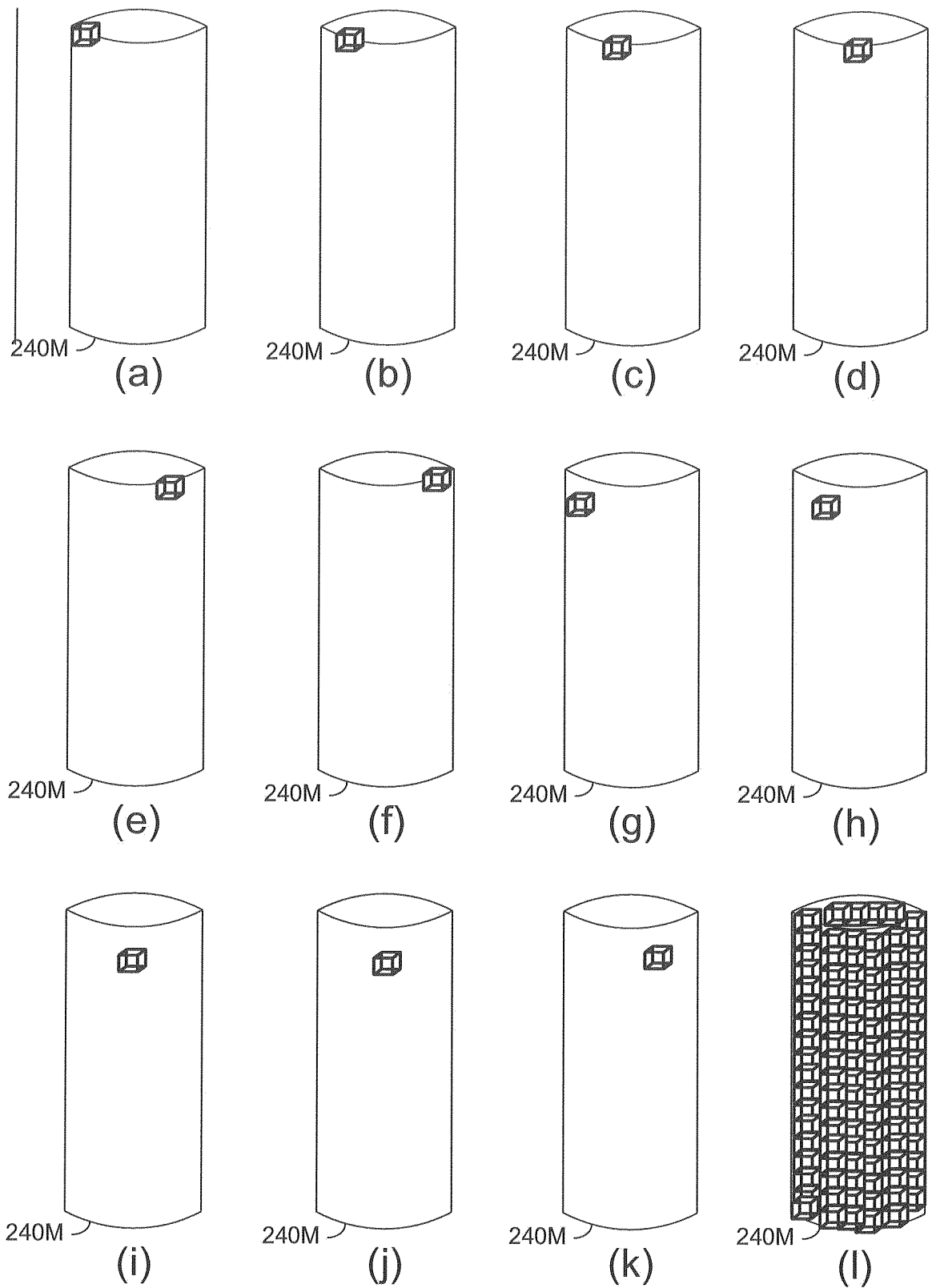
FIG. 6C illustrates one method of forming a target article model (FIGS. 6A-6C may be collectively referred to herein as FIG. 6)

FIGS. 6A to 6C are models of a disinfection chamber in various levels of formation. FIGS. 6A to 6C may be collectively referred to herein as FIG. 6.

Some models discussed with respect to FIG. 6 may be created via a disinfection exposure (e.g., dosage) determination unit 142 (FIG. 4) stored in a storage unit of a controller 140. The controller 140 in this case may be integrated with a disinfection chamber 110, or the controller in this case may be integrated with a different disinfection system 100. Along these lines, an interior volume patterning unit 184 (FIG. 4) may be arranged to generate, modify, apply, or otherwise process a three dimensional model of a disinfection chamber. A target article patterning unit 188 may be arranged to generate, modify, apply, or otherwise process a three dimensional model of a target article to be disinfected. A radiation source patterning unit 186 may be arranged to generate, modify, apply or otherwise process radiation emitting characteristics of a radiation source.

FIG. 6A is an initial model of a disinfection chamber 110M. The disinfection chamber model 110M includes an interior volume model 112M and a number (e.g., one, two, four, or any number) of radiation source models 120M. Other structures in a disinfection chamber, such as angles, corners, suspension assemblies, door hinges, mounting structures, and the like, may also be modeled, but these structures are not shown in FIG. 6A to help simplify the drawing. The software used to create the models may be any commercially useful modeling software, the details of which are not discussed in detail herein so as to avoid obscuring the inventive concepts set forth in the present disclosure. Dashed lines in FIG. 6A are intended to illustrate structures of the disinfection chamber model 110M that would otherwise be obscured behind walls of the modeled chamber. It is understood that the disinfection system being modeled, and any of its associated structures, may have any suitable shape, size, geometry, and other characteristics.

FIG. 6B illustrates one method of forming a disinfection chamber model 110M. The disinfection chamber model 110M is formed by arranging a plurality of virtual polygons to cover every surface or otherwise fill the entire virtual interior volume 112M of the disinfection chamber model 110M. The virtual polygons in the sequence (a) to (i) of FIG. 6B are arranged as uniformly sized cubes, but in other cases, each of the virtual polygons may have any desirable size, shape, dimension, orientation, or other useful characteristics. In some cases, one or more of the virtual polygons include edges that are mathematically predictable, but not straight. Different virtual polygons may have any one or more of different sizes, different shapes, different dimensions, different orientations, and other different characteristics. In at least some embodiments, these different virtual polygons may have "relatively small volume" and may be called "voxels," akin to pixels in a two dimensional (2D) setting. As used in the present disclosure in this context, "relatively small" is taken as such that the properties of interest can be suitably treated as constant over the extent of the differential element.

The sequence (a) to (i) of FIG. 6B illustrates a single virtual polygon (i.e., a cube) moving through the virtual disinfection chamber. The first virtual polygon in FIG. 6B(a) is formed in the top, left-front corner of the virtual interior volume 112M, and the second, third, and fourth virtual polygons in FIG. 6B(b) to FIG. 6B(d) move across the top, front row of the virtual interior volume 112M. In FIGS. 6B(e) and 6B(f), virtual polygons are formed in a second-from-the-top, front row of the virtual interior volume 112M. In FIGS. 6B(g) and 6B(h), virtual polygons are shown in a top, second-from-the-front row. In FIG. 6B(i), virtual polygons fill the entire space of the virtual interior volume 112M.

The sequence of virtual polygon formation and placement in FIG. 6B is helpful for understanding that virtual polygons will desirably cover every surface or otherwise fill the entire space of the virtual disinfection chamber, but the sequence is not limiting. In other cases, different patterns or algorithms may be used to create the virtual polygons of the disinfection chamber model 110M. Alternatively, virtual polygons may all be formed concurrently and not fully or even partially in sequence.

The formation of virtual polygons in FIG. 6B creates a mathematical mapping of every portion of the virtual interior volume 112M of the disinfection chamber model 110M. Such mapping may be referred to as a three-dimensional (3D) map, a 3D model, a multi-dimensional model, or the like. Each virtual polygon may be co-related with adjacent polygons, nearby polygons, and other polygons having particular mathematical relationships or positions. Each virtual polygon may be associated with a computing structure that stores information about the three-dimensional space represented by the corresponding polygon. The computing structure may, for example, store size information, shape information, angle information, positioning information, neighbor information, composition of matter information, optical transmission information, optical absorption information, other optical characteristics information, a description of the polygon's connection to or association with other polygons, whether adjacent, or in some other location of interest, and any other such information. In this way, and to a reasonable computing level, every aperture, protuberance, crack, crevice, angle, and other characteristic of the disinfection chamber will be represented in the virtual interior volume 112M of the disinfection chamber model 110M.

For the avoidance of doubt, it is further understood that the mathematical mapping of every portion of the virtual interior volume 112M of the disinfection chamber model 110M may be realized as a set of software rules or programming code that represents the travel of disinfecting radiation within the disinfection chamber model 110M. The software rules may represent one or more radiation sources capable of emitting disinfecting radiation within the virtual interior volume 112M of the disinfection chamber model 110M. For each source, any number of virtual "rays" of radiation may be formed, and each of the formed virtual rays may have a set of parameters, rules, data values, formulae, or other such characteristics of operation (i.e., transmission, travel, and termination). In at least some cases, each virtual ray is represented by an intensity value, a radial angle of emission, and associated rules for propagation of the virtual ray, diffusion of the virtual ray, absorption of the virtual ray, reflection of the virtual, and the like. These rules for propagation, diffusion, absorption, reflection, and the like are applied when a particular virtual ray is mapped within the virtual interior volume 112M of the disinfection chamber model 110M. In some cases, the virtual ray is reflected off a surface of the disinfection chamber model 110M or target article model 240M (FIG. 6C). In these or other cases, the virtual ray is diffused, absorbed, or extinguished after traveling a determined distance.

FIG. 6C illustrates one method of forming a target article model 240M. Along the lines of the disinfection chamber model 110M of FIG. 6B, the target article model 240M is formed by arranging a plurality of virtual polygons to cover every surface or otherwise fill the entire virtual volume of the target article model 240M. The virtual polygons in the sequence (a) to (l) of FIG. 6C are uniformly sized cubes, but in other cases, the virtual polygons may have any desirable size and shape. Different virtual polygons may have different sizes, different shapes, or different sizes and shapes. In some cases, for example, the virtual polygons are arranged as triangles, quads, n-gons, or some other shape arranged to virtually cover the surface of a three dimensional object such as the target article, radiation sources in the chamber, chamber wall, positioning structures (e.g., handers, shelves, clips, or the like), sensors, standoffs, or any other object.

Also along the lines of forming the disinfection chamber model 110M in FIG. 6B, the sequence (a) to (l) of FIG. 6C illustrates a single virtual polygon (i.e., a cube) moving through the virtual target article 240M. The sequence of virtual polygon formation and placement in FIG. 6C is helpful for understanding that virtual polygons will desirably cover every surface or otherwise fill the entire space of the virtual target article model 240M, but the sequence is not limiting. Any number of different patterns or algorithms, which may be sequential, concurrent, or otherwise, may be used to create the virtual polygons of the target article model 240M.

The formation of virtual polygons in the target article model 240M of FIG. 6C creates a mathematical mapping of every portion of the virtual surface of the target article model 240M. Along the lines of forming a three-dimensional (3D) model of a disinfection chamber as described herein, the mathematical mapping of a target article may be referred to as a 3D map, a 3D model, a multi-dimensional model, or the like. In some cases, voxels may be defined or otherwise employed to resolve the volume. In other cases, two dimensional (2D) "pixels" or other such units may be employed to describe/resolve a surface. Each virtual polygon may be co-related with adjacent polygons, nearby polygons, and other polygons having particular mathematical relationships or positions. Each virtual polygon may be associated with a computing structure that stores information about the three-dimensional space represented by the corresponding polygon. The computing structure may, for example, store size information, shape information, angle information, positioning information, neighbor information, composition of matter information, and any other such information. In this way, and to a reasonable computing level, every aperture, protuberance, indentation, cavity, groove, standoff, coupling, curve, and other topological characteristic of the target article model 240M will be represented. In the present disclosure, the surface topology is discussed. In other contexts, local material properties, optical properties, or other properties relevant to the model representation could be determined with a sensing means during scanning.

FIGS. 7A to 7G are modeled representations of disinfection chambers and various target articles in a number of configurations. FIGS. 7A to 7G may be collectively referred to herein as FIG. 7.

Figure 7A:
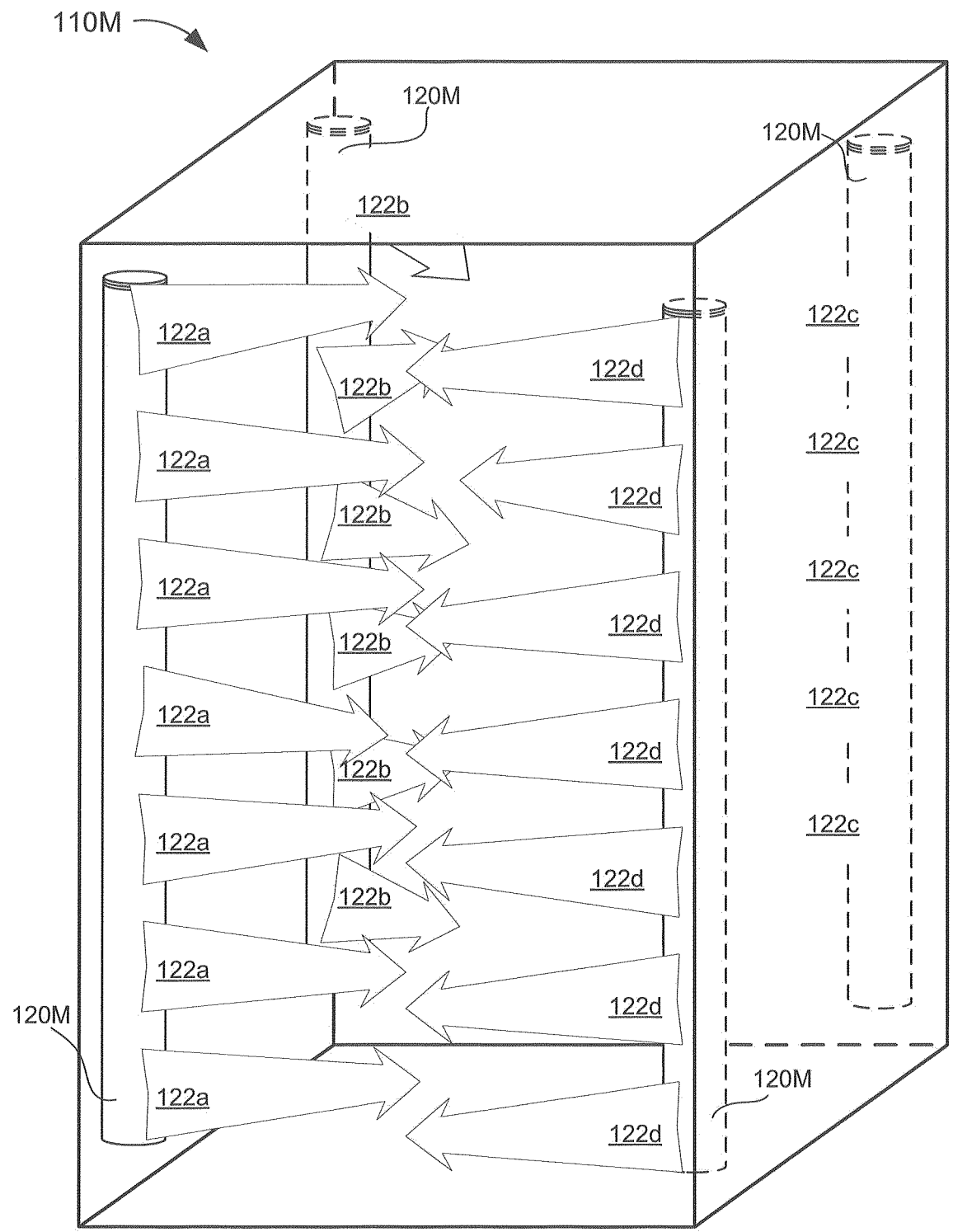
FIG. 7A is a representation of radiation emitted from virtual radiation sources into the virtual interior volume of the disinfection chamber model.

FIG. 7A is a representation of radiation 122a-122d emitted from virtual radiation sources 120M into the virtual interior volume 112M of the disinfection chamber model 110M. Radiation 122a is emitted from a first radiation source 120M, radiation 122b is emitted from a second radiation source 120M, radiation 122c is emitted from a third radiation source 120M, and radiation 122d is emitted from a fourth radiation source 120M. More or fewer radiation sources 120M, in similar or different locations and orientations in the disinfection chamber model 110M could also have been modeled. FIG. 7A shows that when the radiation sources 120M are energized, each radiation source 120M will operate as directed and in accordance with its own parameters and characteristics. The radiation emitted into the chamber will be optically acted on by structures inside the disinfection chamber such as walls, hangers, bases, corners, other radiation sources, and the like.

In some cases, the radiation emitted into the disinfection chamber model 110M may be traced with a "ray tracing" computer program such as OPTICSTUDIO by ZEMAX, CODE V by SYNOPSIS, or OSLO by LAMBDA RESEARCH. The ray tracing program may be used to map simulated radiation rays, and the information from the program can be used to produce any number of radiation intensity maps. These radiation intensity map embodiments, which are formed utilizing information from the ray tracing program, may have the same or different parameters, data fields, structures, formatting, or the like as the radiation intensity maps created using actual disinfection chambers and on-board radiation measuring sensors. Along these lines, radiation intensity map embodiments formed based on ray tracing program information may also be adjusted with calibration values, scaling values, or the like. These adjustments may be based on radiation measured in a disinfection chamber or alternatively, based on modeled data (e.g., a model of a target article, a model of a radiation source, or the like).

Figure 7B:
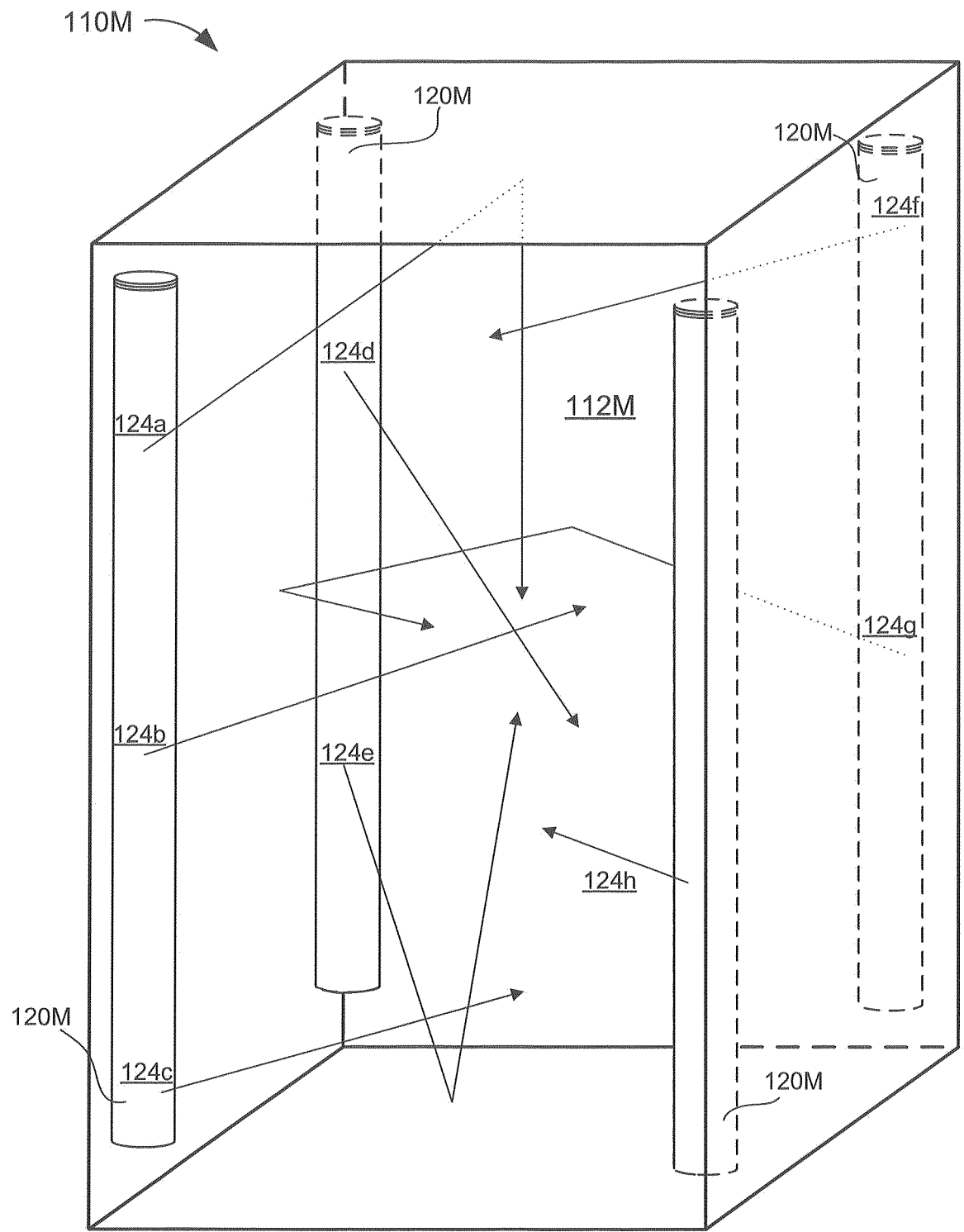
FIG. 7B is a modeled representation of radiation vectors formed in the virtual interior volume of the disinfection chamber model.

FIG. 7B is a modeled representation of radiation vectors 124a-124h, or "rays," formed in the virtual interior volume 112M of the disinfection chamber model 110M. The representation of FIG. 7B is created using the model of the virtual interior volume 112M of the disinfection chamber model 110M and known characteristics of modeled radiation sources 120M, which may be inferred, based, or otherwise calculated from any number of sources including radiation maps formed from measured radiation data (e.g., FIG. 5), a ray tracing program, or some other like source. Support for the accuracy of the modeled radiation vectors comes from empirical test measurements in real disinfection chambers 100 that operate real radiation sources 120 and collect real measurements with sensors 130 (e.g., FIG. 5). FIG. 7B shows a very small number of radiation vectors so as to not overly complicate the drawing. It is understood that hundreds, thousands, and even millions of radiation vectors (e.g., rays) can be modeled, and their evolution history can be calculated as the vectors interact with the disinfection chamber 100 and the contents therein.

In FIG. 7B, a first modeled radiation vector 124a is produced and emitted from a first modeled radiation source 120M into the interior volume 112M. The first modeled radiation vector 124a is originally directed toward the interior top of the disinfection chamber 110M. After contacting the disinfection chamber 110M interior top, the radiation vector is then reflected downward, toward the bottom of the disinfection chamber 110M.

A second modeled radiation vector 124b is produced and emitted from the first modeled radiation source 120M toward the center of the modeled interior volume 112M.

A third modeled radiation vector 124c is produced and emitted from the first modeled radiation source 120M. The third modeled radiation vector 124c is also directed toward the lower center of the modeled interior volume 112M.

A fourth modeled radiation vector 124d is produced and emitted from the second modeled radiation source 120M toward the center of the modeled interior volume 112M. The second modeled radiation vector 124b and the fourth modeled radiation vector 124*d* cross nearby each other in the modeled interior volume 112M.

A fifth modeled radiation vector 124*e* is produced and emitted from the second modeled radiation source 120M into the interior volume 112M. The fifth modeled radiation vector 124*e* is originally directed toward the interior bottom of the disinfection chamber 110M. After contacting the disinfection chamber 110M interior bottom, the fifth modeled radiation vector is then reflected upward, toward the top of the disinfection chamber 110M, but first passing through the center of the modeled disinfection chamber 110M.

A sixth modeled radiation vector 124*f* is produced and emitted from a third modeled radiation source 120M toward the center of the modeled interior volume 112M.

A seventh modeled radiation vector 124*g* is produced and emitted from the third modeled radiation source 120M. The seventh modeled radiation vector 124*g* is directed toward, and reflects off of, a back wall of the modeled disinfection chamber 110M. After reflecting off of the back wall, the seventh modeled radiation vector 124*g* is directed toward, and reflects off of, a left sidewall of the modeled disinfection chamber 110M An eighth modeled radiation vector 124*h* is produced and emitted from a fourth modeled radiation source 120M toward the center of the modeled interior volume 112M.

Modeled radiation vectors 124*a*-124*h* can be modeled according to any desirable characteristics of the radiation, the chamber, target articles, or any other structures. Reflection, absorption, re-emission, and any other such factors may be suitably modeled, particularly to represent actual radiation, delivered by actual radiation sources, into an actual disinfection chamber.

Figure 7C:
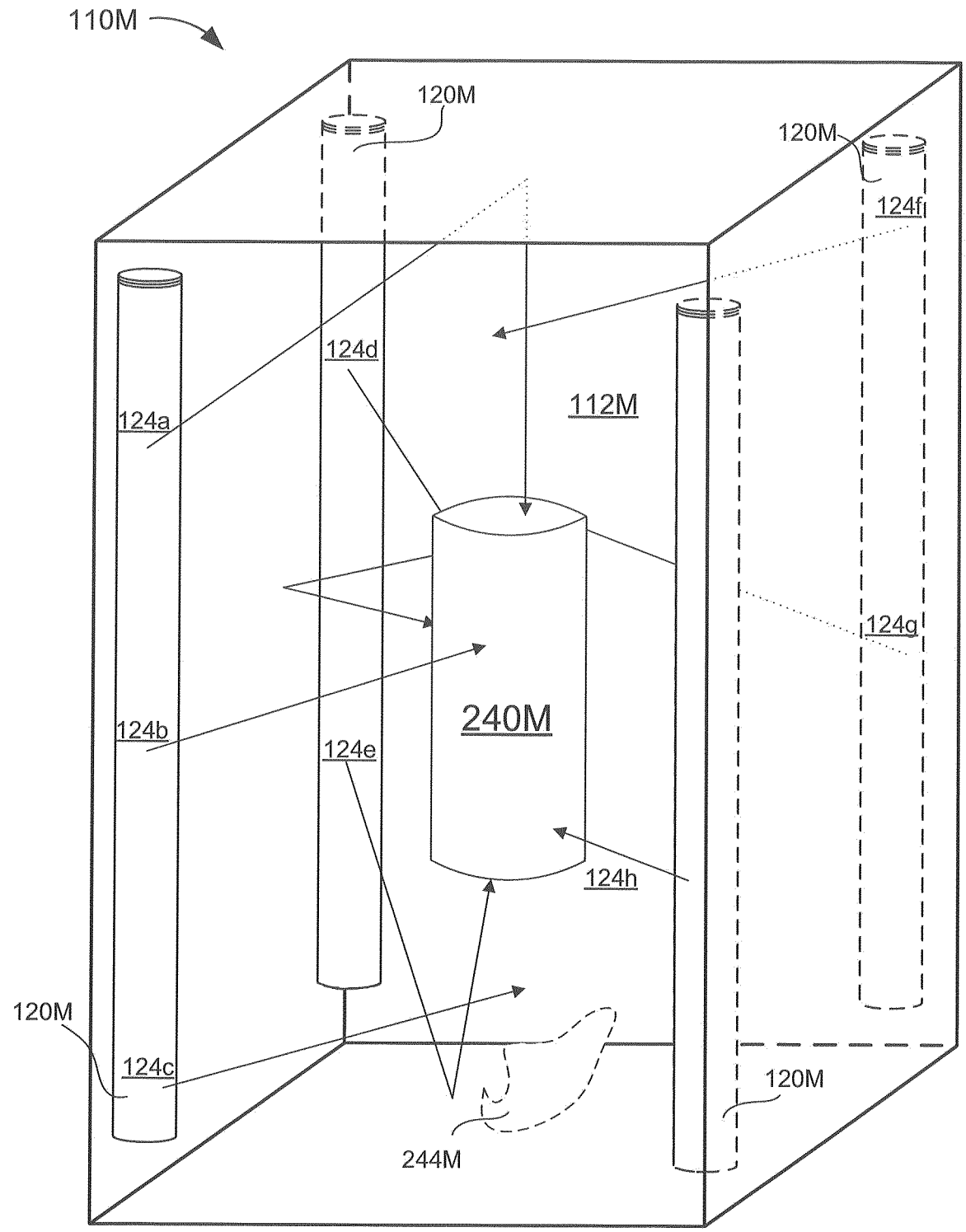
FIG. 7C is another modeled representation of radiation vectors formed in the virtual interior volume of the disinfection chamber model.

FIG. 7C is another modeled representation of radiation vectors formed in the modeled virtual interior volume 112M of the disinfection chamber model 110M. In the model of FIG. 7C, a target article model 240M (FIG. 6C) have been virtually placed in the interior volume 112M. Additionally, so as to disclose the nature of the model represented in FIG. 7C, the same modeled radiation vectors 124*a*-124*h* of FIG. 7B are also represented in FIG. 7C a modified way.

As evident in FIG. 7C, the first modeled radiation vector 124*a* no longer reaches the center of the interior volume 112M. Due to the placement of the target article model 240M, the first modeled radiation vector 124*a* emits from the first modeled radiation source 120M, reflects from the interior top of the disinfection chamber model 110M, and strikes the top of the target article model 240M. In the model, this transfer of energy to the target article model 240M is recorded. Along these lines, the second modeled radiation vector 124*b* emits from the first modeled radiation source 120M and also strikes the target article model 240M. The third and sixth modeled radiation vectors 124*c*, 124*f* are not affected by the presence of the target article model 240M. The fourth, fifth, seventh, and eighth modeled radiation vectors 124*d*, 124*e*, 124*g*, and 124*h* are affected by, and strike, the target article model 240M. Via modeling of dozens, hundreds, thousands, and even millions of vectors, embodiments described in the present disclosure are capable of modeling the radiation that strikes a target article model 240M with substantial accuracy. In some cases, some number (e.g., thousands, hundreds of thousands, millions, etc.) of rays are "released" over a period of time, Interaction histories are sequentially or otherwise tracked as the rays reflect and/or get absorbed. Eventually the simulation converges in such a way that a stable set of values, which may, for example, represent power levels one, some, or even all locations of interest. When this stability is deemed to have been reached, it is determined that the model has been exercised sufficiently to characterize the model of interest.

As evident in the description, particularly of FIGS. 5 to 7, it is shown that an actual disinfection chamber of any size, shape, dimension, interior structures, and any other characteristics can be modeled, and radiation sources can be modeled. The modeling of the radiation sources can operate dynamically to adjust radiation vectors in any suitable way to simulate a radiation source of any dimension, location, orientation, power, age, cleanliness (e.g., dirtiness, representation of radiation blocking caused by contaminants or other foreign material on the surface of the radiation source, and the like), temperature, time duration of operation, time within the disinfection cycle (e.g., within the first second of starting a disinfection cycle, within the first 10 seconds, within the first 30 seconds, after 60 seconds, and the like), and any other such factors. Such modeling of the disinfection chamber and radiation sources can be used to create a radiation intensity map.

In addition, as also evident in the description, particularly of FIGS. 5 to 7, it is shown that any type of actual target article 240 can be modeled (i.e., target article model 240M), and the accrual of radiation impinging on the surface of the target article in an actual disinfection chamber 110 can be modeled. The amount of radiation absorbed may also be calculated based on the physical and optical properties of the target surface. The creation of radiation maps based on or otherwise derived from actual data collected from one or more sensors 130 and one or more target article sensors 130*a*, 130*b* can be used to confirm and validate the models or otherwise adjust radiation maps produced by the models. In this way, time consuming, tedious, and expensive physical modeling of actual disinfection chambers and actual target articles can be avoided, expedited, or otherwise rendered more efficiently.

Target objects may have particularly small features or odd shaped geometry for which instrumentation with optical detectors for direct measurement of incident power and/or dose is not practically feasible. On the other hand, by applying the inventive approaches discussed in the present disclosure, acceptable correlation of modeled results with physical measurements can provide an improved confidence that the radiation reaching exposed surfaces of a new candidate object may be calculated with acceptable accuracy, and hence the local dose of radiation received at each portion of the target object may also be calculated without requiring direct measurement.

FIG. 7C also shows a modeled foreign object 244M in the disinfection chamber model 110M. The modeled foreign object 244M may represent a surgical glove, a sterile wipe, a label, secondary object that a medical practitioner places in the chamber, or any other type of foreign object, which occasionally occurs in a medical setting. While the modeled foreign object 244M does not directly affect any of the radiation vectors that directly strike the target article model 240M, it is evident that the modeled foreign object 244M may have reflective, absorptive, diffusive, or other optical properties that can affect the radiation vectors 124*a*-124*h*. Accordingly, a modeled foreign object 244M of any size, shape, dimension, location, orientation, and other characteristics may be optionally modeled.

In some cases, an actual disinfection chamber may include one or more foreign object detection sensors 132. In these embodiments, the foreign object detection sensors 132 may include any number of infrared transmitters and infrared detectors, any number of load cells (e.g., to detect an unexpected weight due to a foreign object, a probe placed on a chamber floor instead of suspended, or the like), any number of camera devices, or the like. Such foreign object sensors may be cooperatively coupled to an integrated or remote controller 140 (FIG. 2) executing an appropriate algorithm.

Figure 7D:
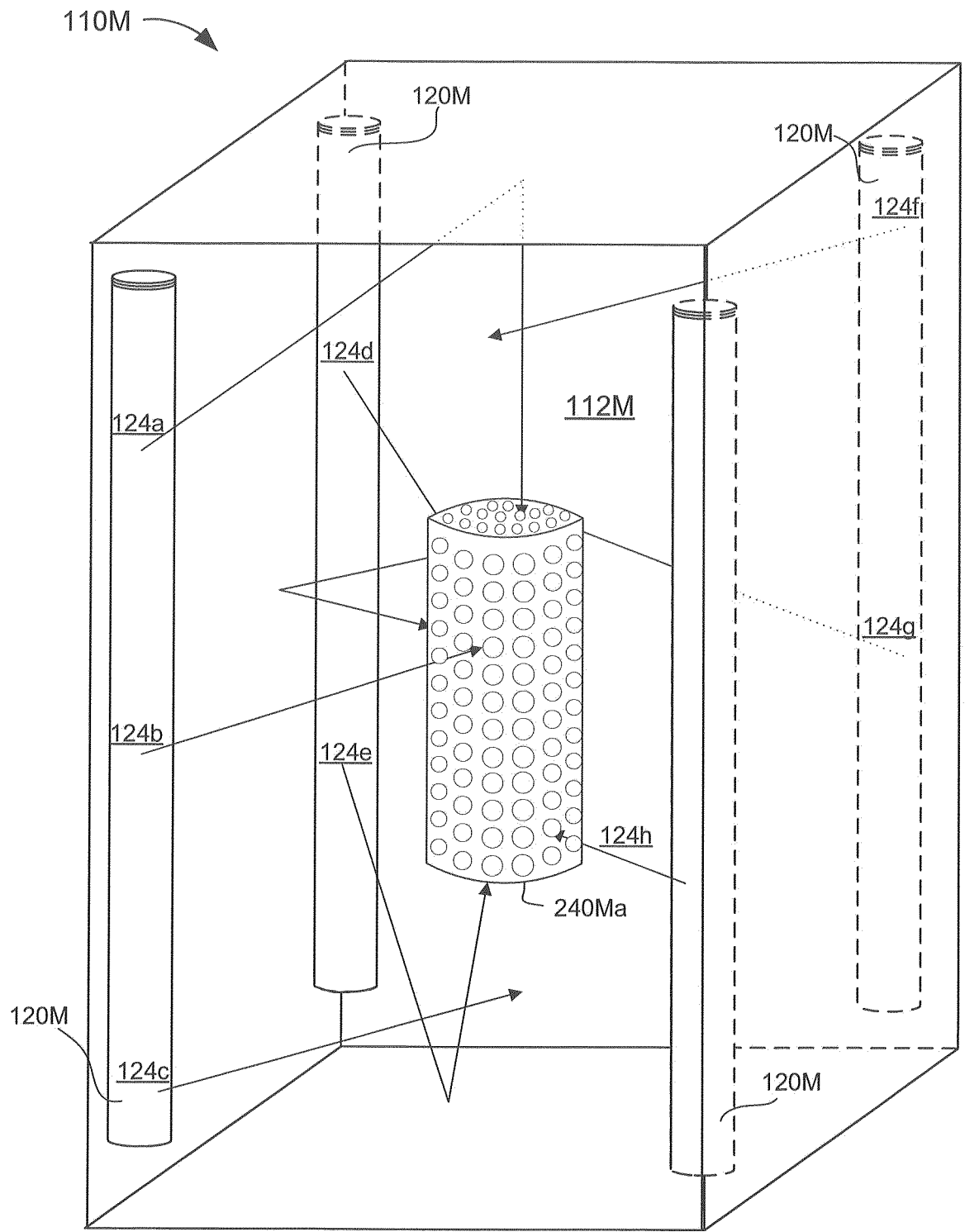
FIGS. 7D to 7E are modeled representations of radiation vectors formed in the virtual interior volume of the disinfection chamber model when a target article model of a target article calibration device is present.
Figure 7E:
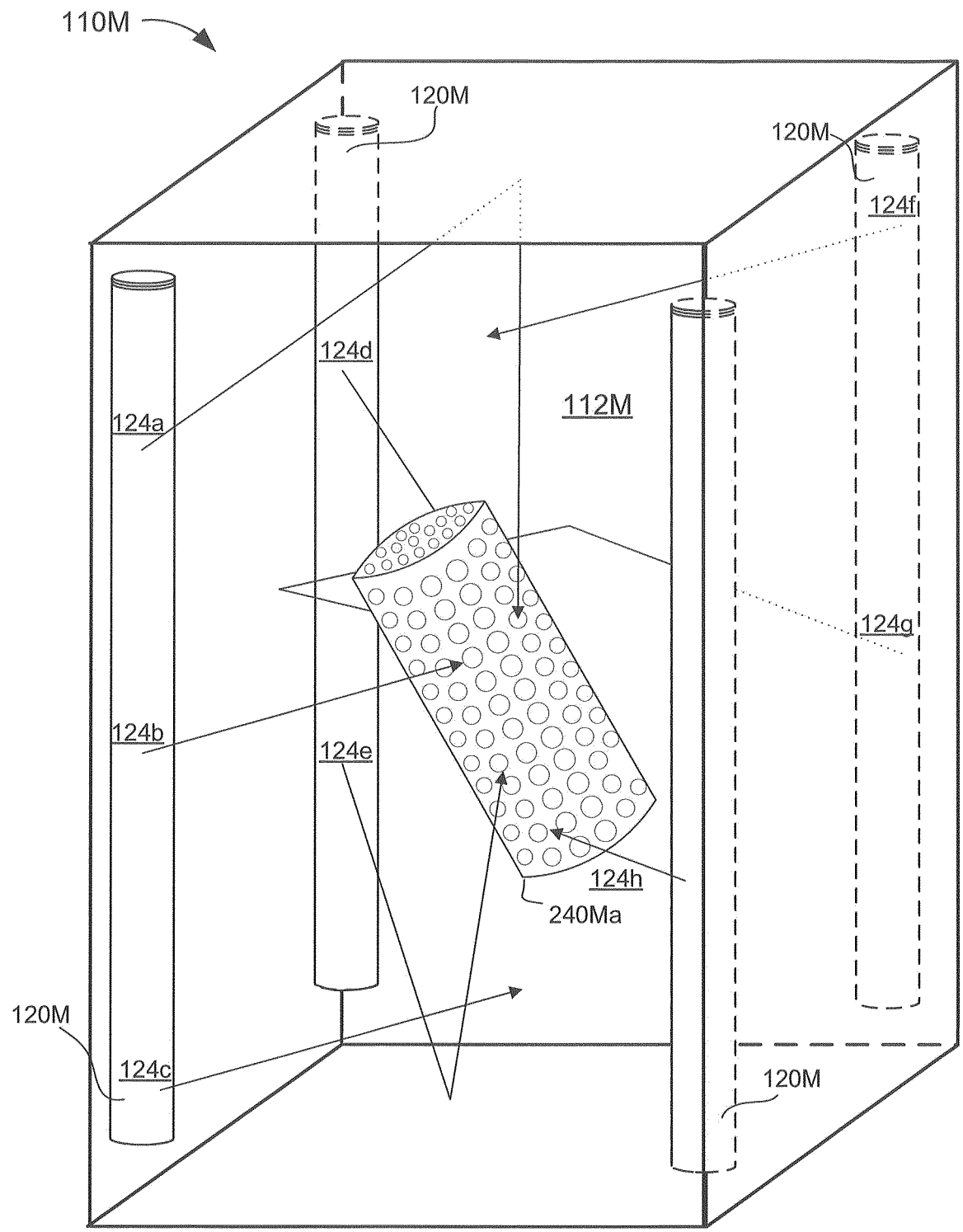

FIGS. 7D to 7E are modeled representations of radiation vectors 124a-124h formed in the virtual interior volume 112M of the disinfection chamber model 110M when a target article model 240Ma of a target article calibration device is present. The modeled effect on radiation vectors 124a-124h is evident in figures as the position and orientation of the target article model 240Ma changes.

The models of FIGS. 7D and 7E are representative of the embodiments of FIGS. 5C and 5D. By modeling the calibration article of FIGS. 5C, 5D, which can measure radiation in real time in an actual disinfection chamber, the modeling of radiation vectors can be made even more accurate. That is, the programming that performs the modeling can receive feedback to adjust models of radiation measurements captured with on-board sensors 130 and target article sensors 130a, 130b.

Figure 7F:
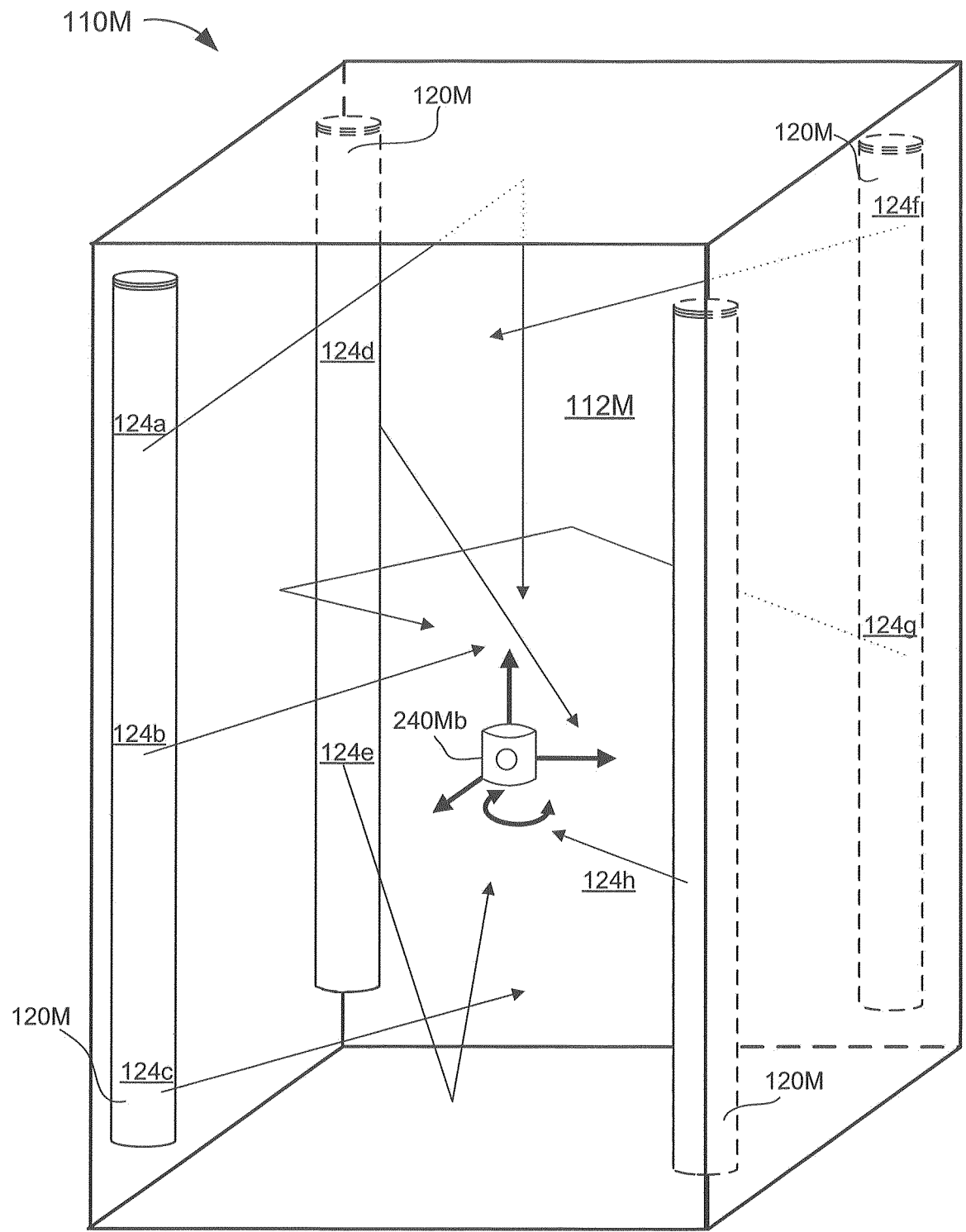
FIG. 7F is a modeled representations of a disinfection chamber model along the lines of FIG. 5E.

FIG. 7F is a modeled representation of a disinfection chamber model along the lines of FIG. 5E. That is, in FIG. 5E, an actual target article calibration device 240b is used to capture radiation measurements in a disinfection chamber 110. The target article calibration device 240b may be robustly controlled to capture a substantial number of radiation data measurements in nearly every portion of the disinfection chamber, and a nearly every permutation of radiation source operations. In FIG. 7F, the target article calibration device 240b of FIG. 5E is modeled as a target article calibration device model 240Mb.

FIG. 7G shows various exemplary models of radiation vectors formed in a disinfection chamber model 110M when a certain target article model is present. In FIG. 7G(a), a target article model 240Mc is represented in a first position of the disinfection chamber model 110M, and in FIG. 7G(b), the same target article model 240Mc is represented in a second position of the disinfection chamber model 110M. In FIG. 7G(c), an elongated, slender target article model 240Md is represented in the disinfection chamber model 110M, and in FIG. 7G(d), a non-symmetric target article model 240Me is represented in the disinfection chamber model 110M. FIG. 7G shows that in any modeled disinfection chamber, having any modeled radiation sources, a target article of any size, dimension, material or materials, position, orientation, shape or shapes, contours, cracks, crevices, protuberances, apertures, and any other characteristics can be modeled.

Figure 8:
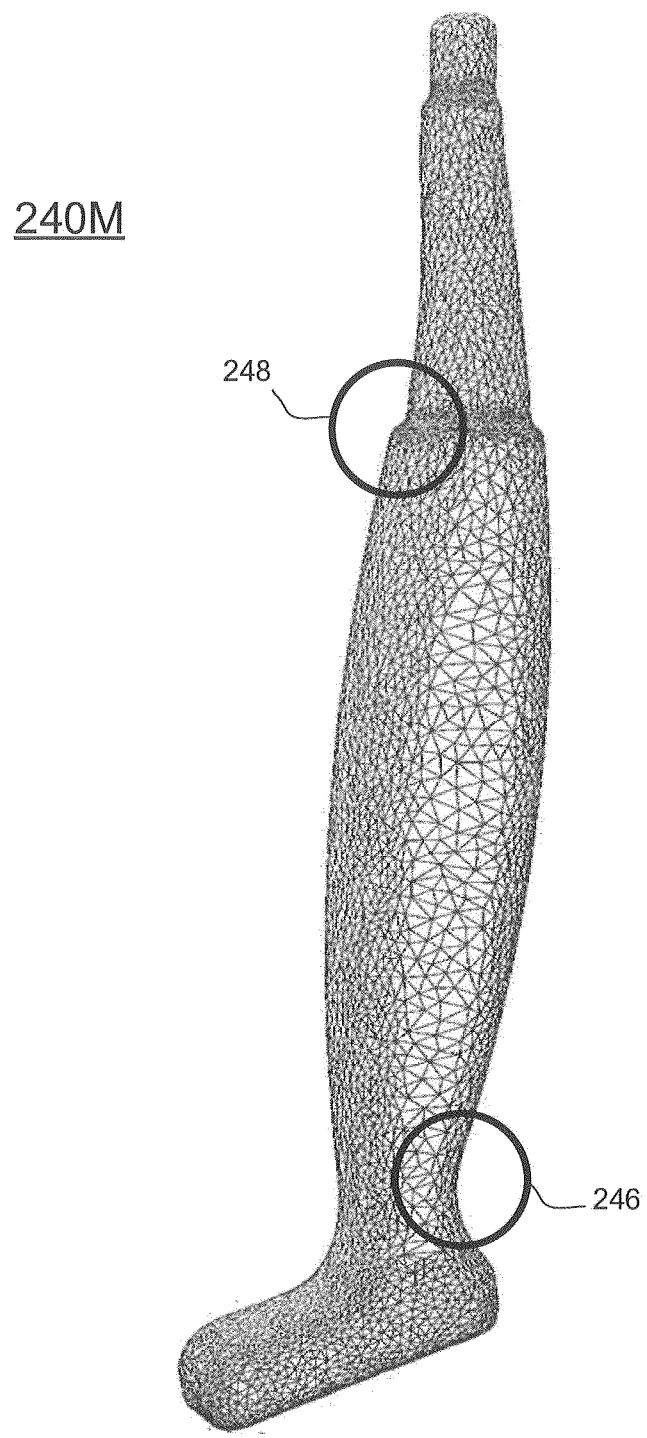
FIG. 8 is a target article model in more detail.

FIG. 8 is a target article model 240M in more detail. The target article model 240M of FIG. 8 may be generated along the lines of FIGS. 5-7.

The target article model 240M of FIG. 8 represents a conventional endocavity ultrasound probe, but any other target article (e.g., medical device) may be modeled according to the principles and teachings of the present disclosure. The surface of the target article may have dimples, contours, cracks, crevices, apertures, protuberances, registration features, connectors, or the like. The surface may be modeled having a range (e.g., 0 to 255) of reflectivity, a range (e.g., 0 to 255) of absorption, and similar ranges of diffusion and any other optical properties. The ranges may be expressed as a linear or non-linear range of the particular property from a lowest useful range to a greatest useful range. Units for such ranges may include any useful unit associated with the particular property. For example, in some cases, ranges of reflectivity and ranges of absorption may be expressed as a percentage of incoming energy versus outgoing (i.e., reflected or absorbed as the case may be) energy.

The target article model 240M of FIG. 8 is formed by arranging a plurality of virtual two dimensional (2D) polygons (e.g., a "mesh") to cover the entire virtual surface of an initial target article model 240M. The virtual polygons are not uniformly sized or shaped, but each polygon may be referred to as a triangle. The virtual polygons have any desirable size and shape to form the virtual surface of the model with substantial accuracy.

The formation of virtual polygons in FIG. 8 creates a mathematical mapping of every portion of the target article model 240M surface. Each virtual polygon may be co-related with adjacent polygons, nearby polygons, and other polygons having particular mathematical relationships, positions, and orientations. Each virtual polygon may be associated with one or more dedicated computing structure, shared computing structures, or computing structures that have both dedicated portions and shared portions. The computing structures store information about the portion of the surface of the target article model 240M that is represented by the corresponding polygon.

Computing structures associated with any one or more polygons may, for example, store size information, shape information, angle information, positioning information, neighbor information, composition of matter information, and any other such information. The computing structures may also store information regarding how radiation will impact the represented surface. This "surface representation" information may include reflectivity, absorption, diffusion, temperature, and the like. The surface representation information may also include information that indicates whether or not the corresponding portion of a surface (i.e., region of interest) is in a hot spot, a cold spot, or a spot of uniform irradiation. The storage repository associated with an indicator of the type of surface (e.g., hot spot, cold spot, or spot of uniform radiation) may also store corresponding information associated with the source of radiation, direction of radiation, orientation of the target article model 240M within the disinfection chamber, the degree (e.g., 0 to 255) to which a hot spot is "hot," the degree to which a cold spot is "cold," and the like. In this way, the "indicator of the type of surface" information may be more accurately represented in a radiation intensity map and in a generated disinfection program.

The target article model 240M of FIG. 8 identifies various regions of interest including one hot spot 246 and one cold spot 248. The hot spot 246 may represent a single point, a plurality of points, or a region. Along these lines, a cold spot 248 may represent a "coldest" spot, a region at or around the "coldest" spot, a plurality of cold spots, or some other like point or region. Any other of number of hot spots and cold spots, or no hot spots or cold spots could also be identified in the target article model 240M. Along these lines, any number of hot spots 246 or cold spots 248 may also be identified on an actual target article 240.

The hot spot 246 in FIG. 8 may be determined for any number of reasons. In one case, for example, the contours of the target article model 240M, and the material represented in this portion of the target article model 240M may cause a point of focal reflection to be concentrated at the hot spot 246. This hot spot may be associated with information identifying the source of radiation, the direction from which the radiation comes, and other such factors. Accordingly, the information may be formed as a scaling factor, an attenuation value, or the like that represents how much the intensity of radiation will increase at the identified hot spot and under what conditions. This information is used when a disinfection system is modeled according to a particular disinfection chamber model 110M when the target article model 240M device is present. This information is then also used when a disinfection program is generated. In this way, when the generated disinfection program is executed by a disinfection chamber 110, then a target article 240 of the type represented by the target article model 240M will be disinfected with substantial confidence that the region of interest (i.e., hot spot) was not over-radiated beyond its minimum dose.

The cold spot 248 of FIG. 8 may be determined for any number of reasons. Different contours, for example, of the target article model 240M, and the material represented in this portion of the target article model 240M may cause a point on the target article surface where radiation fails to reach or reaches level that is below a uniform radiation of the device. Along the lines of the hot spot, the cold spot may be associated with information identifying the source of radiation, the direction from which the radiation comes, and other such factors. The cold spot information may be formed as a scaling factor, an attenuation value, or represented in some other way indicates how much the intensity of radiation will decrease at the identified hot spot under some or all conditions. This information is used when a particular disinfection chamber model 110M and target article model 240M are analyzed. This information is then also used when a disinfection program is generated. In this way, when the generated disinfection program is executed by a disinfection chamber 110, then a target article 240 of the type represented by the target article model 240M will be disinfected with substantial confidence that the region of interest (i.e., cold spot) received a sufficient minimum dose of radiation.

III. Example Process

Figure 9A:
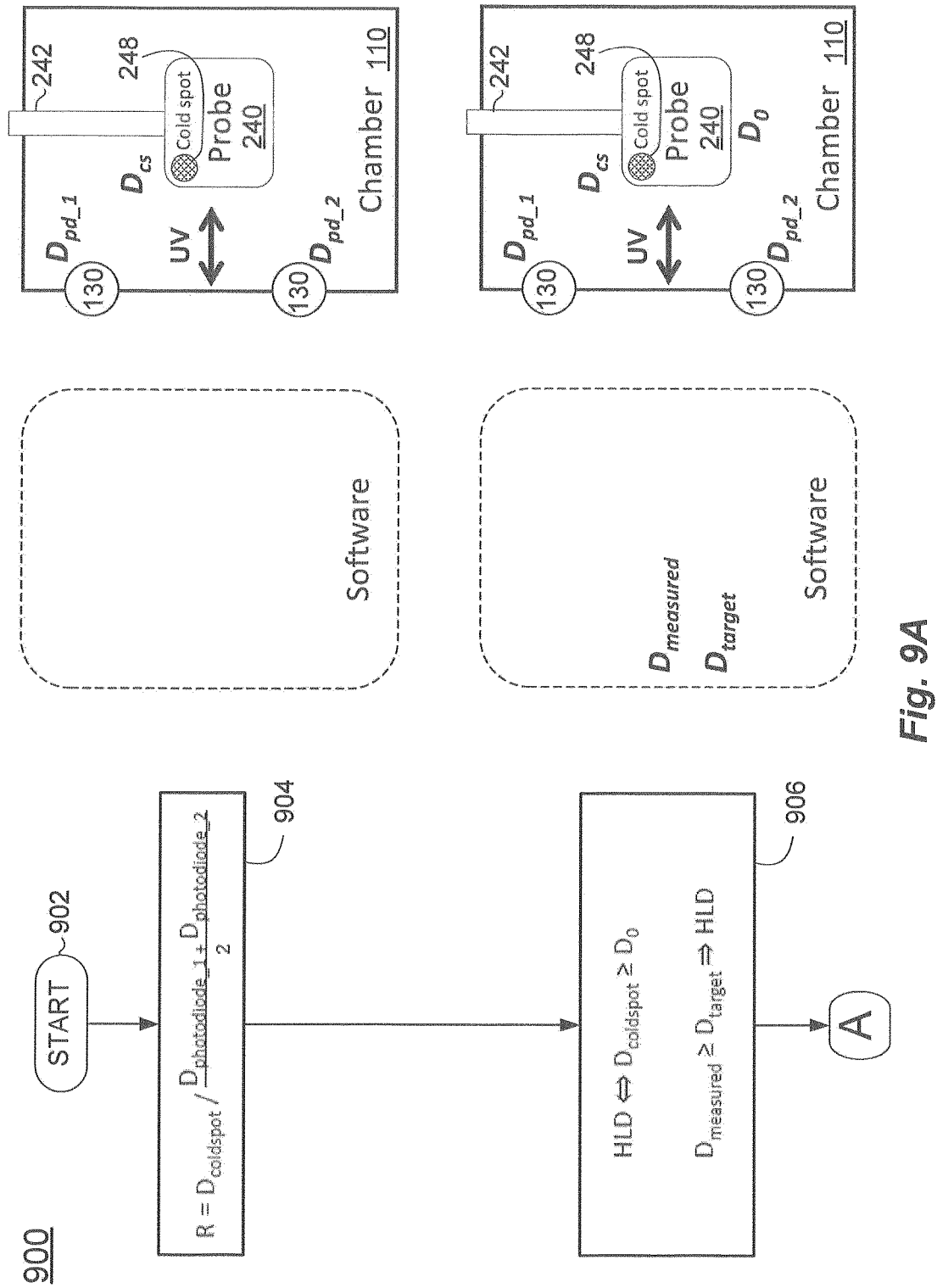

FIGS. 9A to 9D are a data flow diagram 900 representing a minimum dose determination procedure. FIGS. 9A to 9D may be referred to collectively as FIG. 9. The data flow diagram 900 of FIG. 9 begins in FIG. 9A and ends in FIG. 9D. The data flow diagram 900 passes through FIG. 9 via off-page references "A," "B," and "C" (FIGS. 9A, 9B, and 9C) and respectively corresponding on-page references "A," "B," and "C" (FIGS. 9B, 9C, and 9D). Nevertheless, it is understood that the acts disclosed in the data flow diagram 900 may be optional and may be performed in any order. What's more, these acts may be performed in the disinfection system 100, in a remote computing device, or in any combination of local or remote computing devices.

In FIG. 9, embodiments of a particular disinfection chamber 110 are shown in various states of operation. The chamber may include sensors 130 (e.g., photodiodes), a target article position device arranged as a suspension assembly 242 holding a target article 240 (e.g., a probe or a target article calibration device 240a, 240b), and an exemplary cold spot 248 of the target article 240. Various states of the disinfection chamber 110 and associated "software" are illustrated proximate to certain calculations performed in generation of the minimum dose.

In FIG. 9, "software" is presented in a dashed line container. The software of FIG. 9 may be integrated or otherwise cooperative with controller 140 (FIG. 1). In addition, or in the alternative, the software of FIG. 9, as with other software and algorithmic operations of the present disclosure, may be stored, executed, or stored and executed remote to the controller 140. Operations of the software of FIG. 9 to determine a minimum dose are now further described.

Execution begins at 902.

As described in the present disclosure, target articles may include any number of regions of interest such as cold spots, hot spots, and uniformly irradiatable surfaces. Because a minimum dose calculation is formulated to deliver sufficient radiation into chamber 110 to reduce the population of undesirable biological pathogen on the surface of the target article by a determined acceptable amount, an aggregated minimum dose is generated with recognition that radiation delivered to the cold spots of the target article are particularly relevant. Along these lines, it may also be recognized that by delivering the minimum dose to a "coldest" cold spot of the target article, then a minimum dose will also be delivered to each other cold spot of the target article 240 as well as to each other surface of the target. The cold spot 248 of FIG. 9 may therefore represent a "coldest" cold spot of the target article 240.

In a disinfection chamber 110, an amount of radiation dose measured at sensors 130 may be used to infer or otherwise determine how much of a radiation dose is delivered to a particular region of interest (e.g., cold spot 248) on the surface of a target article 240. It may then be presumed that the dose of radiation received at the surface of the target article 240 can be inferred or otherwise determined by a calculated average of the radiation dose measured at any one of the sensors 130. Such calculated average radiation dose may be generated by summing the dose measured at all of the sensors 130 and dividing the sum by the total number of sensors 130.

Since it has further been determined, however, that not every surface of the target article receives the full dose of radiation, a calculation of a minimum dose requires more than simply determining the radiation dose average measured at the sensors 130. Instead, since a cold spot may receive less radiation (i.e., a lower dose) than other areas on the surface of the target article 240, it is beneficial in the generation of the minimum dose to understand a unit-less ratio between the radiation dose received at the cold spot 248 and the radiation dose received at other portions of the target article surface, for example at the surface of a sensor 130.

The ratio determined at 902 may represent a factor (e.g., a scaling factor, a weighting factor, or the like) applied to information that represents a dose of radiation measured by sensors 130 in order to determine that a minimum dose of radiation has been delivered to the cold spot of article 240. A different ratio is typically generated for each target article 240.

By way of example, the ratio (R) determined at 902 may be understood as representing how much more radiation must be delivered to the target article 240 to ensure with sufficient confidence that the minimum dose has been delivered to all surfaces of the target article 240, including cold spot 248. A ratio (R) of two (2), for example, may indicate that only half of the average radiation received at sensors 130 is received at cold spot 248; a ratio of three (3), for example, may indicate that only one third of the average radiation received at sensors 130 is received at cold spot 248; and a ratio of one point five (1.5), for example, may indicate that only two thirds of the average radiation received at sensors 130 is received at cold spot 248. Other ratio values may of course be determined.

It is also recognized that a corresponding ratio may also be determined for each hot spot of a target article. In this way, a "hottest" hot spot is also particularly relevant. By understanding how much radiation is received at a hot spot, the timed delivery of a minimum dose of radiation may be adjusted so as to avoid or otherwise reduce the negative effects of over-radiating a target article 240.

At 904, in the disinfection chamber 110, a dose (D) of radiation received at any number of sensors 130 may be representative of an amount of radiation (UV) received at a surface of interest on a target article 240. A ratio between the radiation dose received by the cold spot 248 and the average of the radiation doses received by sensors 130 in chamber 110 is determined as in Equation 1. Any number of sensors (n) may be accounted for as determined by the particular disinfection chamber 110 of interest.

$$\text{Ratio }(R) = \frac{D_{coldspot}}{\frac{(D_{photodiode\_1} + D_{photodiode\_2} + D_{photodiode\_n})}{n}} \quad \text{(Eq. 1)}$$

At 904, within the disinfection chamber 110, $D_{pd\_1}$ represents the dose of radiation received at a first sensor 130, $D_{pd\_2}$ represents the dose of radiation received at a first sensor 130. These doses are represented in the illustrated equation as $D_{photodiode\_1}$ and $D_{photodiode\_2}$. The dose of radiation at cold spot 248 within the disinfection chamber is represented as $D_{\_cs}$ and represented in the illustrated equation as $D_{\_cs}$. It is recognized that this simple averaging is one simple way to combine these detected measurements. In other cases, the values read from one or more sensors may be subjected to adjustment via calibration factors. For example, other methods of calibration, "filtering" (e.g., applying a mathematical algorithm that can account for other factors and can include data from prior time steps, estimating values from a predictive model that "looks into the future," providing other corrections that result from measured or calculated input information, etc.) may also be employed.

At 906, the concept of high-level disinfection (HLD), as introduced and discussed in the present disclosure, is recognized. To achieve HLD of a target article 240 is to provide a log reduction in viability of at least a determined amount (e.g., $10^4$, $10^5$, $10^6$, or some other amount) of one or more specified microorganisms on a cold spot 248 of a target article 240. Achieving this target reduction is represented in Equation 2 wherein a radiation dose at a cold spot 248 ($D_{coldspot}$) exceeds a determined threshold minimum dose of radiation ($D_0$).

$$\text{HLD} \Leftrightarrow D_{coldspot} \geq D_0 \quad \text{(Eq. 2)}$$

In practice, accumulating a measured dose of radiation ($D_{measured}$), until it exceeds a target dose of radiation ($D_{target}$), leads to a determination that HLD has been achieved. In at least one case, the target dose of radiation ($D_{target}$) is expressed in terms or units of mJ/cm². This value may be expressed as an area-specific dose that enables computation of the dose to a region of a given area or extent. Additionally, this value may represent a small- (i.e., a so-called "differential element of area"), medium-, or large-sized area relative to the overall extent of a target object. In these cases, it may be predicted or otherwise expected that the irradiance is likely not uniform over all regions that make up the target article 240.

In processing at 908, in FIG. 9B, the target dose of radiation is determined. The target dose of radiation ($D_{target}$) corresponds to HLD achieved at the target cold spot 248. The target dose of radiation ($D_{target}$) is the minimum dose of radiation ($D_0$) scaled by the ratio (R) and further scaled by a safety factor as indicated in Equation 3.

$$D_{target} = \frac{D_0}{R} \times F_{safety} \quad \text{(Eq. 3)}$$

The safety factor of Equation 3 is recognized as a simple multiplication for ease in understanding the present operations. In other cases, the safety factor may include the application of a constant (e.g., a DC offset or an "intercept"), a second-order non-linear scaling, or some other more sophisticated calculations. In these or still other cases, a safety factor may be applied to corrections that are updated in real time based on measurements.

The safety factor is arranged to compensate for the impact of influencing factors on the delivery of radiation to the target article 240. As described herein, the influencing factors are characteristics, parameters, or other such elements that may influence the relationship between radiation measured at a sensor 130 and radiation that impacts the surface of the target article 240. A non-exhaustive, non-limiting list of such factors includes an impact of the repeatability and accuracy of the optical simulations and modeling, an impact of the difference in aging of individual radiation sources 120, an impact of the difference in temperatures of the radiation sources 120, an impact in the uncertainty of placement of the target article 240 in the disinfection chamber 110, an impact of the uncertainty of calibration of a reference standard including drift between a plurality of calibrations, an impact of uncertainties in the calibration procedure, and the like. In at least one case, a safety factor ($F_{safety}$) is estimated as the square root of the sum of a square of each determined impact with an enlargement coefficient of 2 to produce a determined level of confidence of 95%. This may, for example, apply for normally distributed stochastic processes. In other cases, variables that exhibit behaviors better described by other probability distributions may imply other calculations are appropriate.

At 910, the measured dose of radiation ($D_{measured}$) is quantified by application of a calibration factor ($C_{calib}$) as indicated in Equations 4, 5, and 6. The measured dose ($D_{measured}$) is the average dose measured by (n) sensors 130.

$$D_{measured} = \frac{(D_{photodiode\_1} + D_{photodiode\_2} + D_{photodiode\_n})}{n} \times C_{calib} \quad \text{(Eq. 4)}$$

$$\frac{(D_{photodiode\_1} + D_{photodiode\_2} + D_{photodiode\_n})}{n} \times C_{calib} = \frac{D_{coldspot}}{R} \times C_{calib} \quad \text{(Eq. 5)}$$

$$D_{measured} = \frac{D_{coldspot}}{R} \times C_{calib} \quad \text{(Eq. 6)}$$

An exemplary calibration procedure is discussed in the present disclosure and further discussed with respect to 912 and 914. The procedure produces a calibration factor ($C_{calib}$) arranged to scale actual radiation measurements from sensors 130 that are captured during an HLD procedure. The calibration factor ($C_{calib}$) accounts for changes and differences amongst radiation sources 120, time, temperature, age, and other such factors. In Equation 4, a dose of measured radiation ($D_{measured}$) is determined by multiplying an average sensor radiation dose (e.g., an accumulation of radiation measurements from a number (n) of sensors 130 divided by the number of sensors (n)) by the calibration factor ($C_{calib}$). As indicated in Equations 5 and 6, and supported by Equation 1, such measured dose of radiation ($D_{measured}$) is equivalent to the dose of radiation impacting the cold spot 248 of target article 240 ($D_{coldspot}$) scaled by ratio R, and both of these values are scaled by the calibration factor.

At 912 and 914, at least one further embodiment of a calibration process to determine a calibration factor is described. Equations 7 to 10 are presented.

$$D_{photodiode\_1} = Signal_{photodiode} \times Coeff\_calibration\_i \quad \text{(Eq. 7)}$$

$$D_{measured} = D_{solo} \quad \text{(Eq. 8)}$$

$$D_{measured} = \frac{(D_{photodiode\_1} + D_{photodiode\_2} + D_{photodiode\_n})}{n} \times C_{calib} \quad \text{(Eq. 9)}$$

$$C_{calib} = R_{solo} \quad \text{(Eq. 10)}$$

At 912, a calibration process includes iteratively and individually, from 1 to (n), measuring a radiation dose at each sensor 130 ($D_{photodiode\_n}$). The signal created by the calibration dose of radiation ($Signal_{pd\_1}$, $Signal_{pd\_2}$) that is applied in the disinfection chamber 110 and received by each sensor 130 is separately processed. And as indicated in Equation 7, a dose of radiation determined at each sensor ($D_{photodiode\_n}$) may be realized by adjusting (e.g., multiplying) each sensor signal ($Signal_{pd\_1}$, $Signal_{pd\_2}$) by a determined or determinable calibration coefficient (Coeff_calibration_i)(Coeff_calibration_n).

At 914, a particular calibration device target article 240a, 240b may be positioned in the disinfection chamber 110. The calibration device target article 240a, 240b may, for example, include any number of sensors 130a. In this way, a singular dose of radiation ($D_{solo}$) may be measured and electronically communicated from the disinfection chamber 110 to the software.

Also at 914, during the exemplary calibration process, the dose of radiation measured at each sensor 130 ($D_{photodiode\_1}$, $D_{photodiode\_2}$, $D_{photodiode\_n}$) is adjusted to be equivalent to the singular dose of radiation ($D_{solo}$) delivered to the surface of the calibration device target article 240a, 240b as indicated in Equation 8. In some cases, the singular dose of radiation ($D_{solo}$) may represent a dose of radiation delivered to cold spot 248. In other cases, the singular dose of radiation ($D_{solo}$) may represent a dose of radiation delivered to a hot spot, a uniformly radiated surface, or some other surface of the calibration device target article 240a, 240b. The singular dose of radiation ($D_{solo}$) measurements are used to link the amount of radiation impacting the surface of the calibration device target article 240a, 240b with the amount of radiation measured at each sensor 130 deployed in the subject disinfection chamber 110.

Coupling the determination of a measured dose of radiation ($D_{measured}$) as indicated in Equation 4 with the calibration factor it is recognized that a ratio ($R_{solo}$) associated with the calibration device target article 240a, 240b can be determined and used as indicated in Equation 9. Consequently, because the measured dose of radiation ($D_{measured}$) is equivalent to the singular dose of radiation ($D_{solo}$) delivered to the surface of the calibration device target article 240a, 240b, the calibration factor is determined to be the same as the ratio ($R_{solo}$) associated with the calibration device target article 240a, 240b (Equation 10).

Processing at 916 and 918 in FIG. 9D uses the calibration process and other aspects of the data flow 900 to determine the minimum dose ($D_0$.)

A target dose ($D_{target}$) of radiation is represented in Equation 3. The target dose takes into consideration a ratio (R) of the minimum dose ($D_0$) with a safety factor ($F_{safety}$) applied. As discussed in the present disclosure, the minimum dose ($D_0$) is a representative of the amount of radiation needed to provide a log reduction in viability of at least a determined amount of one or more specified microorganisms on a cold spot 248 of a target article 240. Empirical testing of inoculated test carriers, which are then irradiated in a disinfection chamber under test conditions, can be used to determine the amount of radiation necessary to achieve HLD. This test data, which is associated with a particular pathogen on a particular test carrier of known size, shape, and placement in an disinfection chamber 110, can be used with the principles of Equations 4 to 10 to determine a ratio of the particular carrier ($R_{carrier}$), which is then used as a reference ratio ($R_{ref}$) in the determination of the target dosage ($D_{target}$) as indicated in Equations 11 and 12. As previously discussed, there is a proportionality in the energy fluence ratios. The ratios between the test carriers determined during empirical testing and the sensors 130 that measure radiation within the disinfection chamber 110 are used to determine the reference ratio ($R_{ref}$).

$$R_{ref} = R_{carrier} \quad \text{(Eq. 11)}$$

$$D_{target} = D_{ref} \times \frac{R_{ref}}{R_{probe}} \times F_{safety} \quad \text{(Eq. 12)}$$

Recognizing again that the measured dosage ($D_{measured}$) at sensors 130 is an average dosage of all sensors as indicated in Equation 13, the determined carrier ratio ($R_{carrier}$) may be applied to the measured dosage ($D_{measured}$) to determine the minimum dosage as indicated in Equations 14 and 15.

$$D_{measured} = \frac{(D_{photodiode\_1} + D_{photodiode\_2} + D_{photodiode\_n})}{n} \quad \text{(Eq. 13)}$$

$$D_0 = R_{carrier} \times D_{measured} \quad \text{(Eq. 14)}$$

$$D_0 = R_{carrier} \times D_{ref} \quad \text{(Eq. 15)}$$

Processing of data flow 900 ends at 920.

Figure 10A:
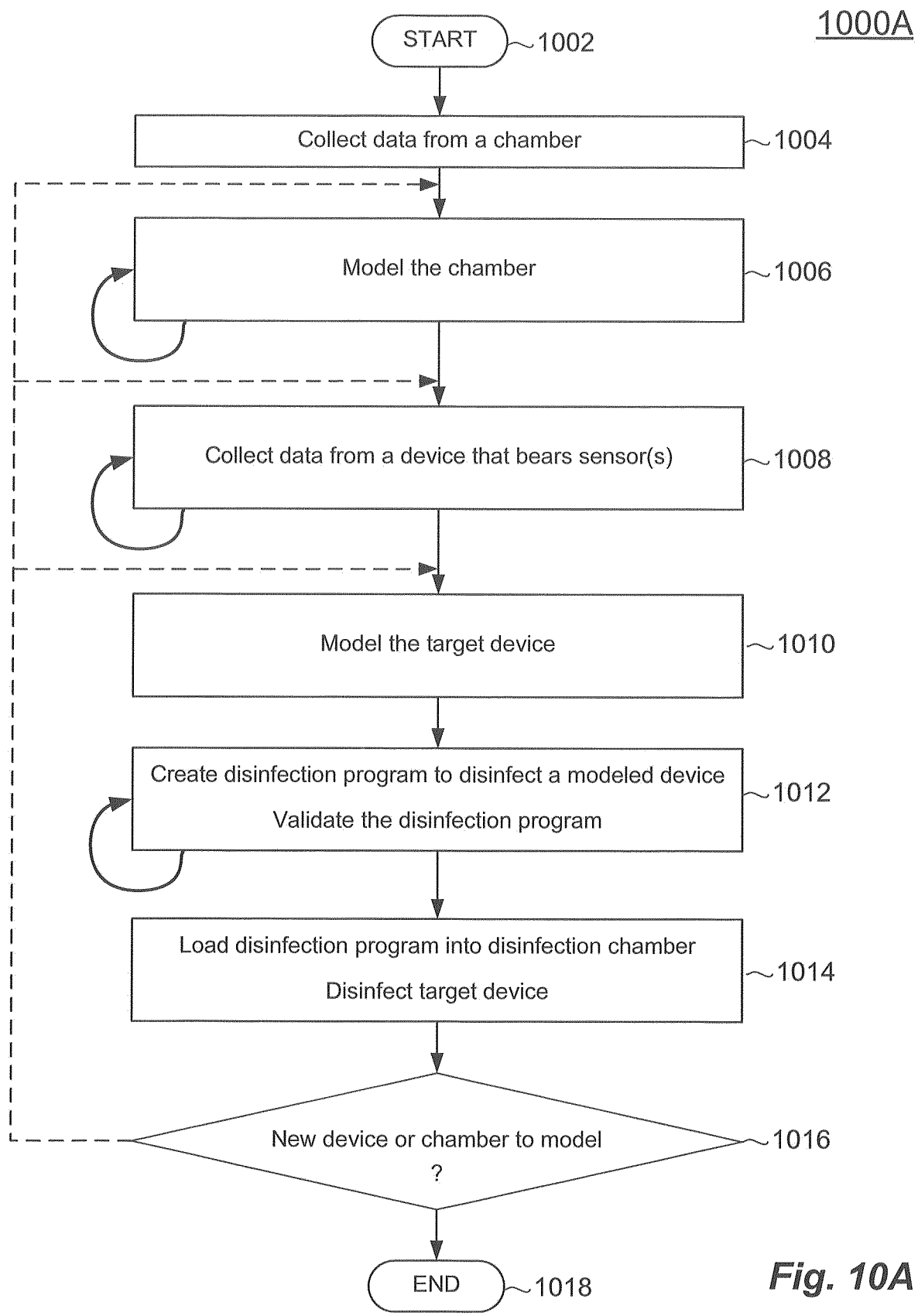
FIGS. 10A to 10C are data flow diagrams representing use of a calculated minimum dose in certain embodiments of the modeled and actual devices.
Figure 10B:
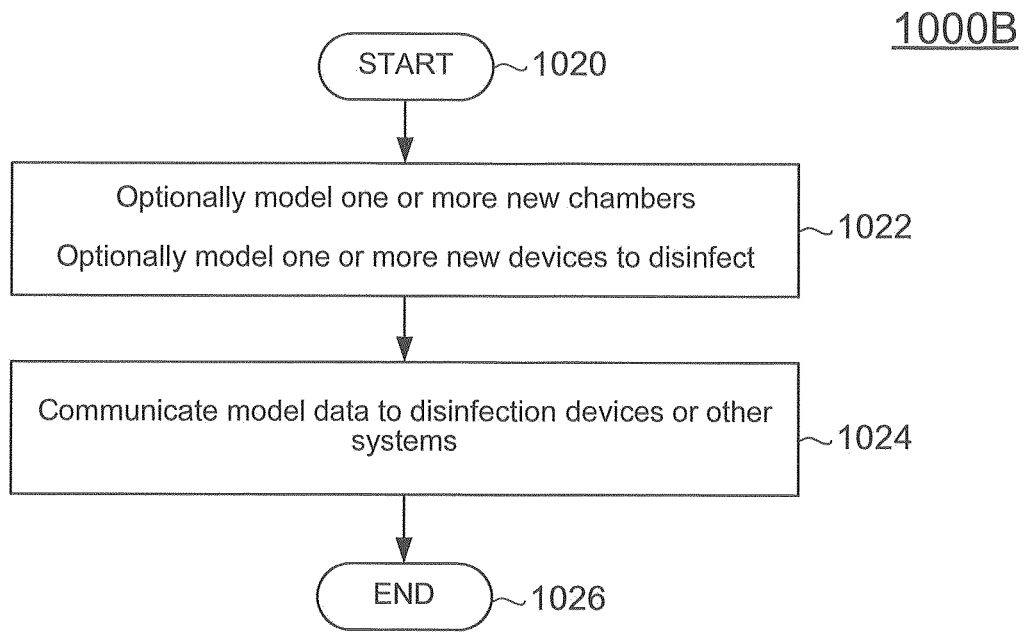
Figure 10C:
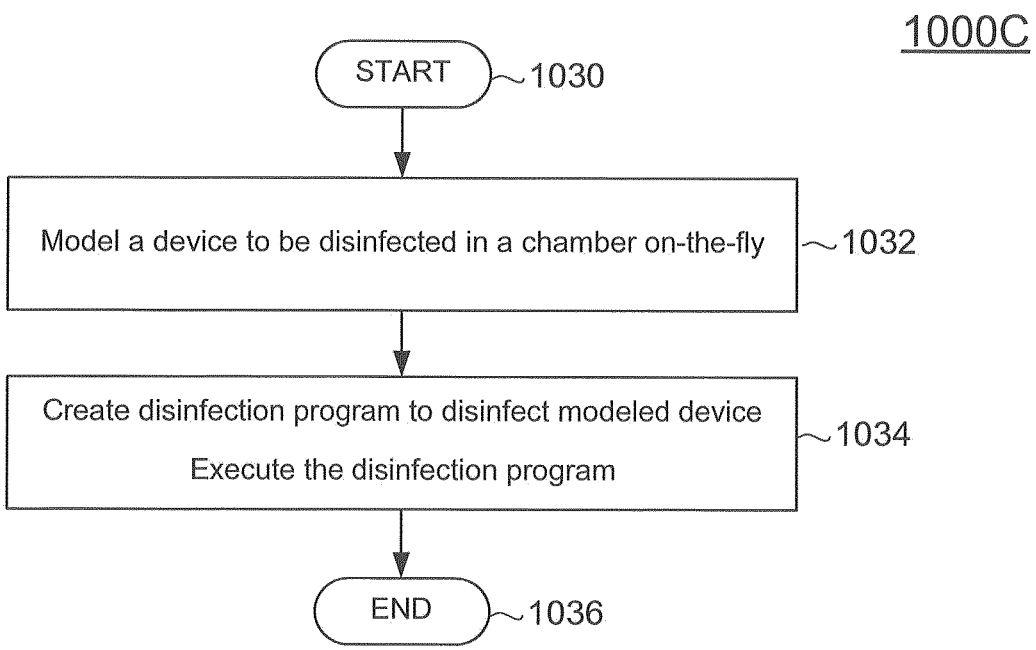

FIGS. 10A to 10C are data flow diagrams representing use of a calculated minimum dose in certain embodiments of the modeled and actual devices. FIG. 10A is a data flow 1000A embodiment that models a first disinfection chamber, models a first test article, generates a validated disinfection program and loads it into an actual first disinfection chamber. The first chamber is then operated to disinfect an actual first test article by delivering a minimum dose of generated radiation according the disinfection program. FIG. 10B is a data flow 1000B embodiment that models any number of disinfection chambers and any number of test articles. Based on the models, the data flow 1000B communicates generated disinfection programs to any number of disinfection systems 100. FIG. 100 is a data flow 100C embodiment that scans and models a device that is inside a disinfection chamber in real time. A disinfection program for disinfection of the modeled device is created in real time, and the disinfection program is executed. FIGS. 10A to 10C may be collectively referred to herein as FIG. 10.

In more detail, FIG. 10 is a set of data flow diagram embodiments that represents exemplary application of the structures and acts described in the present disclosure. One or more of data flow diagrams, alone or in combination, present a set of holistic structures and methods of disinfecting radiation dose determination convolved with specific disinfection system characteristics and attributes. The convolution results in an appropriately characterized and understood disinfection system that uses radiation (e.g., UV-C) as a disinfectant, intended to disinfect reprocessed target articles, such as ultrasound probes or other medical devices) to an acceptable level of high-level disinfection (HLD).

In FIG. 10A, processing begins at 1002 and advances to 1004.

At 1004, data is collected from a certain disinfection chamber. The disinfection chamber may be any type of such chamber. In at least some cases, the disinfection chamber is arranged to deliver UV-C radiation inside the chamber. The processing at 1004 may include "scanning" the interior volume of the disinfection chamber to capture digital data representing dimensions, angles, and other characteristics of any number of structures within the chamber. The dimensions may include data associated with radiation sources such as positioning of the radiation sources relative to teach other within the disinfection chamber, target article suspension structures, sensors, reflectivity and absorption of any number of materials within the disinfection chamber, and the like. Processing falls to 1006.

At 1006, the data collected at 1004 is used to model the particular disinfection chamber. The processing at 1006 may be carried out in accordance with structures and methods described in the present disclosure with respect to FIGS. 4 to 7. Processing at 1006 is iterative. The modeling may include a feedback system to use the results of previous modeling. The modeling may include data from other systems that implement data flow 1000A. That is, in some cases, the results of modeling a disinfection chamber may be shared across a communication network, such as the Internet, amongst a plurality of systems.

When processing at 1006 is complete, the particular disinfection chamber of interest has been modeled, and the emission of disinfecting radiation within the chamber has also been modeled. Processing proceeds to 1008.

At 1008, actual radiation data may be collected from a target article that bears one or more sensors. In these operations, an actual test target article may be placed in an actual disinfection chamber. When the disinfection chamber is operated, actual radiation data may be collected via sensors integrated with, embedded in, or otherwise associated with the test target article. This process is iterative and may include structures and methods described in the present disclosure with respect to FIGS. 5 to 7. Processing falls to 1010.

At 1010, a certain target article is modeled. The processing at 1010 may be carried out in accordance with structures and methods described in the present disclosure with respect to FIGS. 5 to 8. Processing at 1010 is iterative, and the modeling of the device may be along the lines of the chamber modeling at 1006. A feedback system may use results of previous modeling, and the results of the device modeling may be shared amongst any number of disinfection systems.

In at least some cases, the modeling of the target article will include identifying any number of regions of interest of non-uniform irradiation (i.e., hot spots, cold spots). These regions of interest of non-uniform irradiation will be processed in the creation of the disinfection program so that a minimum dose of radiation will be delivered to all surfaces of the target article.

When processing at 1010 is complete, the particular target article of interest has been modeled, and the effect of the target article on emitted disinfecting radiation within a certain disinfection chamber has also been modeled. Processing proceeds to 1012.

At 1012, a disinfection program for delivering a minimum dose of radiation to the target device is created. The minimum dose may be calculated as described throughout the present disclosure and particularly with respect to FIG. 9. The disinfection program includes instructions (e.g., software) executable by a processor of a particular disinfection system. The disinfection program may include initialization acts, data collection acts, acts that collect data from sensors, acts that control structures in the disinfection chamber such as radiation sources and timers, and other such acts. In at least some cases, the disinfection program is embodied as a software program executable on a computer device such as processor 140.

The disinfection program generated at 1012 is formed to deliver a minimum dose of radiation needed to achieve the desirable level of disinfection on the target article. The test article accounts for hot spots, cold spots, and any other like areas of non-uniform irradiance (i.e., regions of interest). When operating, the disinfection program will receive and take actions based on any number of measurements of radiation accumulated by sensors associated with the disinfection chamber. In at least some cases, the disinfection program does more than operate one or more radiation sources at a specified power level. A dose of radiation delivered to a test article is an integral of power, which may be fluctuating, delivered over time of exposure. Since a minimum dose has been calculated and is known to the disinfection program, the disinfection program knows what the total exposure (i.e., the dose) needs to be. Accordingly, the disinfection program may further operate to capture radiation measurement data from one or more sensors, and the disinfection program will then activate radiation sources (e.g., constant output, intermittent output, at various power levels, or the like) until a delivery of the minimum dose is achieved.

The disinfection program at 1012 may be validated in any known way. In some cases, disinfection programs are created and empirically tested. In other cases, disinfection program operations may be partially or fully simulated.

After processing at 1012, processing advances to 1014. Here, the disinfection program is arranged as disinfection program and provided (e.g., loaded into) to a particular disinfection chamber. The disinfection program is arranged to control any number of radiation sources in the particular disinfection chamber to emit the disinfecting radiation according to parameters determined based on the three dimensional model of the disinfection chamber and the three dimensional model of the target article to be disinfected. A target article of the type modeled, and of the type for which the disinfection program was created, is also loaded into the disinfection chamber. The target article is disinfected.

At 1016, operations of the data flow 1000A may be repeated for any number of different target articles and for any number of different disinfection chambers. In at least some cases, for example, a certain disinfection chamber may be desirably arranged to disinfect two or more types of target articles in a medical setting. By repeating particular acts of data flow 1000A, a plurality of disinfection programs can be generated, wherein each disinfection program, or a portion of a single disinfection program, may be particularly formed to disinfect each of the two or more types of target articles. In this same way, a disinfection chamber may have multiple models created to account for different assembly structures or other different configurations of the disinfection chamber. In this way, a plurality of disinfection programs can be generated, wherein each disinfection program, or a portion of a single disinfection program, may be particularly formed to account for various optional arrangements of the disinfection chamber.

Processing of the data flow 1000A ends at 1018.

In FIG. 10B, processing of the data flow 1000B begins at 1020 and advances to 1022. The processing of data flow 1000B may in some cases be integrated with the processing of data flow 1000A.

At 1022, any number of disinfection chambers, and any number of target articles may be modeled. Operations of data flow 1000B may be carried out in a disinfection system, a remote computing server, or some other computing device. In this way, any number of databases may be created or otherwise maintained. For example, certain databases may store disinfection chamber models, target article models, disinfection programs, and any parameters related to such chambers, target articles, and algorithms. Access to such databases may be granted to any number of local or remote disinfection systems. After all target articles and all disinfection chambers have been modeled, processing falls to 1024.

At 1024, the model data is communicated to any number of disinfection systems, remote computing devices, or other devices.

Processing from 1024 advances to and ends at 1026.

In FIG. 10C, processing of the data flow 1000C begins at 1030 and advances to 1032.

At 1032, a particular type of disinfection system includes a scanning system (e.g., one or more infrared transmitters and receivers, one or more cameras, or the like). Such a system allows one or both of the disinfection chamber and a target article to be scanned and modeled, "on-the-fly." Operations at 1032 may include operations of the present disclosure, such as described with respect to FIG. 10A. Processing advances from 1032 to 1034.

At 1034, the particular disinfection system creates a disinfection program to deliver a minimum dose of radiation to a modeled device. Then, with an actual target article placed in the disinfection chamber, the disinfection program is executed.

Processing from 1034 advances to and ends at 1036.

Figure 11:
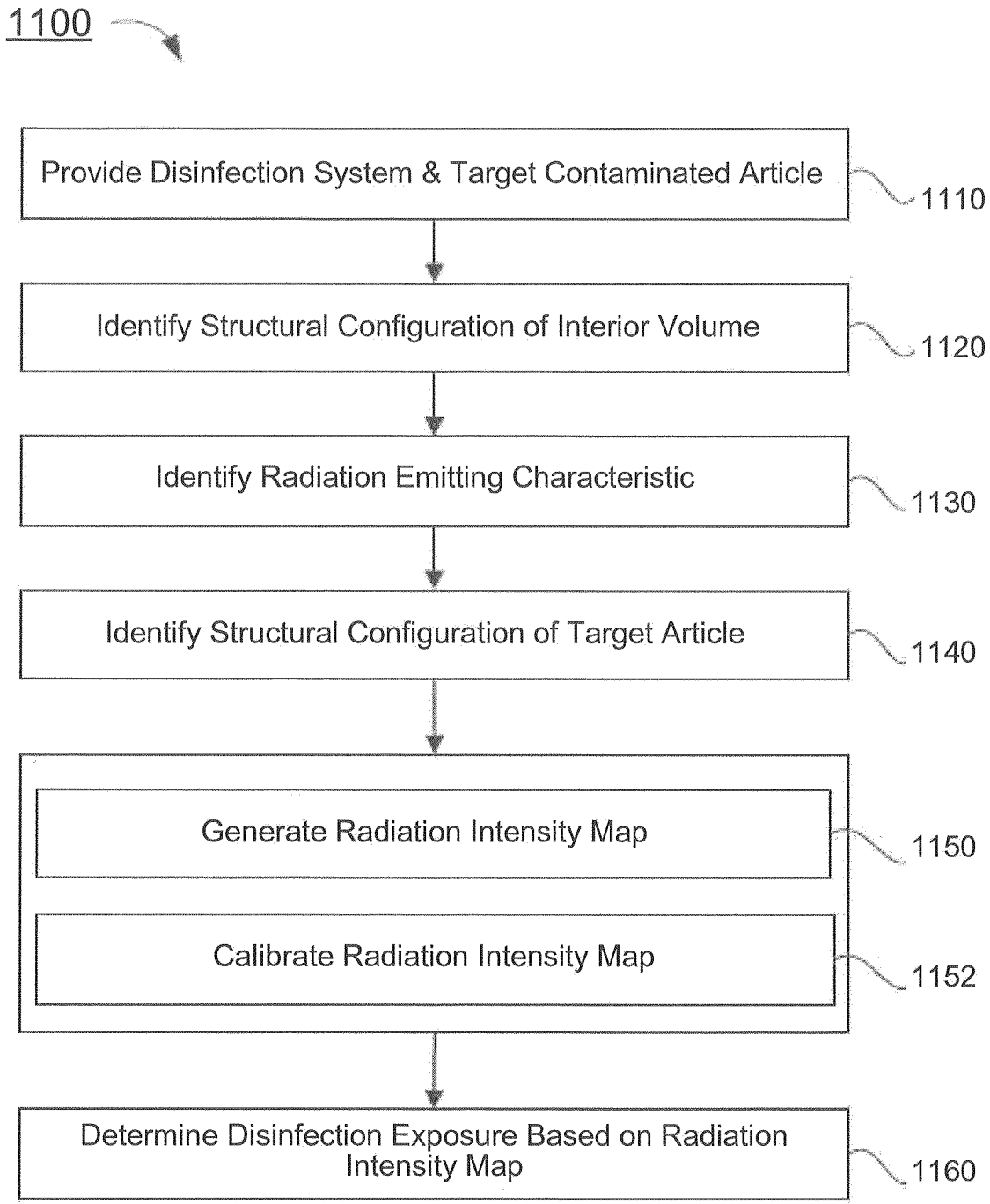
FIG. 11 illustrates a first exemplary process to determine a disinfection exposure.

FIG. 11 illustrates an exemplary process 1100 to determine a disinfection exposure. Referring to FIG. 11, in example operation 1110, a disinfection system 100 is provided as to be used for a disinfection operation of a target article 240. The disinfection system 100 includes a disinfection chamber 110 having an interior volume 112 and a radiation source 120 coupled to the interior volume 112. The radiation source 120 emits radiation light rays, e.g., UV-C light rays when in operation. Details of disinfection system 100 are described herein with respect to FIGS. 1 to 10.

Further, in example operation 1110, a target article 240 is provided. Target article 240 includes a structural configuration of the surfaces to be disinfected and includes a surface material with material characteristics including, but not limited to, heating properties and radiation reflection properties. Target article 240 may also include a disinfection standard classification, e.g., critical item, semi critical item, or noncritical item. The target article 240 may include one or more contaminants on its surface, for example, a range of microorganisms of *mycobacterium* species, *Escherichia coli*, *Staphylococcus aureus*, *Tricophyton mentagrophytes*, *Pseudomonas aeruginosa*, *Enterococcus hirae*, *Bacillus subtilis*, *Bacillus cereus*, *Clostridium sporogenes*, *Candida albicans*, Orthopoxvirus, Enterovirus, Adenovirus type 5, and human papilloma virus.

In example operation 1120, interior volume patterning unit 184 identifies a structural configuration of the interior volume 112. A structural configuration may include any structure related features of interior volume 112 that affects radiation intensity on a disinfection region within interior volume 112. The structural configuration may include a size and shape of interior volume 112, a position of attachment mechanism 242 that holds a target article 240 within interior volume 112, a number of radiation sources 120 attached to interior volume 112, positions of radiation sources 120, a number and positions of reflectors within interior volume 112, etc. Interior volume patterning unit 184 may identify the structural configuration of interior volume 112 through user inputs, e.g., via disinfection requirement inputs 160 or retrieve such information from database 150.

In example operation 1130, radiation source patterning unit 186 identifies a radiation emitting characteristic of radiation sources 120 of disinfection system 100. The radiation emitting characteristic of radiation source 120 may include or relate to an age of the radiation source 120 and may be time dependent, i.e., the emitted radiation light ray may change with a time lapse after the radiation source 120 is turned on for operation. The radiation emitting characteristic may include a radiation intensity of UV-C light rays emitted by radiation source 120 and may include a range/angle of the trajectory that radiation light rays travel.

The radiation emitting characteristic of a radiation source 120 may be at least one received from database 150 or detected by sensors 130. For example, the actual operation of a radiation source 120 may be monitored by sensors 130 and the monitored data may be fed back to controller 140 to dynamically update the database 150 with respect to the radiation emitting characteristic of radiation source 120.

In example operation 1140, target article patterning unit 188 identifies a surface structural configuration of the identified target article 240. As will be appreciated, the surface structural configuration may affect the radiation intensity delivered on the surface of the target article 240. The surface structural configuration may include a surface shape of the target article 240 including one or more of a hole, an indentation, a protuberance, or any other physical features of the target article 240. The surface structural configuration may also include a position, alignment, orientation, or the like of the target article 240 within the interior volume 112 under the disinfection operation. The surface structural configuration may also include parameters representing a surface material of the target article 240.

In example operation 1150, radiation intensity map generation unit 190 generates a radiation intensity map of interior volume 112 based on one or more of the UV-C radiation emitting characteristic of radiation sources 120, the structural configuration of the interior volume 112, and the surface structural configuration of the target article 240. The radiation intensity map includes a radiation intensity value for each disinfection region within interior volume 112, which values are relevant to the disinfection operation of the target article 240. That is, the radiation intensity map may or may not include values that actually or by calculation represent every spot and in every orientation within interior volume 112 to an acceptable level of precision.

In some embodiments, the radiation intensity map may be generated under the assumption that target article 240 positioned within interior volume 112 does not change the radiation intensity on a disinfection region. As such the radiation intensity may be generated for an empty interior volume 112.

In some other embodiment, it may be assumed that the surface structural configuration and/or surface optical properties of a target article 240 may substantially change the radiation intensity on a disinfection region within interior volume 112. For example, the surface shape of target article 240 may reflect radiant light rays that affect the radiation intensity. The surface material of the target article 240 may also affect the reflection and absorption of radiation light rays. Further, some unique, non-linear, or non-simple shapes of a target article 240 may affect the amount of radiation light rays that reach a surface portion of the target article 240. For example, it may be difficult for radiation light rays to reach the bottom area of a long tubular surface portion of a target article 240.

As the radiation emitting characteristic of a radiation source 120 may be time dependent, multiple radiation intensity maps may also be generated for multiple time points in an operation cycle of radiation source 120. Radiation intensity maps may also be generated for different operation states, e.g., output power level, of radiation source 120.

Figure 12:
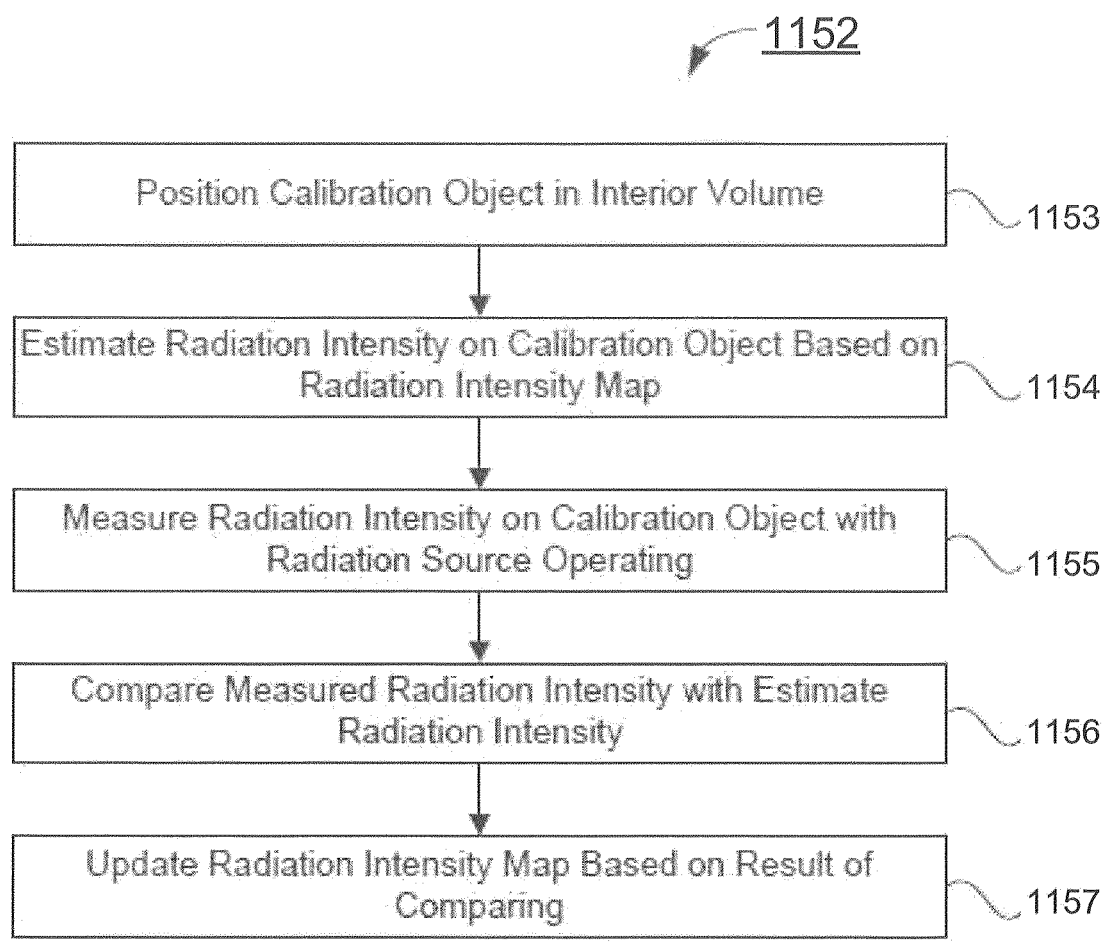
FIG. 12 illustrates exemplary details of a first sub-operation to calibrate a radiation intensity map.

Example operation 1150 may include a sub-operation 1152, where calibration unit 192 "calibrates" values represented in the generated radiation intensity map. In an embodiment, the calibration is conducted by measuring actual radiation intensity on a calibration object positioned within interior volume 112 and comparing measured radiation intensity values with generated intensity values represented in the radiation intensity map. FIG. 12 illustrates example details of a sub-operation 1152 to calibrate a radiation intensity map.

Referring to FIG. 12, in example operation 1153, a calibration object is positioned within interior volume 112. The calibration object may be comparable to the target article 240 at least in some portions. For example, the calibration object may include the same or a similar surface structural configuration as the target article 240, including the surface shape and the surface material. The calibration object may be positioned similarly within interior volume 112 as the target article 240. In an example, an actual disinfection operation of a target article 240 may serve the calibration purposes. For example, the monitored radiation intensity data for an actual disinfection operation of the target article is used to calibrate the radiation intensity map used for the disinfection operation of other similar target articles.

Sensors may be directly attached to the calibration object on selected portions. For example, if the target article 240 and the calibration object include special surface shapes that potentially affect the estimation of radiation intensity delivered on the surface shapes, sensors may be attached to such surface shapes to measure the actual radiation intensity delivered thereon.

In example operation 1154, the radiation intensity of any number of disinfection regions that overlap with the measurement regions of the sensors associated with the calibration object, including sensors attached to the calibration object and attached to the interior volume 112, may be estimated or otherwise calculated based on radiation values represented in the radiation intensity map. In the case that the calibration object is identical or substantially similar to the target article 240, the estimated radiation intensity values may be directly retrieved from the radiation intensity map. In the case that the calibration object is comparable but not identical to the target article 240, the estimated radiation intensity value may be recalculated based on the radiation intensity map because the surface structural of the calibration object may affect radiation intensity delivered thereon differently than the target article 240. In at least some of these cases, the recalculation may be based on information associated with any one or more of a model of the disinfection chamber, a model of the target article, a model of data from a light ray tracing program, as discussed in the present disclosure.

In example operation 1155, with the radiation source 120 operating, actual radiation intensity values are measured by the sensors attached to the calibration object and sensor 130 attached to interior volume 112. In an example, multiple radiation intensity values are measured for a same disinfection region and/or a same portion of the calibration object as time lapses. In this way, time dependent variation of the radiation intensity values may also be determined and used in ray tracing program models, development of disinfection programs, and the like to predict or otherwise characterize output radiation of radiation sources 120.

In example operation 1156, the measured radiation intensity values and the estimated radiation intensity values are algorithmically combined, such as by a comparison.

In example operation 1157, radiation intensity values represented in the radiation intensity map may be updated based on the result of operation 1156. The update may be done at least one of locally on the specific disinfection regions, e.g., "touchup" updates, or globally with the algorithm that generates the radiation intensity map. More specifically, results of the calibration procedures described in 1152 may be used to adjust individual (i.e., local) radiation intensity values represented in the radiation intensity map. Such adjustments may be, for example, to account for hot spots that are measured hotter or colder than expected, cold spots that are measured hotter or colder than expected, or hot or cold spots that were not expected at all. In addition, or in the alternative, the results of a calibration procedure may determine that all (i.e., global) radiation intensity values represented in the radiation intensity map are empirically determined in calibration testing to be either too low or too high.

Referring back to FIG. 11, in example operation 1160, disinfection exposure determination unit 142 determines a disinfection exposure on the target article 240 based on the updated radiation intensity map. Besides the updated radiation intensity map, a temperature reaction of the target article to the radiation may also be considered in the disinfection exposure. In an example different disinfection exposure may be determined for different portions of the target article as the radiation intensity delivered on the different portions are different and the heating properties of the different portions are different. The disinfection exposure may include varied operation states of radiation sources 120 among different portions of target article 240 and/or along different time points in the disinfection cycle.

In the foregoing disclosure, embodiments of devices, systems, and methods are described that illustrate and discuss high-level disinfection (HLD) cycles performed based on one or more of the timed delivery of radiation into a chamber, the determined dose of radiation delivered into a chamber, and the combination of time duration and determined dose of radiation delivery into a chamber. In these cases, a minimum dose of radiation is determined to be delivered to a device in the chamber, and in particular, the minimum dose of radiation is determined to be delivered to at least one region of interest (e.g., a determined cold spot) of the device. This determination may be made, at least in part, using one or more sensors arranged to control the radiation delivery means in a way that confirms, with acceptable certainty, that the correct minimum dose was delivered during the cycle.

The one or more sensors may include clock (e.g., timing) circuits, radiation measuring (e.g., photodiode) circuits, temperature circuits, foreign object detection circuits, device identification circuits, and other such circuits. In some cases, one or more sensors are radiation measuring circuits (e.g., radiation sensor circuits) arranged to capture instantaneous radiation measurements, radiation measurements accumulated over time, or some other data that represents instantaneous or accumulated radiation. Hence, using the sensors and a cooperating control circuit (e.g., a processor), the determined minimum dose can be delivered. In one case, for example, one or more sensors are configured to turn on and turn off the radiation source based on a length of time that defines a determined radiation delivery cycle. In another case, one or more sensors are configured to turn on and turn off the radiation source based on an accumulation of radiation until delivery of the minimum dose is determined. In still another case, one or more sensors are configured to identify the device placed in the chamber, and the identification information is used, at least in part, to control the radiation source over the radiation delivery cycle. In yet one more case, one or more sensors are configured to determine whether the device is correctly placed in the chamber in a specific orientation, position, and the like, and information from such sensors is used, at least in part, to control the radiation delivery cycle.

Various methods, devices, and systems are now set forth to provide details of certain exemplary and non-limiting embodiments. Various features of the embodiments are optional, and aspects of one embodiment may be suitably combined with other embodiments.

Example A-1 is a method, comprising: providing a disinfection chamber having an interior volume and at least one radiation source coupled to the interior volume, the at least one radiation source arranged to emit disinfecting radiation into the interior volume when in operation; determining a cold spot of a target article to be disinfected; and providing a disinfection program to the disinfection chamber, the disinfection program arranged to control the at least one radiation source to emit the disinfecting radiation according to the determined cold spot. Example A-2 may include the subject matter of Example A-1, and alternatively or additionally any other example herein, and further comprise: identifying a plurality of regions of the target article to be disinfected; in the plurality of regions, determining a quantity of disinfecting radiation that will be received at each of the plurality of regions over a selected time period; comparing the quantities of disinfecting radiation to determine which region will receive a least amount of disinfecting radiation; and identifying the region that will receive the least amount of disinfecting radiation as the determined cold spot of the target article to be disinfected. Example A-3 may include the subject matter of any of Examples A-1 and A-2, and alternatively or additionally any other example herein, and further comprise: identifying a first region of the target article that will receive less disinfecting radiation than a second region of the target article. Example A-4 may include the subject matter of Example A-3, and alternatively or additionally any other example herein, wherein the receipt of less disinfecting radiation at the first region is caused, at least in part, by an interaction between geometry of the first region and geometry of the disinfection chamber. Example A-5 may include the subject matter of Example A-3, and alternatively or additionally any other example herein, wherein the receipt of less disinfecting radiation at the first region is caused, at least in part, by an interaction between geometry of the first region and geometry of the second region. Example A-6 may include the subject matter of Example A-3, and alternatively or additionally any other example herein, wherein the receipt of less disinfecting radiation at the first region is caused, at least in part, by a position of the target article in the disinfection chamber. Example A-7 may include the subject matter of Example A-3, and alternatively or additionally any other example herein, wherein the receipt of less disinfecting radiation at the first region is caused, at least in part, by a determined value representing an amount of absorption associated with at least one of the target article and the disinfection chamber. Example A-8 may include the subject matter of Example A-3, and alternatively or additionally any other example herein, wherein the receipt of less disinfecting radiation at the first region is caused, at least in part, by a determined value representing an amount of reflectivity associated with at least one of the target article and the disinfection chamber. Example A-9 may include the subject matter of Example A-3, and alternatively or additionally any other example herein, wherein the receipt of less disinfecting radiation at the first region is caused, at least in part, by a determined value representing an amount of diffusion associated with at least one of the target article and the disinfection chamber. Example A-10 may include the subject matter of Example A-3, and alternatively or additionally any other example herein, wherein the receipt of less disinfecting radiation at the first region is caused, at least in part, by a position of each of the at least one radiation source in the disinfection chamber. Example A-11 may include the subject matter of Example A-4, and alternatively or additionally any other example herein, and further comprise: modeling the geometry of the first region; modeling the geometry of the disinfection chamber; and modeling disinfecting radiation in the disinfection chamber to determine the first and second regions. Example A-12 may include the subject matter of Example A-5, and alternatively or additionally any other example herein, and further comprise: modeling the geometry of the first region; modeling the geometry of the second region; and modeling an obstruction of the disinfecting radiation to the first region. Example A-13 may include the subject matter of any of Examples A-1 to A-12, and alternatively or additionally any other example herein, and further comprise: providing an indication that the target article is improperly placed in the disinfection chamber. Example A-14 may include the subject matter of any of Examples A-1 to A-12, and alternatively or additionally any other example herein, wherein control of the at least one radiation source to emit the disinfecting radiation according to the determined cold spot includes: emitting the disinfecting radiation for a determined period of time. Example A-15 may include the subject matter of any of Examples A-1 to A-12, and alternatively or additionally any other example herein, wherein control of the at least one radiation source to emit the disinfecting radiation according to the determined cold spot includes: determining an amount of disinfecting radiation received, instantaneously or over time, at a sensor, wherein the amount of disinfecting radiation received, instantaneously or over time, at the sensor is indicative of how much disinfecting radiation is received at the determined cold spot; and ending emission of disinfecting radiation based on the determined amount of disinfecting radiation received, instantaneously or over time, at the sensor. Example A-16 may include the subject matter of Example A-15, and alternatively or additionally any other example herein, wherein determining the amount of disinfecting radiation received at the sensor includes collecting data from the sensor over time.

Example B-1 is a system, comprising: a disinfection chamber having an interior volume; at least one radiation source arranged, when in operation, to emit disinfecting radiation into the interior volume of the disinfection chamber; a target article positioning device; a memory, the memory having stored thereon a computer-generated model of a determined type of medical device, said computer-generated model including data that represents at least one physical property of the determined type of medical device, said computer-generated model including data that represents at least one optical property of the determined type of medical device, and said computer-generated model including data that represents a region of interest on the surface of the determined type of medical device, wherein said region of interest is a first region that is expected to receive a disinfecting radiation dose that is different from a second region; and a control system arranged to direct the operation of the at least one radiation source, wherein directing the operation includes causing delivery of a determined minimum dose of disinfecting radiation to the region of interest of a medical device of the determined type when said medical device of the determined type is coupled to the target article positioning device. Example B-2 may include the subject matter of Example B-1, and alternatively or additionally any other example herein, wherein the memory has stored thereon a plurality of computer-generated models of a plurality of determined types of medical devices. Example B-3 may include the subject matter of any of Examples B-1 and B-2, and alternatively or additionally any other example herein, and further comprise: at least one radiation sensor circuit, wherein delivery of the determined minimum dose of disinfecting radiation to the region of interest is based on data provided by the at least one radiation sensor circuit. Example B-4 may include the subject matter of Example B-3, and alternatively or additionally any other example herein, wherein the at least one radiation sensor circuit includes a photodiode. Example B-5 may include the subject matter of any of Examples B-1 to B-4, and alternatively or additionally any other example herein, wherein the control system is further arranged to provide an indication of an improperly positioned medical device. Example B-6 may include the subject matter of any of Examples B-1 to B-5, and alternatively or additionally any other example herein, wherein the region of interest is a cold spot and the at least one physical property represents a topological characteristic of the determined type of medical device that obstructs the disinfecting radiation from reaching region of interest. Example B-7 may include the subject matter of any of Examples B-1 to B-5, and alternatively or additionally any other example herein, wherein the control system is further arranged to direct the at least one radiation source to emit disinfecting radiation over a determined period of time, the determined period of time derived from a ratio of radiation delivered to the region of interest of the medical device of the determined type and radiation delivered to at least one of another region on the surface of the medical device of the determined type, a radiation sensor, and another region in the interior volume of the disinfection chamber.

Example C-1 is a non-transitory computer readable storage medium containing executable instructions which, when executed by a processor, configure the processor to operate a disinfection system according to a method, the method comprising acts to: provide a disinfection chamber having an interior volume and a radiation source coupled to the interior volume, the radiation source arranged to emit disinfecting radiation into the interior volume when in operation; and provide a disinfection program to the disinfection chamber, the disinfection program arranged to control the radiation source to emit the disinfecting radiation according to parameters determined based on at least one of a three dimensional model of the disinfection chamber and a three dimensional model of a target article to be disinfected. Example C-2 may include the subject matter of Example C-1, and alternatively or additionally any other example herein, and the method may further comprise acts to: form the three dimensional model of the disinfection chamber by: operating at least one radiation source in a data collection disinfection chamber; collecting radiation data with at least one radiation sensor; and generating, from the collected radiation data, a radiation intensity map representing a plurality of radiation intensity values in a plurality of regions of the data collection disinfection chamber. Example C-3 may include the subject matter of Example C-1, and alternatively or additionally any other example herein, and the method may further comprise acts to: form the three dimensional model of the disinfection chamber by: providing an initial disinfection chamber model having a virtual interior volume; providing a mathematical mapping of the virtual interior volume, by arranging a plurality of virtual polygons, for example, to create the mathematical mapping; generating, with a ray tracing program, simulated radiation ray information based on the mathematical mapping of the virtual interior volume; and generating, from the simulated radiation ray information, a radiation intensity map representing a plurality of radiation intensity values in a plurality of regions of the disinfection chamber. Example C-4 may include the subject matter of any of Examples C-1 to C-3, and alternatively or additionally any other example herein, and the method may further comprise acts to: form the three dimensional model of the target article to be disinfected by: providing an initial target article model having a virtual surface; providing a mathematical mapping of the virtual surface, by arranging a plurality of virtual polygons, for example, to create the mathematical mapping; and identifying at least one spot on the virtual surface of non-uniform irradiation. Example C-5 may include the subject matter of any of Examples C-1 to C-3, and alternatively or additionally any other example herein, and the method may further comprise acts to: form the disinfection program by: calculating a minimum dose of radiation to apply to the target article to be disinfected, wherein calculating the minimum dose includes information associated with at least one identified cold spot; based on the minimum dose, applying data from a radiation intensity map to the three dimensional model of the target article to be disinfected; and creating parameters to control the radiation source to deliver the minimum dose of radiation.

Example D-1 is a method, comprising: providing a disinfection chamber having an interior volume and a radiation source coupled to the interior volume, the radiation source arranged to emit disinfecting radiation into the interior volume when in operation, and providing a disinfection program to the disinfection chamber, the disinfection program arranged to control the radiation source to emit the disinfecting radiation according to parameters determined based on at least one of a three dimensional model of the disinfection chamber and a three dimensional model of a target article to be disinfected. Example D-2 may include the subject matter of Example D-1, and alternatively or additionally any other example herein, and further comprise: forming the three dimensional model of the disinfection chamber by: operating at least one radiation source in a data collection disinfection chamber; collecting radiation data with at least one radiation sensor; and generating, from the collected radiation data, a radiation intensity map representing a plurality of radiation intensity values in a plurality of regions of the data collection disinfection chamber. Example D-3 may include the subject matter of any of Examples D-1 and D-2, and alternatively or additionally any other example herein, and further comprise: forming the three dimensional model of the disinfection chamber by: providing an initial disinfection chamber model having a virtual interior volume; providing a mathematical mapping of the virtual interior volume, by arranging a plurality of virtual polygons, for example, to create the mathematical mapping; generating, with a ray tracing program, simulated radiation ray information based on the mathematical mapping of the virtual interior volume; and generating, from the simulated radiation ray information, a radiation intensity map representing a plurality of radiation intensity values in a plurality of regions of the disinfection chamber. Example D-4 may include the subject matter of any of Examples D-1 to D-3, and alternatively or additionally any other example herein, and further comprise: forming the three dimensional model of the target article to be disinfected by: providing an initial target article model having a virtual surface; providing a mathematical mapping of the virtual surface, by arranging a plurality of virtual polygons, for example, to create the mathematical mapping; and identifying at least one spot on the virtual surface of non-uniform irradiation. Example D-5 may include the subject matter of any of Examples D-1 to D-4, and alternatively or additionally any other example herein, and further comprise: forming the disinfection program by: calculating a minimum dose of disinfecting radiation to apply to the target article to be disinfected, wherein calculating the minimum dose includes information associated with at least one identified cold spot; based on the minimum dose, applying data from a radiation intensity map to the three dimensional model of the target article to be disinfected; and creating parameters to control the radiation source to deliver the minimum dose of disinfecting radiation. Example D-6 may include the subject matter of any of Examples D-1 to D-5, and alternatively or additionally any other example herein, wherein the disinfection program is further based on a radiation intensity map, the radiation intensity map based on at least one radiation emitting characteristic of the radiation source. Example D-7 may include the subject matter of any of Examples D-1 to D-6, and alternatively or additionally any other example herein, and further comprise: positioning a calibration object in the interior volume; operating the radiation source with the calibration object in the interior volume; measuring a radiation intensity value on a portion of the calibration object with the radiation source operating; and updating a radiation intensity map based on the measured radiation intensity value. Example D-8 may include the subject matter of any of Examples D-1 to D-7, and alternatively or additionally any other example herein, wherein the disinfection program is further based on a radiation intensity map, the radiation intensity map having multiple radiation intensity values for a same spot in the interior volume, each of the multiple radiation intensity values associated with a time factor of the operating the radiation source. Example D-9 may include the subject matter of Example D-8, and alternatively or additionally any other example herein, wherein the time factor includes an age of the radiation source. Example D-10 may include the subject matter of any of Examples D-9 to D-10, and alternatively or additionally any other example herein, wherein the time factor includes a time lapse of the operating the radiation source.

Example E-1 is a method. The method may be directed toward modeling a determined type of medical device in advance of disinfecting medical devices of the determined type. The method of example E-1 comprises: selecting a determined type of medical device, said determined type of medical device having a surface; creating a computer-generated model of the determined type of medical device, said computer-generated model formed as a mathematical mapping of the surface of the determined type of medical device, said computer-generated model including data that represents at least one physical property of the determined type of medical device and at least one optical property of the determined type of medical device; and identifying a region of interest on the surface of the determined type of medical device that is expected to receive a disinfecting radiation dose of interest that is different from an overall average disinfecting radiation dose. Example E-2 may include the subject matter of Example E-1, and alternatively or additionally any other example herein, wherein the at least one physical property represents a topological characteristic of the target article. Example E-3 may include the subject matter of Examples E-1 and E-2, and alternatively or additionally any other example herein, wherein the at least one physical property includes a value representing a dimple, a contour, a crack, a crevice, an aperture, a protuberance, a registration feature, a target article positioning structure, or a connector. Example E-4 may include the subject matter of Examples E-1 to E-3, and alternatively or additionally any other example herein, wherein the at least one optical property includes a value representing reflectivity, absorption, or diffusion. Example E-5 may include the subject matter of Examples E-1 to E-4, and alternatively or additionally any other example herein, wherein the at least one optical property is based on a first portion of the surface being obstructed from directly receiving the disinfecting radiation dose by a second portion of the surface. Example E-6 may include the subject matter of Examples E-1 to E-5, and alternatively or additionally any other example herein, wherein identifying the region of interest on the surface of the determined type of medical device, comprises: providing a test article, the test article being of the determined type of medical device; applying a radiation-sensitive material to a surface of the test article; irradiating the test article; and calculating, based on changes to the radiation-sensitive material after the irradiating, a value representing a dose of the disinfecting radiation received at the surface of the test article. Example E-7 may include the subject matter of Examples E-1 to E-6, and alternatively or additionally any other example herein, wherein identifying the region of interest on the surface of the determined type of medical device, comprises: providing a test article, the test article being of the determined type of medical device; integrating at least one sensor with the test article, the at least one sensor arranged to receive data representing disinfecting radiation delivered to a surface of the test article; irradiating the test article; and determining, from the data received by the at least one sensor, where a first dose of the disinfecting radiation received at a first region of the test article is different from a second dose of the disinfecting radiation received at a second region of the test article. Example E-8 may include the subject matter of Examples E-1 to E-7, and alternatively or additionally any other example herein, wherein identifying the region of interest on the surface of the determined type of medical device, comprises: providing a test article, the test article being of the determined type of medical device; integrating at least one sensor with the test article, the at least one sensor arranged to receive data representing disinfecting radiation delivered to a surface of the test article; irradiating the test article; and calculating, from the data received by the at least one sensor, a value representing a dose of the disinfecting radiation received at the surface of the test article. Example E-9 may include the subject matter of Examples E-1 to E-8, and alternatively or additionally any other example herein, wherein the at least one sensor includes a photodiode. Example E-10 may include the subject matter of Examples E-1 to E-9, and alternatively or additionally any other example herein, wherein integrating the at least one sensor includes coupling the surface of the test article to the at least one sensor via a photonic conductor. Example E-11 may include the subject matter of Examples E-1 to E-10, and alternatively or additionally any other example herein, and further comprise: modifying the computer-generated model based on the identified region of interest. Example E-12 may include the subject matter of Examples E-1 to E-11, and alternatively or additionally any other example herein, and further comprise: modifying the computer-generated model based on a determined position of the selected target article within the disinfecting chamber. Example E-13 may include the subject matter of Examples E-1 to E-12, and alternatively or additionally any other example herein, wherein the computer-generated model is derived from an earlier formed computer-generated model, the earlier formed computer-generated model based on a second determined type of medical device. Example E-14 may include the subject matter of Examples E-1 to E-13, and alternatively or additionally any other example herein, and further comprise: generating a disinfection protocol for a selected medical device of the determined type, the selected medical device having the identified region of interest on its surface, wherein the disinfection protocol directs at least one radiation source associated with a selected disinfection chamber to irradiate the selected medical device when the selected medical device is placed within the selected disinfection chamber. Example E-15 may include the subject matter of Example E-14, and alternatively or additionally any other example herein, wherein generating the disinfection protocol includes: directing the at least one radiation source to irradiate the selected medical device until a determined dose of disinfecting radiation has been delivered to the identified region of interest of the selected medical device. Example E-16 may include the subject matter of Example E-14, and alternatively or additionally any other example herein, wherein generating the disinfection protocol includes: directing the at least one radiation source to irradiate the selected medical device until a determined dose of disinfecting radiation has been delivered to at least one sensor arranged in the disinfection chamber. Example E-17 may include the subject matter of Example E-14, and alternatively or additionally any other example herein, wherein generating the disinfection protocol includes: directing the at least one radiation source to irradiate the selected medical device over a determined period of time, the determined period of time derived from a ratio of radiation delivered to the identified region of interest of the selected medical device and another region on the surface of the selected medical device. Example E-18 may include the subject matter of Example E-14, and alternatively or additionally any other example herein, wherein generating the disinfection protocol includes: modifying the disinfection protocol based on at least a determined position of the selected medical device in the disinfection chamber. Example E-19 may include the subject matter of Example E-14, and alternatively or additionally any other example herein, wherein generating the disinfection protocol includes: modifying the disinfection protocol based on a detection of a foreign object in the disinfection chamber. Example E-20 may include the subject matter of Example E-14, and alternatively or additionally any other example herein, wherein the disinfection protocol further directs an operator of the disinfection chamber to reposition the selected medical device within the disinfecting chamber based on an indication of improper placement of the selected medical device within the disinfecting chamber. Example E-21 may include the subject matter of Example E-14, and alternatively or additionally any other example herein, wherein the region of interest is identified based on at least one topological characteristic of the selected medical device. Example E-22 may include the subject matter of any of Examples E-1 to E-21, and alternatively or additionally any other example herein, wherein the identified region of interest is a cold spot on the surface of the selected medical device. Example E-23 may include the subject matter of any of Examples E-1 to E-22, and alternatively or additionally any other example herein, wherein the identified region of interest is a hot spot on the surface of the selected medical device. Example E-24 may include the subject matter of any of Examples E-1 to E-23, and alternatively or additionally any other example herein, wherein the computer-generated model is a three-dimensional model. Example E-25 may include the subject matter of any of Examples E-1 to E-24, and alternatively or additionally any other example herein, wherein the disinfecting radiation dose is a dose of ultraviolet (UV) radiation.

Example F-1 is a method, comprising: providing a disinfection chamber having an interior volume and a radiation source coupled to the interior volume, the radiation source emitting ultraviolet-C (UV-C) radiation into the interior volume when in operation; identifying a UV-C radiation emitting characteristic of the radiation source; identifying a structural configuration of the interior volume; estimating a UV-C radiation intensity map within the interior volume based on the UV-C radiation emitting characteristic and the structural configuration of the interior volume; and determining a disinfection dosage of an infected article based on the UV-C radiation intensity map. Example F-2 may include the subject matter of Example F-1, and alternatively or additionally any other example herein, wherein the determining the disinfection dosage includes: positioning a calibration object in the interior volume; estimating a first UV-C radiation intensity value on a portion of the calibration object based on the UV-C radiation intensity map; operating the radiation source with the calibration object in the interior volume; measuring a second UV-C radiation intensity value on the portion of the calibration object with the radiation source operating; comparing the first UV-C radiation intensity value and the second UV-C intensity value; updating the UV-C radiation intensity map based on a result of the comparing; updating the UV-C radiation intensity map based on a result of the comparing; and determining the disinfection dosage based on the updated UV-C radiation map. Example F-3 may include the subject matter of Example F-2, and alternatively or additionally any other example herein, wherein the portion of the calibration object is comparable to a portion of the infected article with respect to receiving UV-C radiation. Example F-4 may include the subject matter of Example F-3, and alternatively or additionally any other example herein, wherein the portion of the calibration object includes a comparable surface structural configuration as the portion of the infected article. Example F-5 may include the subject matter of Example F-3, and alternatively or additionally any other example herein, wherein the portion of the calibration object includes a comparable surface material as the portion of the infected article. Example F-6 may include the subject matter of Example F-2, and alternatively or additionally any other example herein, wherein the measuring the second UV-C radiation intensity value includes measuring multiple second UV-C radiation intensity values one a same spot of the portion of the calibration object as time lapses in operating the radiation source with the calibration object in the interior volume. Example F-7 may include the subject matter of any of Examples F-1 to F-6, and alternatively or additionally any other example herein, wherein the UV-C radiation intensity map includes multiple UV-C radiation intensity values for a same spot in the interior volume, each of the multiple UV-C radiation intensity value associated with a time factor of the operating the radiation source. Example F-8 may include the subject matter of Example F-7, and alternatively or additionally any other example herein, wherein the time factor includes an age of the radiation source. Example F-9 may include the subject matter of Example F-7, and alternatively or additionally any other example herein, wherein the time factor includes a time lapse of the operating the radiation source. Example F-10 may include the subject matter of any of Examples F-1 to F-9, and alternatively or additionally any other example herein, wherein the estimating the UV-C radiation intensity map within the interior volume includes at least one of: estimating a first UV-C radiation intensity map for the interior volume at an empty state; estimating a second UV-C radiation intensity map for the interior volume with an object positioned therein. Example F-11 may include the subject matter of Example F-10, and alternatively or additionally any other example herein, wherein the object is at least one of: the infected article; or a calibration object. Example F-12 may include the subject matter of any of Examples F-1 to F-11, and alternatively or additionally any other example herein, wherein the determining the disinfection dosage based on the UV-C radiation intensity map includes determining a dosage map including a first dosage for a first portion of the infected article and a second different dosage for a second portion of the infected article. Example F-13 may include the subject matter of any of Examples F-1 to F-12, and alternatively or additionally any other example herein, wherein the identifying the UV-C radiation emitting characteristic of the radiation source is based on received UV-C radiation intensity data of the radiation source detected by a sensor positioned in the interior volume. Example F-14 may include the subject matter of any of Examples F-1 to F-13, and alternatively or additionally any other example herein, wherein the estimating the UV-C radiation intensity map within the interior volume includes estimating multiple UV-C radiation intensity maps based on multiple operation states of the radiation source. Example F-15 may include the subject matter of any of Examples F-1 to F-14, and alternatively or additionally any other example herein, wherein the determining the disinfection dosage of the infected article includes determining a temperature reaction of the infected article to UV-C radiation. Example F-16 may include the subject matter of any of Examples F-1 to F-15, and alternatively or additionally any other example herein, wherein the determining the disinfection dosage includes identifying a surface structural configuration the infected article. Example F-17 may include the subject matter of Example F-16, and alternatively or additionally any other example herein, wherein the surface structural configuration includes at least one of a hole, an indentation, a protuberance, and a position within the interior volume.

Example G-1 is a non-transitory storage medium containing executable instructions which, when executed by a processor, configure the processor to operate a disinfection system, comprising: identify a disinfection chamber having an interior volume and a radiation source coupled to the interior volume, the radiation source emitting ultraviolet-C (UV-C) radiation into the interior volume when in operation; determine a UV-C radiation emitting characteristic of the radiation source; receive a structural configuration of the interior volume; receive a surface characteristic of an infected article; estimate a UV-C radiation intensity map within the interior volume based on the UV-C radiation emitting characteristic, the structural configuration of the interior volume and the surface characteristic of the infected article; and determine a disinfection dosage of the infected article based on the UV-C radiation intensity map. Example G-2 may include the subject matter of Example G-1, and alternatively or additionally any other example herein, wherein the determining the disinfection dosage of the infected article includes determining a minimum disinfection dosage.

Example H-1 is a system, comprising: a disinfection chamber having an interior volume; a radiation source coupled to the interior volume, the radiation source emitting disinfecting radiation into the interior volume when in operation; and a control system configured to: control the radiation source to emit the disinfecting radiation according to parameters determined based on at least one of a three dimensional model of the disinfection chamber and a three dimensional model of a target article to be disinfected. Example H-2 may include the subject matter of Example H-1, and alternatively or additionally any other example herein, wherein the three dimensional model of the disinfection chamber is associated with a radiation intensity map created using radiation data collected with at least one radiation sensor or simulated radiation ray information based on a mathematical mapping of the interior volume. Example H-3 may include the subject matter of any of Examples H-1 and H-2, and alternatively or additionally any other example herein, and further comprise: at least one radiation sensor, arranged to measure radiation emitted into the interior volume, wherein the control system is further configured to control the radiation source based on the measured radiation and based on a determined (e.g., calculated) minimum dose of radiation to apply to a target article to be disinfected. Example H-4 may include the subject matter of Example H-3, and alternatively or additionally any other example herein, wherein the determined (e.g., calculated) minimum dose is based on a ratio of radiation delivered to the at least one radiation sensor and radiation delivered to a cold spot of the target article to be disinfected. Example H-5 may include the subject matter of any of Examples H-3 and H-4, and alternatively or additionally any other example herein, wherein the determined (e.g., calculated) minimum dose is further based on a safety factor. Example H-6 may include the subject matter of any of Examples H-1 to H-5, and alternatively or additionally any other example herein, and further comprise: a storage unit that stores an interior volume patterning unit arranged to generate the three dimensional model of the disinfection chamber. Example H-7 may include the subject matter of any of Examples H-1 to H-5, and alternatively or additionally any other example herein, and further comprise: a storage unit that stores a target article patterning unit arranged to generate the three dimensional model of the target article to be disinfected.

Example I-1 is a disinfection system, comprising: a disinfection chamber having an interior volume; a radiation source coupled to the interior volume, the radiation source emitting ultraviolet-C(UV-C) radiation into the interior volume when in operation; a control system configured to: identify a structural configuration of the interior volume; receive a surface characteristic of an infected article; estimate a UV-C radiation intensity map within the interior volume based on the UV-C radiation emitting characteristic, the structural configuration of the interior volume and the surface characteristic of the infected article; and determine a disinfection dosage of the infected article based on the UV-C radiation intensity map. Example I-2 may include the subject matter of Example I-1, and alternatively or additionally any other example herein, and further cause the control system to automatically create a disinfection program executable in a target disinfection chamber, the disinfection program arranged to provide a determined minimum radiation dosage to a target medical device, the disinfection program automatically created based on a combination of a digital map of an exemplary disinfection chamber and a digital map of an exemplary medical device. Example I-3 may include the subject matter of Example I-1 or I-2, and alternatively or additionally any other example herein, and further cause the control system to: create a first digital map of the exemplary disinfection chamber. Example I-4 may include the subject matter of any of Examples I-1 to I-3, and alternatively or additionally any other example herein, and further cause the control system to: provide an exemplary disinfection chamber. Example I-5 may include the subject matter of any of Examples I-1 to I-4, and alternatively or additionally any other example herein, and further cause the control system to: provide an exemplary data collection device having a plurality of data collection sensors. Example I-6 may include the subject matter of any of Examples I-1 to I-5, and alternatively or additionally any other example herein, and further cause the control system to: operate the exemplary disinfection chamber over a determined period of time. Example I-7 may include the subject matter of any of Examples I-1 to I-6, and alternatively or additionally any other example herein, and further cause the control system to: collect UV-C data with the data collection sensors. Example I-8 may include the subject matter of any of Examples I-1 to I-7, and alternatively or additionally any other example herein, and further cause the control system to: create a digital map of the exemplary disinfection chamber. Example I-9 may include the subject matter of any of Examples I-1 to I-8, and alternatively or additionally any other example herein, and further cause the control system to: calibrate of one sensor to another sensor over time. Example I-10 may include the subject matter of any of Examples I-1 to I-9, and alternatively or additionally any other example herein, and further cause the control system to: create a set of virtual points representative of the interior of the exemplary disinfection chamber. Example I-11 may include the subject matter of any of Examples I-1 to I-10, and alternatively or additionally any other example herein, and further cause the control system to: create a map of UV-C for each of the virtual points. Example I-12 may include the subject matter of any of Examples I-1 to I-11, and alternatively or additionally any other example herein, and further cause the control system to: create a map of UV-C vectors within the exemplary disinfection chamber. Example I-13 may include the subject matter of any of Examples I-1 to I-12, and alternatively or additionally any other example herein, and further cause the control system to: create a map of deterioration of the UV-C light sources. Example I-14 may include the subject matter of any of Examples I-1 to I-13, and alternatively or additionally any other example herein, and further cause the control system to: create a map of deterioration of the UV-C light sensors. Example I-15 may include the subject matter of any of Examples I-1 to I-14, and alternatively or additionally any other example herein, and further cause the control system to: create a map of shadows in exemplary disinfection chamber. Example I-16 may include the subject matter of any of Examples I-1 to I-15, and alternatively or additionally any other example herein, and further cause the control system to: create a map of reflection vectors in the exemplary disinfection chamber. Example I-17 may include the subject matter of any of Examples I-1 to I-16, and alternatively or additionally any other example herein, and further cause the control system to: create a map of disinfection regions. Example I-18 may include the subject matter of any of Examples I-1 to I-17, and alternatively or additionally any other example herein, and further cause the control system to: adjust position of on-board detectors. Example I-19 may include the subject matter of any of Examples I-1 to I-18, and alternatively or additionally any other example herein, and further cause the control system to: create a second digital map of the exemplary medical device. Example I-20 may include the subject matter of any of Examples I-1 to I-19, and alternatively or additionally any other example herein, and further cause the control system to: provide an exemplary medical device. Example I-21 may include the subject matter of any of Examples I-1 to I-20, and alternatively or additionally any other example herein, and further cause the control system to: generate a digital model of the exemplary medical device. Example I-22 may include the subject matter of any of Examples I-1 to I-21, and alternatively or additionally any other example herein, and further cause the control system to: create a set of virtual points representative of the surface of the exemplary medical device. Example I-23 may include the subject matter of any of Examples I-1 to I-22, and alternatively or additionally any other example herein, and further cause the control system to: create a model of radiation dose delivered to teach of the virtual points. Example I-24 may include the subject matter of any of Examples I-1 to I-23, and alternatively or additionally any other example herein, and further cause the control system to: identifying locations of interest amongst the set of virtual points. Example I-25 may include the subject matter of any of Examples I-1 to I-24, and alternatively or additionally any other example herein, and further cause the control system to: identify hot spots, wherein optionally, the hot spots are based on an average of collected radiation data values. Example I-26 may include the subject matter of any of Examples I-1 to I-25, and alternatively or additionally any other example herein, and further cause the control system to: identify cold spots, wherein optionally, the hot spots are based on an average of collected radiation data values. Example I-27 may include the subject matter of any of Examples I-1 to I-26, and alternatively or additionally any other example herein, and further cause the control system to: modify the disinfection program to adjust the disinfecting dose to be delivered to the target article to cause all locations intended for disinfection to receive at least the minimum dose required to disinfect to a given level. Example I-28 may include the subject matter of any of Examples I-1 to I-27, and alternatively or additionally any other example herein, and further cause the control system to: generate a map of blocked regions. Example I-29 may include the subject matter of any of Examples I-1 to I-28, and alternatively or additionally any other example herein, and further cause the control system to: generate a map of absorption regions. Example I-30 may include the subject matter of any of Examples I-1 to I-29, and alternatively or additionally any other example herein, and further cause the control system to: collect feedback from onboard sensors and to perform a calibration function based on the feedback, and optionally, said calibration function may compare actual values of data received at the onboard sensors versus expected values of data received at the sensors. Example I-31 may include the subject matter of any of Examples I-1 to I-30, and alternatively or additionally any other example herein, and further cause the control system to: algorithmically combine the first and second digital maps to create the disinfection program. Example I-32 may include the subject matter of any of Examples I-1 to I-31, and alternatively or additionally any other example herein, and further cause the control system to: generate one or more margins for a mis-aligned medical device or a mis-positioned medical device. Example I-33 may include the subject matter of any of Examples I-1 to I-32, and alternatively or additionally any other example herein, and further cause the control system to: load the disinfection program into the target disinfection chamber. Example I-34 may include the subject matter of any of Examples I-1 to I-33, and alternatively or additionally any other example herein, and further cause the control system to: load the target medical device into the disinfection chamber. Example I-35 may include the subject matter of any of Examples I-1 to I-34, and alternatively or additionally any other example herein, and further cause the control system to: execute the disinfection program. Example I-36 may include the subject matter of any of Examples I-1 to I-35, and alternatively or additionally any other example herein, and further cause the control system to: detect a foreign object in the disinfection chamber. Example I-37 may include the subject matter of any of Examples I-1 to I-36, and alternatively or additionally any other example herein, and further cause the control system to: monitor temperature below 35° C. and/or above 55° C. in the disinfection chamber. Example I-38 may include the subject matter of any of Examples I-1 to I-37, and alternatively or additionally any other example herein, wherein the disinfection radiation is at least one of UV-A radiation, UV-B radiation, and UV-C radiation. Example I-39 may include the subject matter of any of Examples I-1 to I-38, and alternatively or additionally any other example herein, wherein the disinfection chamber includes a plurality of reflective surfaces. Example I-40 may include the subject matter of any of Examples I-1 to I-39, and alternatively or additionally any other example herein, wherein the disinfection chamber includes at least one hanger system to cooperatively, mate with a target medical device. Example I-41 may include the subject matter of any of Examples I-1 to I-40, and alternatively or additionally any other example herein, wherein the disinfection chamber includes at least one hanger system to cooperatively, position the target medical device. Example I-42 may include the subject matter of any of Examples I-1 to I-41, and alternatively or additionally any other example herein, wherein the disinfection chamber includes at least one hanger system to cooperatively, orient the target medical device. Example I-43 may include the subject matter of any of Examples I-1 to I-42, and alternatively or additionally any other example herein, wherein objects in the chamber may be non-stationary during disinfection. Example I-44 may include the subject matter of any of Examples I-1 to I-43, and alternatively or additionally any other example herein, and further cause the control system to: control at least one of a number, a rate, and a pattern of UV illumination based on computer-generated model. Example I-45 may include the subject matter of any of Examples I-1 to I-44, and alternatively or additionally any other example herein, and further cause the control system to: adjust the computer-generated model based on at least one of: an age of a radiation source, an age of a radiation sensor, dirt, and actual measurement fluctuation relative to a computer-generated model. Example I-46 may include the subject matter of any of Examples I-1 to I-45, and alternatively or additionally any other example herein, and further cause the control system to: select one of a plurality of disinfection times. Example I-47 may include the subject matter of any of Examples I-1 to I-46, and alternatively or additionally any other example herein, and further cause the control system to: extend a time in a disinfection algorithm based on minimum dose not being reached. Example I-48 may include the subject matter of any of Examples I-1 to I-47, and alternatively or additionally any other example herein, and further cause the control system to: terminate a disinfection cycle to reduce or avoid damage to a target medical object. Example I-49 may include the subject matter of any of Examples I-1 to I-48, and alternatively or additionally any other example herein, and further cause the control system to: determine if a target medical device has been pre-cleaned before disinfection. Example I-50 may include the subject matter of any of Examples I-1 to I-49, and alternatively or additionally any other example herein, and further cause the control system to: execute a fully automatic disinfection protocol. Example I-51 may include the subject matter of any of Examples I-1 to I-50, and alternatively or additionally any other example herein, and further cause the control system to: terminate a disinfection cycle based on at least one of: an average or point exposure, a total exposure, a combination of average or point exposure and total exposure, an elapsed time, or a temperature. Example I-52 may include the subject matter of any of Examples I-1 to I-51, and alternatively or additionally any other example herein, and further cause the control system to: execute a disinfection cycle in less than at least one of less ten minutes, five minutes, three minutes, ninety seconds, or 60 seconds. Example I-53 may include the subject matter of any of Examples I-1 to I-52, and alternatively or additionally any other example herein, wherein the disinfection chamber includes registration indicia to reliably and consistently locate a test article in the disinfection chamber. Example I-54 may include the subject matter of any of Examples I-1 to I-53, and alternatively or additionally any other example herein, wherein the disinfection chamber includes a movable attachment assembly controlled by the control system. Example I-55 may include the subject matter of any of Examples I-1 to I-54, and alternatively or additionally any other example herein, wherein the radiation source provides at least five watts of output radiation power. Example I-56 may include the subject matter of any of Examples I-1 to I-55, and alternatively or additionally any other example herein, wherein the radiation source is arranged to provide a substantially uniform surface irradiation of the disinfection region. Example I-57 may include the subject matter of any of Examples I-1 to I-56, and alternatively or additionally any other example herein, and further cause the control system to: maintain a temperature inside the disinfection unit between about 35° C. and about 45° C.

Having now set forth certain embodiments, further clarification of certain terms used herein may be helpful to providing a more complete understanding of that which is considered inventive in the present disclosure.

The computing devices described herein have electronic memory accessible by at least one processing unit within the device. The memory is programmed with software that directs the one or more processing units. Some of the software modules in the memory control the operation of the computing device with respect to generation, collection, and distribution or other use of data. In some cases, software directs the collection of individual datums, and in other cases, software directs the collection of sets of data.

Software may include a fully executable software program, a simple configuration data file, a link to additional directions, or any combination of known software types. When the computing server updates software, the update may be small or large. For example, in some cases, a computing server downloads a small configuration data file to as part of software, and in other cases, computing server completely replaces all of the present software on the computing device with a fresh version. In some cases, software, data, or software and data is encrypted, encoded, and/or otherwise compressed for reasons that include security, privacy, data transfer speed, data cost, or the like.

Processing devices, or "processors," as described herein, include central processing units (CPU's), microprocessors, microcontrollers (MCU), digital signal processors (DSP), application specific integrated circuits (ASIC), state machines, and the like. Accordingly, a processor as described herein includes any device, system, or part thereof that controls at least one operation, and such a device may be implemented in hardware, firmware, or software, or some combination of at least two of the same. The functionality associated with any particular processor may be centralized or distributed, whether locally or remotely. A processor may interchangeably refer to any type of electronic control circuitry configured to execute programmed software instructions. The programmed instructions may be high-level software instructions, compiled software instructions, assembly-language software instructions, object code, binary code, micro-code, or the like. The programmed instructions may reside in internal or external memory or may be hard-coded as a state machine or set of control signals. According to methods and devices referenced herein, one or more embodiments describe software executable by the processor, which when executed, carries out one or more of the method acts.

As known by one skilled in the art, a computing device, including a mobile computing device, has one or more memories, and each memory may comprise any combination of volatile and non-volatile computer-readable media for reading and writing. Volatile computer-readable media includes, for example, random access memory (RAM). Non-volatile computer-readable media includes, for example, any one or more of read only memory (ROM), magnetic media such as a hard-disk, an optical disk, a flash memory device, a CD-ROM, and the like. In some cases, a particular memory is separated virtually or physically into separate areas, such as a first memory, a second memory, a third memory, etc. In these cases, it is understood that the different divisions of memory may be in different devices or embodied in a single memory. Some or all of the stored contents of a memory may include software instructions executable by a processing device to carry out one or more particular acts.

In the present disclosure, memory may be used in one configuration or another. The memory may be configured to store data. In the alternative or in addition, the memory may be a non-transitory computer readable medium (CRM) wherein the CRM is configured to store instructions executable by a processor. The instructions may be stored individually or as groups of instructions in files. The files may include functions, services, libraries, and the like. The files may include one or more computer programs or may be part of a larger computer program. Alternatively or in addition, each file may include data or other computational support material useful to carry out the computing functions of the systems, methods, and apparatus described in the present disclosure.

FIGS. 9 to 12 are data flow diagrams illustrating processes that may be used by embodiments of computing devices such as disinfection systems 100. In this regard, each described process may represent a module, segment, or portion of code, which comprises one or more executable instructions for implementing the specified logical function(s). It should also be noted that in some implementations, the functions noted in the process may occur in a different order, may include additional functions, may occur concurrently, and/or may be omitted.

As used herein, the term "module" refers to an electronic circuit, a processor unit (e.g., shared, dedicated, group, single core, multicore, or the like) and memory operative to execute one or more software or firmware programs, an application specific integrated circuit (ASIC), a combinational logic circuit, or some other individual or cooperative coupling of suitable components (either hardware or software) that provides the functionally described with respect to the module.

The terms, "real-time" or "real time," as used herein and in the claims that follow, are not intended to imply instantaneous processing, transmission, reception, or otherwise as the case may be. Instead, the terms, "real-time" and "real time" imply that the activity occurs over an acceptably short period of time (e.g., over a period of microseconds or milliseconds), and that the activity may be performed on an ongoing basis (e.g., measuring radiation with sensors 130, determining if a minimum dose of radiation has been delivered, and the like). An example of an activity that is not real-time is one that occurs over an extended period of time (e.g., hours or days) or that occurs based on intervention or direction by a person or other activity.

Where the terms "substantial" or "about" in any grammatical form are used as modifiers in the present disclosure and any appended claims (e.g., to modify a structure, a dimension, a measurement, or some other characteristic), it is understood that the characteristic may vary by up to 30 percent. For example, a disinfection chamber may include a plurality of radiation sources mounted "substantially parallel." In these cases, a two radiation sources that are mounted exactly parallel are mounted along a common "X" axis and a "Y" axis that is normal (i.e., 90 degrees or at right angle) to a plane or line formed by a "Z" axis. Different from the exact precision of the term, "parallel," and the use of "substantially" or "about" to modify the characteristic permits a variance of the particular characteristic by up to 30 percent.

In the foregoing description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with electronic and computing systems including client and server computing systems, as well as networks have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, e.g., "including, but not limited to."

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the context clearly dictates otherwise. It should also be noted that the term "or" is generally employed as including "and/or" unless the context clearly dictates otherwise.

As used herein, the term "about" or "approximately" when used in conjunction with a number refers to any number within one percent, five percent, or ten percent (1%, 5% or 10%) of the referenced number.

The headings and Abstract of the Disclosure provided herein are for convenience only and do not interpret the scope or meaning of the embodiments.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method, comprising providing a disinfection chamber having an interior volume and at least one radiation source coupled to the interior volume, the at least one radiation source arranged to emit disinfecting radiation into the interior volume when in operation, determining a cold spot of a target article to be disinfected; and providing a disinfection program to the disinfection chamber, the disinfection program arranged to control the at least one radiation source to emit the disinfecting radiation according to the determined cold spot;
wherein the disinfection program is based on a radiation intensity map, said radiation intensity map based on at least one radiation emitting characteristic of the at least one radiation source.

2. The method according to claim 1, further comprising:
identifying a plurality of regions of the target article to be disinfected;
in the plurality of regions, determining a quantity of disinfecting radiation that will be received at each of the plurality of regions over a selected time period;
comparing the quantities of disinfecting radiation to determine which region will receive a least amount of disinfecting radiation; and
identifying the region that will receive the least amount of disinfecting radiation as the determined cold spot of the target article to be disinfected.

3. The method according to claim 1, comprising identifying a first region of the target article that will receive less disinfecting radiation than a second region of the target article.

4. The method of claim 3, wherein the receipt of less disinfecting radiation at the first region is caused, at least in part, by an interaction between geometry of the first region and geometry of the disinfection chamber or the second region.

5. The method of claim 3, wherein the receipt of less disinfecting radiation at the first region is caused, at least in part, by a position of the target article in the disinfection chamber.

6. The method of claim 3, wherein the receipt of less disinfecting radiation at the first region is caused, at least in part, by a determined value representing an amount of absorption associated with at least one of the target article and the disinfection chamber.

7. The method of claim 3, wherein the receipt of less disinfecting radiation at the first region is caused, at least in part, by a determined value representing an amount of reflectivity or diffusion associated with at least one of the target article and the disinfection chamber.

8. The method of claim 3, wherein the receipt of less disinfecting radiation at the first region is caused, at least in part, by a position of each of the at least one radiation source in the disinfection chamber.

9. The method according to claim 3, further comprising modeling the geometry of the first region and either modeling the geometry of the disinfection chamber, and modeling disinfecting radiation in the disinfection chamber to determine the first and second regions, or modeling the geometry of the second region, and modeling an obstruction of the disinfecting radiation to the first region.

10. The method according to claim 1, comprising providing an indication that the target article is improperly placed in the disinfection chamber.

11. The method according to claim 1, wherein control of the at least one radiation source to emit the disinfecting radiation according to the determined cold spot includes emitting the disinfecting radiation for a determined period of time.

12. The method according to claim 1, wherein control of the at least one radiation source to emit the disinfecting radiation according to the determined cold spot includes:
determining an amount of disinfecting radiation received at a sensor, wherein the amount of disinfecting radiation received at the sensor is indicative of how much disinfecting radiation is received at the determined cold spot; and
ending emission of disinfecting radiation based on the determined amount of disinfecting radiation received at the sensor;
wherein determining the amount of disinfecting radiation received at the sensor includes collecting data from the sensor over time.

13. The method according to claim 1 further comprising:
positioning a calibration object in the interior volume;
operating the at least one radiation source with the calibration object in the interior volume;
measuring a radiation intensity value on a portion of the calibration object with the operating of the at least one radiation source; and updating the radiation intensity map based on the measured radiation intensity value.

14. The method according to claim 1 wherein the radiation intensity map has multiple radiation intensity values for a same spot in the interior volume, and wherein each of the multiple radiation intensity values is associated with a time factor of the operating of the at least one radiation source.

* * * * *